(12) United States Patent
Cai et al.

(10) Patent No.: US 7,629,488 B2
(45) Date of Patent: Dec. 8, 2009

(54) PROCESS FOR THE PREPARATION OF OPIOID MODULATORS

(75) Inventors: Chaozhong Cai, North Wales, PA (US); Wei He, Audubon, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 453 days.

(21) Appl. No.: 11/368,564

(22) Filed: Mar. 6, 2006

(65) Prior Publication Data

US 2006/0211863 A1    Sep. 21, 2006

Related U.S. Application Data

(60) Provisional application No. 60/661,784, filed on Mar. 14, 2005.

(51) Int. Cl.
*C07C 51/10* (2006.01)
(52) U.S. Cl. .................. 562/406; 562/400; 562/405
(58) Field of Classification Search ............ 562/400, 562/405, 406
See application file for complete search history.

(56) References Cited

U.S. PATENT DOCUMENTS

2005/0203143 A1 * 9/2005 Breslin et al. ............... 514/326

FOREIGN PATENT DOCUMENTS

| WO | WO 03/092688 | 11/2003 |
| WO | WO 2005/090315 | 9/2005 |

OTHER PUBLICATIONS

International Search Report for PCT/US2006/008450, dated Jul. 13, 2006.

* cited by examiner

*Primary Examiner*—Kamal A Saeed
*Assistant Examiner*—Samantha L Shterengarts

(57) ABSTRACT

The present invention is directed to novel processes for the preparation of opioid modulators (agonists and antagonists) and intermediates in their synthesis. The opioid modulators are useful for the treatment and prevention of as pain and gastrointestinal disorders.

10 Claims, No Drawings

PROCESS FOR THE PREPARATION OF OPIOID MODULATORS

CROSS REFERENCE TO RELATED APPLICATIONS

This application claims the benefit of U.S. Provisional Application 60/661,784, filed on Mar. 14, 2005, which is incorporated by reference herein in its entirety.

FIELD OF THE INVENTION

The present invention is directed to a novel process for the preparation of opioid modulators (agonists and antagonists), and intermediates in their synthesis. The opioid modulators are useful in the treatment and prevention of such disorders as pain, visceral pain including post-operative pain, gastrointestinal disorders including diarrheic syndromes, motility disorders including post-operative ileus, constipation, irritable bowel syndrome and inflammatory bowel disorders.

BACKGROUND OF THE INVENTION

The present invention is directed to the preparation of novel opioid receptor modulators and intermediates in their synthesis. More specifically, the present invention is directed to novel processes for the preparation of compounds of formula (II)

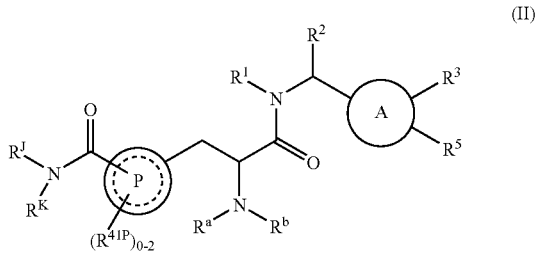

(II)

wherein all variables are as hereinafter defined, disclosed in U.S. patent application Ser. No. 11/079,647, filed Mar. 15, 2004, and published as US Patent Publication US-2005-0203143-A1, Sep. 15, 2005, which is hereby incorporated by reference in its entirety.

Known methods for the preparation of the compounds of formula (II) and compounds of formula (I), as herein defined, require the use of dimethyl-tyrosine, which is expensive and thus not suitable for large scale synthesis. Thus there remains a need for a process for the preparation of compounds of formula (I) and compounds of formula (II) which is suitable for large scale production.

SUMMARY OF THE INVENTION

The present invention is directed to a process for the preparation of compounds of formula (I)

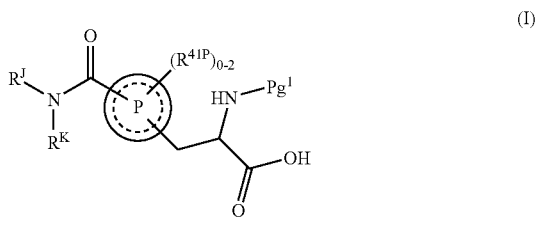

(I)

wherein

is $C_{6-10}$aryl or a heteroaryl selected from the group consisting of furyl, thienyl, pyrrolyl, oxazolyl, thiazolyl, imidazolyl, pyrazolyl, pyridinyl, pyrimidinyl, pyrazinyl, indolyl, isoindolyl, indolinyl, benzofuryl, benzothienyl, benzimidazolyl, benzthiazolyl, benzoxazolyl, quinolizinyl, quinolinyl, isoquinolinyl and quinazolinyl;

each $R^{41P}$ is independently selected from $C_{1-6}$alkyl, $C_{1-6}$alkoxy or fluoro;

$R^J$ and $R^K$ are each independently selected from hydrogen or $C_{1-4}$alkyl; alternatively, $R^J$ and $R^K$ are taken together with the nitrogen atom to which they are bound to form a five to seven membered heterocyclyl;

$Pg^1$ is a nitrogen protecting group;

comprising

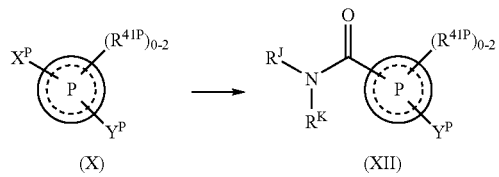

reacting a compound of formula (X), wherein $X^P$ is selected from OH, CN, —$CO_2H$, —C(O)—Cl or —C(O)—$OC_{1-4}$alkyl and wherein $Y^P$ is selected from Br, Cl or I, to yield the corresponding compound of formula (XII);

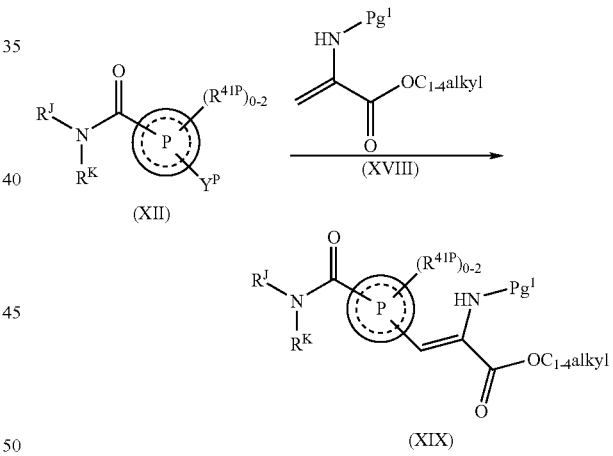

reacting the compound of formula (XII) with a suitably substituted compound of formula (XVIII); in the presence of palladium catalyst; in the presence of an organic or inorganic base; in an organic solvent; at a temperature greater than about room temperature; to yield the corresponding compound of formula (XIX);

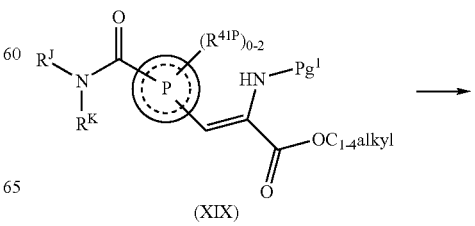

(XIX)

-continued

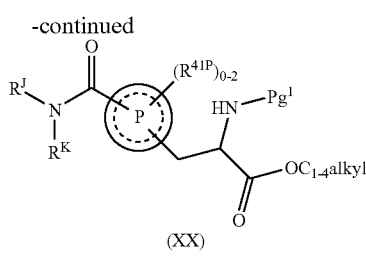

(XX)

reacting the compound of formula (XIX) with hydrogen or a source of hydrogen; in the presence of a catalyst; in a solvent; at a temperature greater than about room temperature; to yield the corresponding compound of formula (XX);

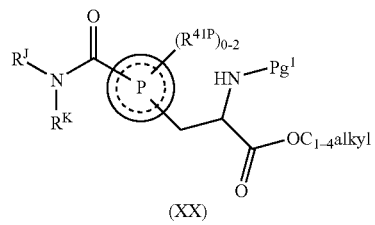

(XX)

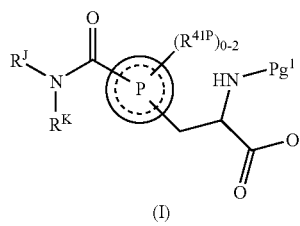

(I)

reacting the compound of formula (XX) with an aqueous base; in an organic solvent; to yield the corresponding compound of formula (I).

The present invention is further directed to a process for the preparation of a compound of formula (I)

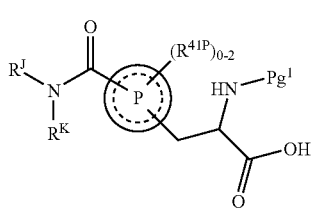

(I)

wherein

is $C_{6-10}$aryl or a heteroaryl selected from the group consisting of furyl, thienyl, pyrrolyl, oxazolyl, thiazolyl, imidazolyl, pyrazolyl, pyridinyl, pyrimidinyl, pyrazinyl, indolyl, isoindolyl, indolinyl, benzofuryl, benzothienyl, benzimidazolyl, benzthiazolyl, benzoxazolyl, quinolizinyl, quinolinyl, isoquinolinyl and quinazolinyl;

each $R^{41P}$ is independently selected from $C_{1-6}$alkyl, $C_{1-6}$alkoxy or fluoro;

$R^J$ and $R^K$ are each independently selected from hydrogen or $C_{1-4}$alkyl;

alternatively, $R^J$ and $R^K$ are taken together with the nitrogen atom to which they are bound to form a five to seven membered heterocyclyl;

$Pg^1$ is a nitrogen protecting group;

comprising

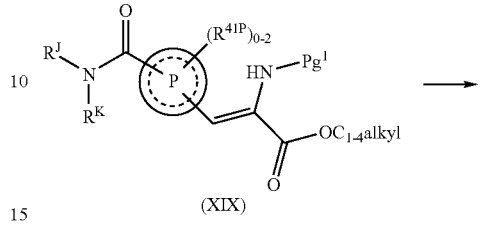

(XIX)

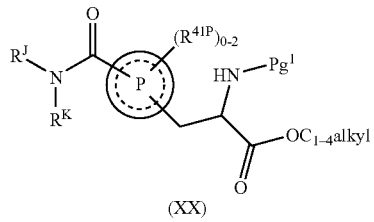

(XX)

reacting the compound of formula (XIX) with hydrogen or a source of hydrogen; in the presence of a catalyst; in a solvent; at a temperature greater than about room temperature; to yield the corresponding compound of formula (XX);

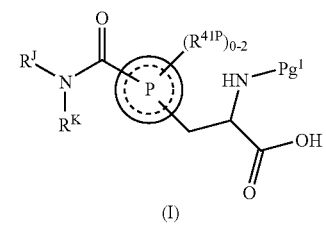

(XX)

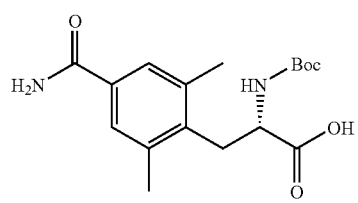

(I)

reacting the compound of formula (XX) with an aqueous base; in an organic solvent; to yield the corresponding compound of formula (I).

The present invention is further directed to a process for the preparation of a compound of formula (Ia) (also known as, 4-(aminocarbonyl)-N-[(1,1-dimethylethoxy)carbonyl]-2,6-dimethyl-L-phenylalanine)

(Ia)

comprising

-continued

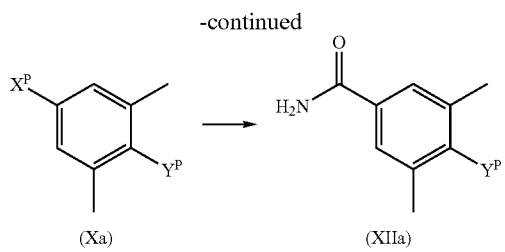

reacting a compound of formula (Xa), wherein $X^P$ is selected from OH, CN, —CO$_2$H, —C(O)—Cl or —C(O)—OC$_{1-4}$alkyl and wherein $Y^P$ is selected from Br, Cl or I, to yield the corresponding compound of formula (XIIa);

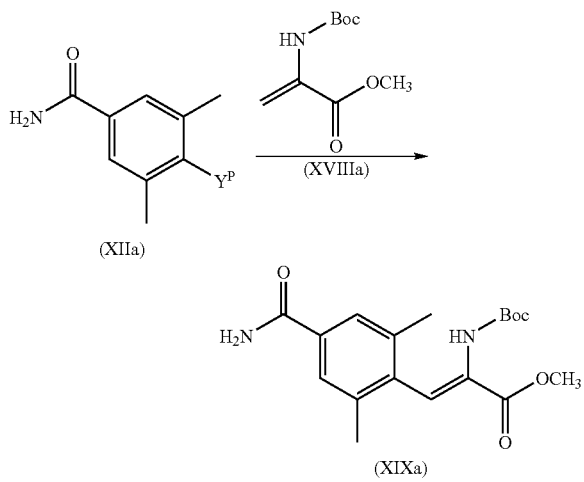

reacting the compound of formula (XIIa) with a suitably substituted compound of formula (XVIIIa); in the presence of palladium catalyst; in the presence of an organic or inorganic base; in an organic solvent; at a temperature greater than about room temperature; to yield the corresponding compound of formula (XIXa);

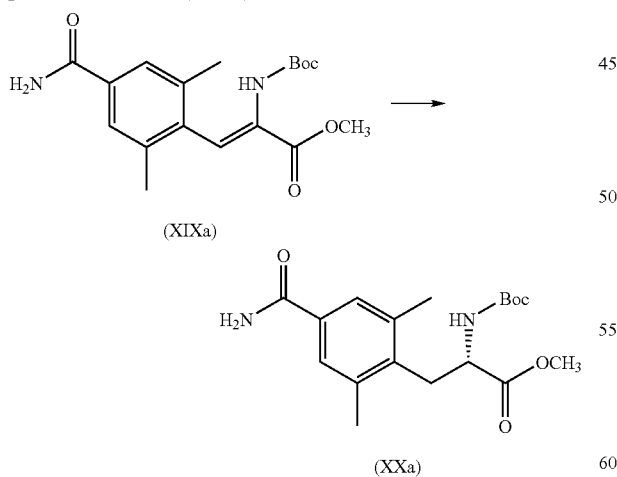

reacting compound of formula (XIXa) with hydrogen gas, at a pressure sufficient to hydrogenate; in the presence of a suitable chiral catalyst; at a temperature greater than about room temperature; in an organic solvent; to yield the corresponding compound of formula (XXa);

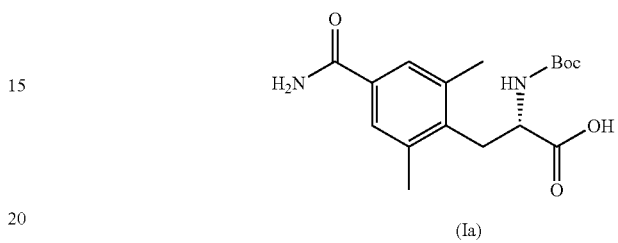

reacting the compound of formula (XXa) with an aqueous base; in an organic solvent; to yield the corresponding compound of formula (Ia).

The present invention is further directed to a process for the preparation of the compound of formula (Ia)

(Ia)

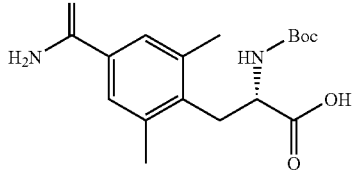

comprising

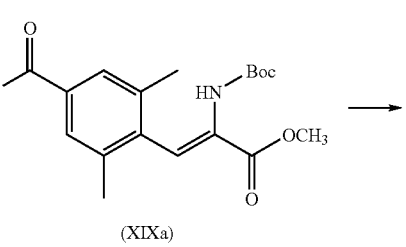

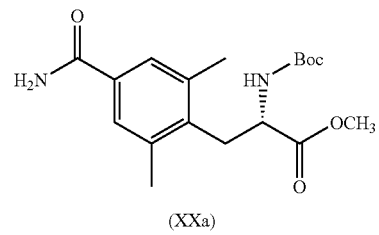

reacting compound of formula (XIXa) with hydrogen gas, at a pressure sufficient to hydrogenate; in the presence of a suitable chiral catalyst; at a temperature greater than about room temperature; in an organic solvent; to yield the corresponding compound of formula (XXa);

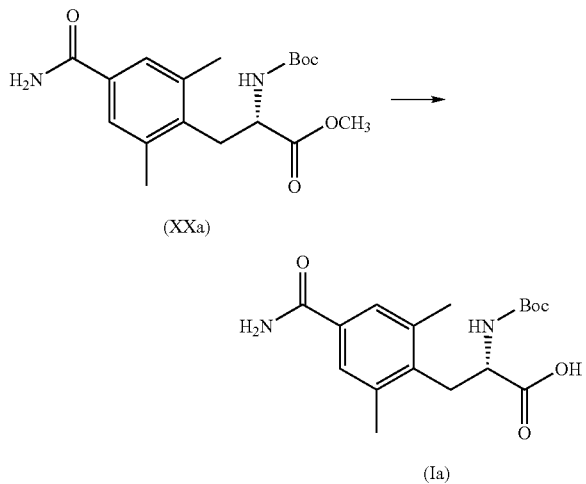

(XXa)

(Ia)

reacting the compound of formula (XXa) with an aqueous base; in an organic solvent; to yield the corresponding compound of formula (Ia).

The present invention is further directed to processes for the preparation of compounds of formula (XIX)

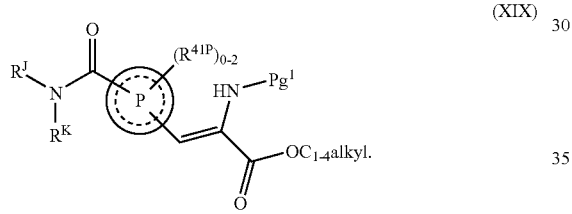

(XIX)

The present invention is further directed to processes for the preparation of the compound of formula (XIXb)

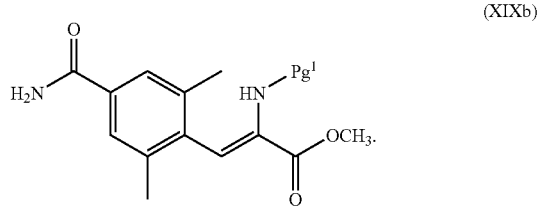

(XIXb)

The present invention is further directed to a process for the preparation of compounds of formula (II)

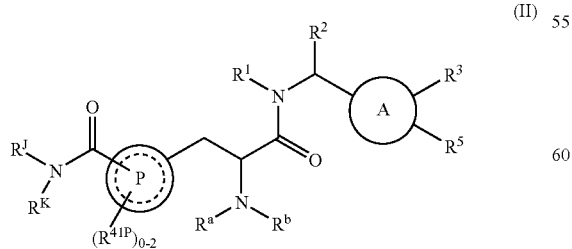

(II)

wherein

is $C_{6-10}$aryl or a heteroaryl selected from the group consisting of furyl, thienyl, pyrrolyl, oxazolyl, thiazolyl, imidazolyl, pyrazolyl, pyridinyl, pyrimidinyl, pyrazinyl, indolyl, isoindolyl, indolinyl, benzofuryl, benzothienyl, benzimidazolyl, benzthiazolyl, benzoxazolyl, quinolizinyl, quinolinyl, isoquinolinyl and quinazolinyl;

each $R^{41P}$ is independently selected from $C_{1-6}$alkyl, $C_{1-6}$alkoxy or fluoro;

$R^J$ and $R^K$ are each independently selected from hydrogen or $C_{1-4}$alkyl; alternatively, $R^J$ and $R^K$ are taken together with the nitrogen atom to which they are bound to form a five to seven membered heterocyclyl;

$R^1$ is selected from the group consisting of hydrogen, $C_{1-6}$alkyl, cycloalkyl, heterocyclyl, aryl($C_{1-6}$)alkyl, and heteroaryl($C_{1-6}$)alkyl;

wherein when $R^1$ is phenyl($C_{1-6}$)alkyl, phenyl is optionally fused to a heterocyclyl or cycloalkyl;

wherein when $R^1$ is $C_{1-2}$alkyl, said $C_{1-2}$alkyl is optionally substituted with one to two substituents independently selected from the group consisting of $C_{1-6}$alkoxy, aryl, cycloalkyl, heterocyclyl, hydroxy, cyano, amino, $C_{1-6}$alkylamino, ($C_{1-6}$alkyl)$_2$amino, trifluoromethyl, and carboxy;

and further, wherein when $R^1$ is $C_{3-6}$alkyl, said $C_{3-6}$alkyl is optionally substituted with one to three substituents independently selected from the group consisting of $C_{1-6}$alkoxy, aryl, cycloalkyl, heterocyclyl, hydroxy, cyano, amino, $C_{1-6}$alkylamino, ($C_{1-6}$alkyl)$_2$amino, trifluoromethyl, and carboxy;

wherein the cycloalkyl and heterocyclyl of $C_{1-2}$alkyl and $C_{3-6}$alkyl are optionally substituted with one to two substituents independently selected from the group consisting of $C_{1-6}$alkyl, hydroxy($C_{1-6}$)alkyl, $C_{1-6}$alkoxy, hydroxy, cyano, amino, $C_{1-6}$alkylamino, ($C_{1-6}$alkyl)$_2$amino, trifluoromethyl, carboxy, aryl($C_{1-6}$)alkoxycarbonyl, $C_{1-6}$alkoxycarbonyl, aminocarbonyl, $C_{1-6}$alkylaminocarbonyl, ($C_{1-6}$alkyl)$_2$aminocarbonyl, and aminosulfonyl;

furthermore, wherein the cycloalkyl and heterocyclyl of $R^1$ are optionally substituted with one to two substituents independently selected from the group consisting of $C_{1-6}$alkyl, hydroxy($C_{1-6}$)alkyl, $C_{1-6}$alkoxy, hydroxy, cyano, amino, $C_{1-6}$alkylamino, ($C_{1-6}$alkyl)$_2$amino, trifluoromethyl, carboxy, aryl($C_{1-6}$)alkoxycarbonyl, $C_{1-6}$alkoxycarbonyl, aminocarbonyl, $C_{1-6}$alkylaminocarbonyl, ($C_{1-6}$alkyl)$_2$aminocarbonyl, and aminosulfonyl;

furthermore, wherein the aryl and heteroaryl portion of the $R^1$ substituents aryl($C_{1-6}$)alkyl and heteroaryl($C_{1-6}$)alkyl, are optionally substituted with one to three $R^{11}$ substituents independently selected from the group consisting of $C_{1-6}$alkyl; hydroxy($C_{1-6}$)alkyl; $C_{1-6}$alkoxy; $C_{6-10}$aryl($C_{1-6}$)alkyl; $C_{6-10}$aryl($C_{1-6}$)alkoxy; $C_{6-10}$aryl; heteroaryl optionally substituted with one to two substituents independently selected from the group consisting of $C_{1-4}$alkyl, $C_{1-4}$alkoxy, and carboxy; cycloalkyl; heterocyclyl; $C_{6-10}$aryloxy; heteroaryloxy; cycloalkyloxy; heterocyclyloxy; amino; $C_{1-6}$alkylamino; ($C_{1-6}$alkyl)$_2$amino; $C_{3-6}$cycloalkylaminocarbonyl; hydroxy($C_{1-6}$)alkylaminocarbonyl; $C_{6-10}$arylaminocarbonyl wherein $C_{6-10}$aryl is optionally substituted with carboxy or $C_{1-4}$alkoxycarbonyl; heterocyclylcarbonyl; carboxy; $C_{1-6}$alkylcarbonyloxy; $C_{1-6}$alkoxycarbonyl; $C_{1-6}$alkylcarbonyl; $C_{1-6}$alkylcarbonylamino; aminocarbonyl; $C_{1-6}$alkylaminocarbonyl; $(C_{1-6}$alkyl$)_2$aminocarbonyl; cyano; halogen; trifluoromethyl; trifluoromethoxy; and hydroxy;

provided that no more than one $R^{11}$ substituent is selected from the group consisting of $C_{6-10}$aryl($C_{1-6}$)alkyl; $C_{6-10}$aryl($C_{1-6}$)alkoxy; $C_{6-10}$aryl; heteroaryl optionally substituted with one to two substituents independently selected from the group consisting of $C_{1-4}$alkyl, $C_{1-4}$alkoxy, and carboxy; cycloalkyl; heterocyclyl; $C_{6-10}$aryloxy; heteroaryloxy; cycloalkyloxy; $C_{6-10}$arylaminocarbonyl, heterocyclylcarbonyl; and heterocyclyloxy;

$R^2$ is hydrogen, $C_{1-8}$alkyl, hydroxy($C_{1-8}$)alkyl, $C_{6-10}$aryl($C_{1-6}$)alkoxy($C_{1-6}$)alkyl, or $C_{6-10}$aryl($C_{1-8}$)alkyl;

wherein the $C_{6-10}$aryl group in the $C_{6-10}$aryl-containing substituents of $R^2$ is optionally substituted with one to two substituents independently selected from the group consisting of $C_{1-6}$alkyl, $C_{1-6}$alkoxy, hydroxy, amino, $C_{1-6}$alkylamino, $(C_{1-6}$alkyl$)_2$amino, aminocarbonyl, $C_{1-6}$alkylaminocarbonyl, $(C_{1-6}$alkyl$)_2$aminocarbonyl, cyano, fluoro, chloro, bromo, trifluoromethyl, and trifluoromethoxy; and, wherein the $C_{1-6}$alkyl and $C_{1-6}$alkoxy substituents of aryl are optionally substituted with hydroxy, amino, $C_{1-6}$alkylamino, $(C_{1-6}$alkyl$)_2$amino, or $C_{6-10}$aryl;

A is selected from the group consisting of aryl, ring system a-1, a-2, a-3, and a-4, optionally substituted with $R^3$ and $R^5$;

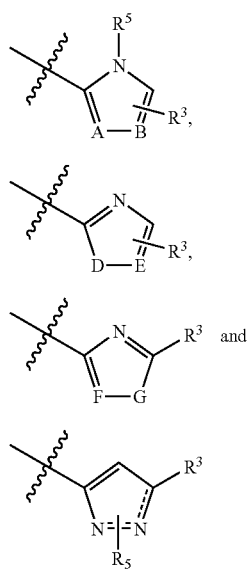

a-1 a-2 a-3 a-4 wherein A-B is selected from the group consisting of N—C, C—N, N—N and C—C; wherein D-E is selected from the group consisting of O—C, S—C, and O—N; and wherein F-G is selected from the group consisting of N—O and C—O;

$R^3$ is one to two substituents independently selected from the group consisting of $C_{1-6}$alkyl, aryl, aryl($C_{1-6}$)alkyl, aryl($C_{2-6}$)alkenyl, aryl($C_{2-6}$)alkynyl, heteroaryl, heteroaryl($C_{1-6}$)alkyl, heteroaryl($C_{2-6}$)alkenyl, heteroaryl($C_{2-6}$)alkynyl, amino, $C_{1-6}$alkylamino, $(C_{1-6}$alkyl$)_2$amino, arylamino, heteroarylamino, aryloxy, heteroaryloxy, trifluoromethyl, and halogen;

wherein the aryl, heteroaryl, and the aryl and heteroaryl of aryl($C_{1-6}$)alkyl, aryl($C_{2-6}$)alkenyl, aryl($C_{2-6}$)alkynyl, heteroaryl($C_{1-6}$)alkyl, heteroaryl($C_{2-6}$)alkenyl, alkenyl, heteroaryl($C_{2-6}$)alkynyl, arylamino, heteroarylamino, aryloxy, and heteroaryloxy, are optionally substituted with one to five fluoro substituents or one to three substituents independently selected from the group consisting of $C_{1-6}$alkyl, hydroxy($C_{1-6}$)alkyl, $C_{1-6}$alkoxy, $C_{6-10}$aryl($C_{1-6}$alkyl, $C_{6-10}$aryl($C_{1-6}$)alkoxy, $C_{6-10}$aryl, $C_{6-10}$aryloxy, heteroaryl($C_{1-6}$)alkyl, heteroaryl($C_{1-6}$)alkoxy, heteroaryl, heteroaryloxy, $C_{6-10}$arylamino, heteroarylamino, amino, $C_{1-6}$alkylamino, $(C_{1-6}$alkyl$)_2$amino, carboxy($C_{1-6}$)alkyl, alkylamino, carboxy, $C_{1-6}$alkylcarbonyl, $C_{1-6}$alkoxycarbonyl, $C_{1-6}$alkylcarbonylamino, aminocarbonyl, $C_{1-6}$alkylaminocarbonyl, $(C_{1-6}$alkyl$)_2$aminocarbonyl, carboxy($C_{1-6}$)alkylaminocarbonyl, cyano, halogen, trifluoromethyl, trifluoromethoxy, hydroxy, $C_{1-6}$alkylsulfonyl, and $C_{1-6}$alkylsulfonylamino; provided that not more than one such substituent on aryl and heteroaryl portion of $R^3$ is selected from the group consisting of $C_{6-10}$aryl, heteroaryl, $C_{6-10}$aryl($C_{1-6}$)alkyl, $C_{6-10}$aryl($C_{6-10}$)alkoxy, aryl($C_{2-6}$)alkenyl, aryl($C_{2-6}$)alkynyl, heteroaryl, heteroaryl($C_{1-6}$)alkyl, heteroaryl($C_{2-6}$)alkoxy, $C_{6-10}$arylamino, heteroarylamino, $C_{6-10}$aryloxy, and heteroaryloxy;

and wherein $C_{1-6}$alkyl, and $C_{1-6}$alkyl of aryl($C_{1-6}$)alkyl and heteroaryl($C_{1-6}$)alkyl, are optionally substituted with a substituent selected from the group consisting of hydroxy, carboxy, $C_{1-4}$alkoxycarbonyl, amino, $C_{1-6}$alkylamino, $(C_{1-6}$alkyl$)_2$amino, aminocarbonyl, $(C_{1-4}$)alkylaminocarbonyl, di($C_{1-4}$)alkylaminocarbonyl, aryl, heteroaryl, arylamino, heteroarylamino, aryloxy, heteroaryloxy, aryl($C_{1-4}$)alkoxy, and heteroaryl($C_{1-4}$)alkoxy;

$R^5$ is a substituent on a nitrogen atom of ring A selected from the group consisting of hydrogen and $C_{1-4}$alkyl;

$R^a$ and $R^b$ are independently selected from the group consisting of hydrogen, $C_{1-6}$alkyl, and $C_{1-6}$alkoxycarbonyl; alternatively, when $R^a$ and $R^b$ are each other than hydrogen, $R^a$ and $R^b$ are optionally taken together with the nitrogen atom to which they are both attached to form a five to eight membered monocyclic ring;

and pharmaceutically acceptable enantiomers, diastereomers, racemates, and salts thereof;

comprising

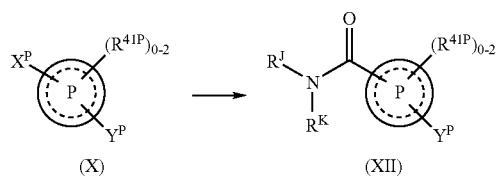

reacting a compound of formula (X), wherein $X^P$ is selected from OH, CN, —CO$_2$H, —C(O)—Cl or —C(O)—OC$_{1-4}$alkyl and wherein $Y^P$ is selected from Br, Cl or I, to yield the corresponding compound of formula (XII);

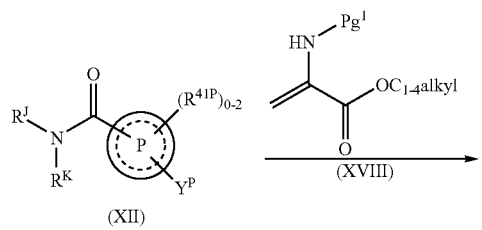

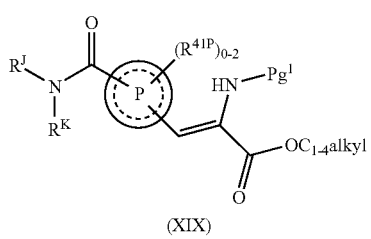

reacting the compound of formula (XII) with a suitably substituted compound of formula (XVIII) wherein $Pg^1$ is a nitrogen protecting group; in the presence of palladium catalyst; in the presence of an organic or inorganic base; in an organic solvent; at a temperature greater than about room temperature; to yield the corresponding compound of formula (XIX);

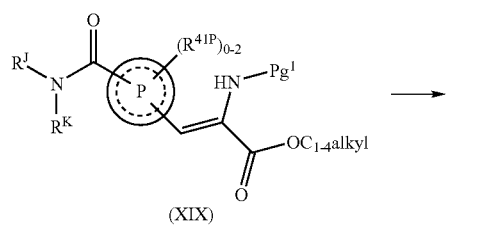

reacting the compound of formula (XIX) with hydrogen or a source of hydrogen; in the presence of a catalyst; in a solvent; at a temperature greater than about room temperature; to yield the corresponding compound of formula (XX);

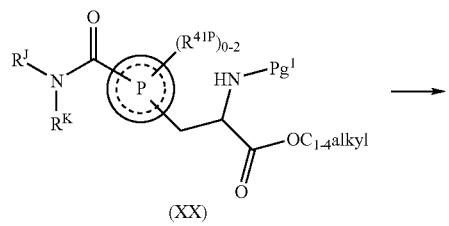

-continued

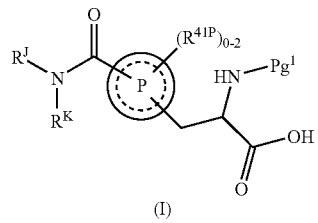

reacting the compound of formula (XX) with an aqueous base; in an organic solvent; to yield the corresponding compound of formula (I);

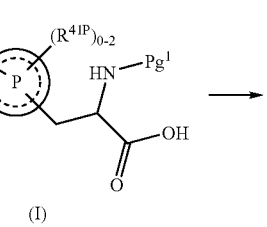

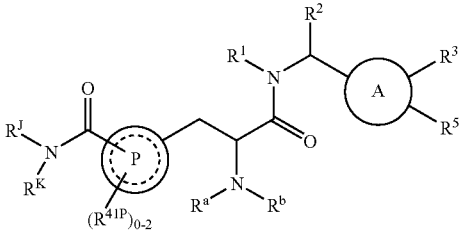

reacting the compound of formula (I), to yield the corresponding compound of formula (II).

In an embodiment, the present invention is directed to processes for the preparation of the compound of formula (IV)

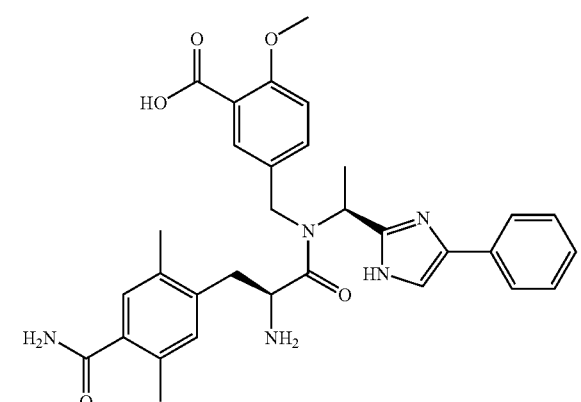

also known as, 5-({[2-amino-3-(4-carbamoyl-2,5-dimethyl-phenyl)-propionyl]-[1-(4-phenyl-1H-imidazol-2-yl)-ethyl]-amino}-methyl)-2-methoxy-benzoic acid.

In an embodiment, the present invention is directed to processes for the preparation of the compound of formula (V)

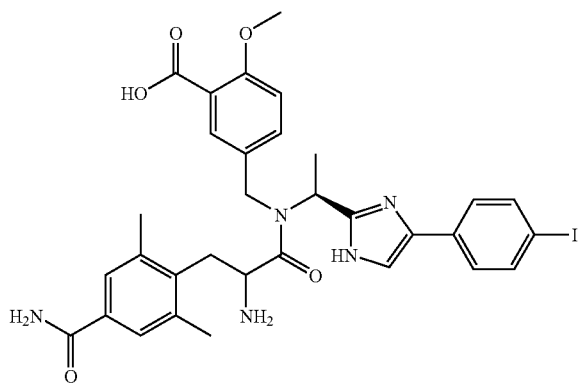

(V)

also known as, 5-[([2-Amino-3-(4-carbamoyl-2,6-dimethyl-phenyl)-propionyl]-{1-[4-(4-iodo-phenyl)-1H-imidazol-2-yl]-ethyl}-amino)-methyl]-2-methoxy-benzoic acid.

The present invention is further directed to a product prepared according to any of the processes described herein.

Illustrative of the invention is a pharmaceutical composition comprising a pharmaceutically acceptable carrier and at a product prepared according to the process described herein. An illustration of the invention is a pharmaceutical composition made by mixing a product prepared according to the process described herein and a pharmaceutically acceptable carrier. Illustrating the invention is a process for making a pharmaceutical composition comprising mixing a product prepared according to the process described herein and a pharmaceutically acceptable carrier.

Exemplifying the invention are methods of treating or preventing a disorder mediated by at least one opioid receptor, preferably the δ or μ opioid receptor selected from the group consisting of pain and gastrointestinal disorders, in a subject in need thereof comprising administering to the subject a therapeutically effective amount of any of the compounds or pharmaceutical compositions prepared as described above.

DETAILED DESCRIPTION OF THE INVENTION

The present invention is directed to processes for the preparation of compounds of formula (I)

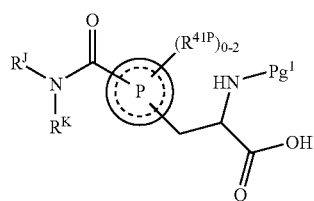

(I)

wherein $Pg^1$,

$R^J$, $R^K$ and $R^{41P}$ are as herein defined. The compounds of formula (I) are useful in the preparation of opioid receptor modulators—compounds of formula (II) as defined herein. The present invention is further directed to processes for the preparation of the compound of formula (Ia) as herein defined, useful as intermediates in the synthesis of opioid receptor modulators.

In an embodiment, the present invention is directed to processes for the preparation of compounds wherein the

ring is unsubstituted. In an embodiment of the present invention, the

ring is substituted with one $R^{41P}$ group, which is bound at the 2- or 6-position. In another embodiment, the present invention is directed to processes for the preparation of compounds wherein the

ring is substituted with two $R^{41P}$ groups, which are bound at the 2- and 6-positions. For example, processes wherein

is phenyl, the compound of formula (I) is of the following structure:

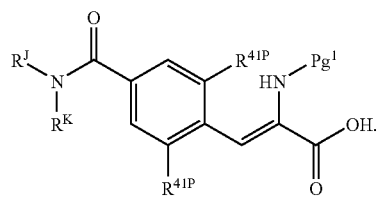

In an embodiment, the present invention is directed to processes for the preparation of compounds of formula (Ic)

(Ic)

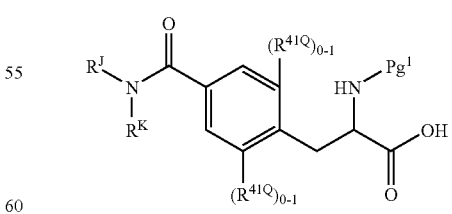

wherein $R^{41Q}$ is selected from methyl, ethyl, methoxy, ethoxy or fluoro and wherein $R^J$, $R^K$ and $Pg^1$ are as herein defined.

In another embodiment, the present invention is directed to processes for the preparation of the compound of formula (Ib)

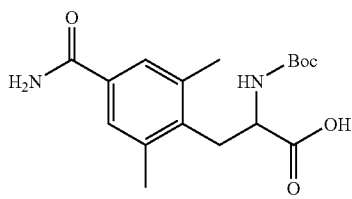

(Ib)

(i.e. a compound of formula (I) wherein

is phenyl; $R^J$ and $R^K$ are each hydrogen; the phenyl ring is further substituted with two $R^{41P}$ groups, which are each methyl and $Pg^1$ is Boc), also known as 2-tert-butoxycarbonylamino-3-(4-carbamoyl-2,6-dimethyl-phenyl)-propionic acid.

In another embodiment, the present invention is directed to processes for the preparation of the compound of formula (Ia)

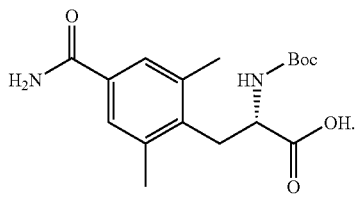

(Ia)

The present invention is further directed to processes for the preparation of compounds of formula (XIX)

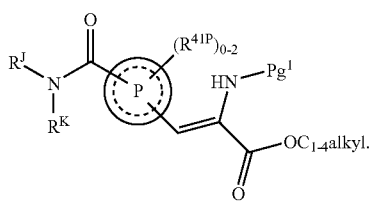

(XIX)

In an embodiment, the present invention is directed to processes for the preparation of the compound of formula (XIXb),

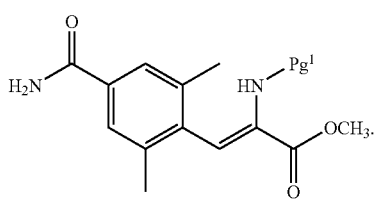

(XIXb)

Preferably, the present invention is directed to processes for the preparation of the compound of formula (XIXa)

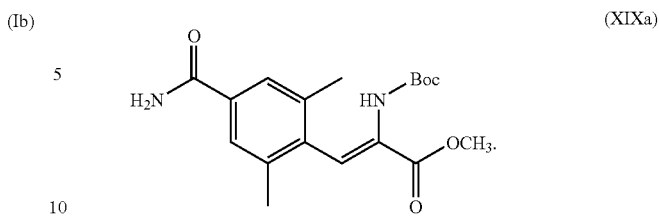

(XIXa)

The compounds of formula (XIX) are useful as intermediates in the synthesis of compounds of formula (II).

The present invention is further directed to processes for the preparation of compound of formula (II)

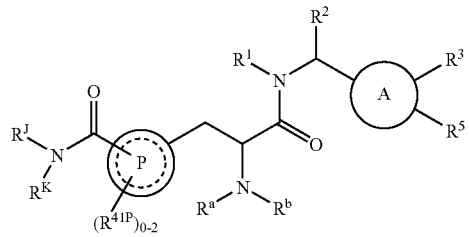

(II)

wherein

$R^J$, $R^K$, $R^{41P}$, $R^a$, $R^b$, $R^1$, $R^2$, $R^3$, $R^5$, and

are as herein defined. The compounds of the present invention are opioid receptor modulators, useful in the treatment of disorders mediated by at least one opioid receptor (preferably δ or μ opioid receptor), including, but not limited to pain and gastrointestinal disorders.

Embodiments of the present invention include processes for the preparation of compounds wherein $R^1$ is selected from the group consisting of hydrogen, $C_{1-6}$alkyl, aryl($C_{1-4}$)alkyl, and heteroaryl($C_{1-4}$)alkyl; wherein the aryl and heteroaryl portion of aryl($C_{1-4}$)alkyl and heteroaryl($C_{1-4}$)alkyl are optionally substituted with one to three $R^{11}$ substituents independently selected from the group consisting of $C_{1-6}$alkoxy; heteroaryl optionally substituted with one to two substituents independently selected from the group consisting of $C_{1-4}$alkyl, $C_{1-4}$alkoxy, and carboxy; carboxy; $C_{1-4}$alkoxycarbonyl; $C_{1-4}$alkoxycarbonyloxy; aminocarbonyl; $C_{1-4}$alkylaminocarbonyl; $C_{3-6}$cycloalkylaminocarbonyl; hydroxy($C_{1-6}$)alkylaminocarbonyl; $C_{6-10}$arylaminocarbonyl wherein $C_{6-10}$aryl is optionally substituted with carboxy or $C_{1-4}$alkoxycarbonyl; heterocyclylcarbonyl; cyano; halogen; trifluoromethoxy; and hydroxy; provided that no more than one $R^{11}$ is heteroaryl (optionally substituted with one to two $C_{1-4}$alkyl substituents); $C_{6-10}$arylaminocarbonyl wherein $C_{6-10}$aryl is optionally substituted with carboxy or $C_{1-4}$alkoxycarbonyl; or heterocyclylcarbonyl.

Embodiments of the present invention further include processes for the preparation of compounds wherein $R^1$ is selected from the group consisting of $C_{6-10}$aryl($C_{1-4}$)alkyl, pyridinyl($C_{1-4}$)alkyl, and furanyl($C_{1-4}$)alkyl; wherein $C_{6-10}$aryl, pyridinyl, and furanyl are optionally substituted with one to three $R^{11}$ substituents independently selected from the group consisting of $C_{1-3}$alkoxy; tetrazolyl; carboxy; $C_{1-4}$alkoxycarbonyl; aminocarbonyl; $C_{1-4}$alkylaminocarbonyl; $C_{3-6}$cycloalkylaminocarbonyl; hydroxy($C_{1-4}$)alkylaminocarbonyl; $C_{6-10}$arylaminocarbonyl wherein $C_{6-10}$aryl is optionally substituted with carboxy or $C_{1-4}$alkoxycarbonyl; morpholin-4-ylcarbonyl; cyano; halogen; and trifluoromethoxy; provided that that no more than one $R^{11}$ is $C_{6-10}$arylaminocarbonyl.

Embodiments of the present invention further include processes for the preparation of compounds wherein $R^1$ is selected from the group consisting of phenyl($C_{1-3}$)alkyl, pyridinyl($C_{1-3}$)alkyl, and furanyl($C_{1-3}$)alkyl; wherein phenyl, pyridinyl, and furanyl are optionally substituted with one to three $R^{11}$ substituents independently selected from the group consisting of $C_{1-3}$alkoxy; tetrazolyl, $C_{3-6}$cycloalkylaminocarbonyl; hydroxy($C_{1-4}$)alkylaminocarbonyl; $C_{6-10}$arylaminocarbonyl wherein $C_{6-10}$aryl is optionally substituted with carboxy or $C_{1-4}$alkoxycarbonyl; morpholin-4-ylcarbonyl; chloro; fluoro; trifluoromethoxy; $C_{1-4}$alkoxycarbonyl; and carboxy; provided that that no more than one $R^{11}$ is $C_{6-10}$arylaminocarbonyl.

Embodiments of the present invention further include processes for the preparation of compounds wherein $R^1$ is phenylmethyl, pyridinylmethyl, or furanylmethyl; wherein phenyl, pyridinyl, and furanyl are optionally substituted with one to three $R^{11}$ substituents independently selected from the group consisting of methoxy; tetrazolyl; cyclopropylaminocarbonyl; (2-hydroxyeth-1-yl)aminocarbonyl; methoxycarbonyl; phenylaminocarbonyl wherein phenyl is optionally substituted with carboxy; morpholin-4-ylcarbonyl; and carboxy; provided that that no more than one $R^{11}$ is phenylaminocarbonyl.

Embodiments of the present invention include processes for the preparation of compounds wherein $R^2$ is a substituent selected from the group consisting of hydrogen, $C_{1-4}$alkyl, hydroxy($C_{1-4}$)alkyl, and phenyl($C_{1-6}$)alkoxy($C_{1-4}$)alkyl; wherein said phenyl is optionally substituted with one to two substituents independently selected from the group consisting of $C_{1-3}$alkyl, $C_{1-3}$alkoxy, hydroxy, cyano, fluoro, chloro, bromo, trifluoromethyl, and trifluoromethoxy.

Embodiments of the present invention further include processes for the preparation of compounds wherein $R^2$ is selected from the group consisting of hydrogen and $C_{1-4}$alkyl. Embodiments of the present invention further include processes for the preparation of those compounds wherein $R^2$ is hydrogen or methyl.

Embodiments of the present invention include processes for the preparation of compounds wherein ring A is a-1. Embodiments of the present invention further include processes for the preparation of compounds wherein A-B of ring a-1 is N—C.

Embodiments of the present invention include processes for the preparation of compounds wherein $R^3$ is one to two substituents independently selected from the group consisting of $C_{1-6}$alkyl, halogen, and aryl; wherein aryl is optionally substituted with one to three substituents independently selected from the group consisting of halogen, carboxy, aminocarbonyl, $C_{1-3}$alkylsulfonylamino, cyano, hydroxy, amino, $C_{1-3}$alkylamino, and ($C_{1-3}$alkyl)$_2$amino.

Embodiments of the present invention further include processes for the preparation of compounds wherein $R^3$ is one to two substituents independently selected from the group consisting of $C_{1-3}$alkyl, bromo, and phenyl; wherein phenyl is optionally substituted with one to three substituents independently selected from the group consisting of chloro, fluoro, carboxy, aminocarbonyl, and cyano.

Embodiments of the present invention further include processes for the preparation of compounds wherein $R^3$ is one to two substituents independently selected from the group consisting of methyl and phenyl; wherein phenyl is optionally substituted with one to three substituents independently selected from the group consisting of chloro and carboxy.

Embodiments of the present invention further include processes for the preparation of compounds wherein at least one $R^3$ substituent is phenyl.

Embodiments of the present invention further include processes for the preparation of compounds wherein $R^3$ is a substituent selected from the group consisting of methyl and phenyl; wherein phenyl is optionally substituted with one to two substituents independently selected from the group consisting of chloro and carboxy.

Embodiments of the present invention include processes for the preparation of compounds wherein

is $C_{6-10}$aryl. Embodiments of the present invention further include processes for the preparation of compounds wherein

is phenyl.

Embodiments of the present invention include processes for the preparation of compounds wherein $R^{41P}$ is selected from $C_{1-3}$alkyl, $C_{1-6}$alkoxy or fluoro. Embodiments of the present invention further include processes for the preparation of compounds wherein $R^{41P}$ is selected from $C_{1-3}$alkyl or $C_{1-3}$alkoxy. Embodiments of the present invention further include processes for the preparation of compounds wherein $R^{41P}$ is selected from methyl, ethyl, methoxy, ethoxy or fluoro. Embodiments of the present invention further include processes for the preparation of compounds wherein $R^{41P}$ is selected from methyl or methoxy.

Embodiments of the present invention include processes for the preparation of compounds wherein $R^5$ is hydrogen or methyl. Embodiments of the present invention further include processes for the preparation of compounds wherein $R^5$ is hydrogen.

Embodiments of the present invention include processes for the preparation of compounds wherein $R^a$ and $R^b$ are independently selected from the group consisting of hydrogen and $C_{1-3}$alkyl; or, when $R^a$ and $R^b$ are each other than hydrogen, $R^a$ and $R^b$ are optionally taken together with the nitrogen atom to which they are both attached to form a five to seven membered monocyclic ring. Embodiments of the present invention further include processes for the preparation of compounds wherein $R^a$ and $R^b$ are independently hydrogen or methyl. Embodiments of the present invention further include processes for the preparation of compounds wherein $R^a$ and $R^b$ are each hydrogen.

Embodiments of the present invention include processes for the preparation of compounds of formula (I) wherein the stereo-center denoted with a "*" as shown below,

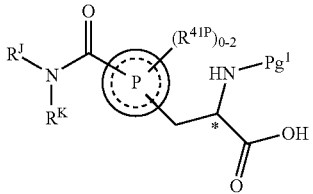

(I)

is in the S-configuration. In another embodiment are processes for the preparation of compounds of formula (I) wherein the stereo-center denoted with a "*" on the compound of formula (I) is in the R-configuration.

Embodiments of the present invention include processes for the preparation of compounds of formula (II) that are present in their RR, SS, RS, or SR configuration. Embodiments of the present invention further include processes for the preparation of compounds of formula (II) that are present in their S,S configuration.

Embodiments of the present invention include processes for the preparation of compounds of formula (IIe)

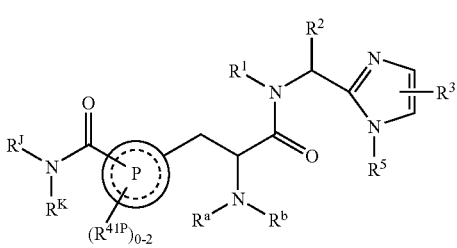

(IIe)

wherein:
$R^1$ is selected from the group consisting of hydrogen, $C_{1-6}$alkyl, aryl($C_{1-4}$)alkyl, and heteroaryl($C_{1-4}$)alkyl;
  wherein the aryl and heteroaryl portion of aryl($C_{1-4}$)alkyl and heteroaryl($C_{1-4}$)alkyl are optionally substituted with one to three $R^{11}$ substituents independently selected from the group consisting of $C_{1-6}$alkoxy; heteroaryl optionally substituted with one to two substituents independently selected from the group consisting of $C_{1-4}$alkyl, $C_{1-4}$alkoxy, and carboxy; carboxy; $C_{1-4}$alkoxycarbonyloxy; $C_{1-4}$alkoxycarbonyl; aminocarbonyl; $C_{1-4}$alkylaminocarbonyl; $C_{3-6}$cycloalkylaminocarbonyl; hydroxy($C_{1-6}$)alkylaminocarbonyl; $C_{6-10}$arylaminocarbonyl wherein $C_{6-10}$aryl is optionally substituted with carboxy or $C_{1-4}$alkoxycarbonyl; heterocyclylcarbonyl; cyano; halogen; trifluoromethoxy; and hydroxy; provided that no more than one $R^{11}$ is heteroaryl (optionally substituted with one to two $C_{1-4}$alkyl substituents); $C_{6-10}$arylaminocarbonyl wherein $C_{6-10}$aryl is optionally substituted with carboxy or $C_{1-4}$alkoxycarbonyl; or heterocyclylcarbonyl;
$R^2$ is selected from the group consisting of hydrogen, $C_{1-4}$alkyl, hydroxy($C_{1-4}$)alkyl, and phenyl($C_{1-6}$)alkoxy($C_{1-4}$)alkyl;
  wherein said phenyl is optionally substituted with one to two substituents independently selected from the group consisting of $C_{1-3}$alkyl, $C_{1-3}$alkoxy, hydroxy, cyano, fluorine, chlorine, bromine, trifluoromethyl, and trifluoromethoxy;
$R^3$ is one to two substituents independently selected from the group consisting of $C_{1-6}$alkyl, halogen, and aryl; wherein aryl is optionally substituted with one to three substituents independently selected from the group consisting of halogen, carboxy, aminocarbonyl, $C_{1-3}$alkylsulfonylamino, cyano, hydroxy, amino, $C_{1-3}$alkylamino, and ($C_{1-3}$alkyl)$_2$amino;
$R^5$ is hydrogen or methyl;
$R^a$ and $R^b$ are independently hydrogen or $C_{1-3}$alkyl; or, when $R^a$ and $R^b$ are each other than hydrogen, $R^a$ and $R^b$ are optionally taken together with the nitrogen atom to which they are both attached to form a five to seven membered monocyclic ring;

is $C_{6-10}$aryl;
$R^{41P}$ is selected from $C_{1-3}$alkyl, $C_{1-6}$alkoxy or fluoro;
$R^J$ and $R^K$ are each independently selected from hydrogen or $C_{1-4}$alkyl; alternatively, $R^J$ and $R^K$ are taken together with the nitrogen atom to which they are bound to form a five to seven membered heterocyclyl;
  and pharmaceutically acceptable enantiomers, diastereomers, racemates, and salts thereof.

Embodiments of the present invention further include processes for the preparation of compounds of formula (IIe) wherein $R^1$ is selected from the group consisting of $C_{6-10}$aryl($C_{1-4}$)alkyl, pyridinyl($C_{1-4}$)alkyl, and furanyl($C_{1-4}$)alkyl; wherein $C_{6-10}$aryl, pyridinyl, and furanyl are optionally substituted with one to three $R^{11}$ substituents independently selected from the group consisting of $C_{1-3}$alkoxy; tetrazolyl; carboxy; $C_{1-3}$alkoxycarbonyl; aminocarbonyl; $C_{1-4}$alkylaminocarbonyl; $C_{1-3}$alkylaminocarbonyl; $C_{3-6}$cycloalkylaminocarbonyl; hydroxy($C_{1-4}$)alkylaminocarbonyl; $C_{6-10}$arylaminocarbonyl wherein $C_{6-10}$aryl is optionally substituted with carboxy or $C_{1-4}$alkoxycarbonyl; morpholin-4-ylcarbonyl; cyano; halogen; and trifluoromethoxy; provided that no more than one $R^{11}$ is $C_{6-10}$arylaminocarbonyl;
$R^2$ is hydrogen or $C_{1-4}$alkyl;
$R^3$ is one to two substituents independently selected from the group consisting of $C_{1-3}$alkyl, bromo, and phenyl; wherein phenyl is optionally substituted with one to three substituents independently selected from the group consisting of chloro, fluoro, carboxy, aminocarbonyl, and cyano;
$R^5$ is hydrogen;
$R^a$ and $R^b$ are independently hydrogen or methyl;

is $C_{6-10}$aryl;
$R^{41P}$ is selected from $C_{1-3}$alkyl or $C_{1-6}$alkoxy;
$R^J$ and $R^K$ are each independently selected from hydrogen or $C_{1-4}$alkyl;
  and pharmaceutically acceptable enantiomers, diastereomers, racemates, and salts thereof.

Embodiments of the present invention further include processes for the preparation of compounds of formula (IIe) wherein $R^1$ is selected from the group consisting of phenyl($C_{1-3}$)alkyl, pyridinyl($C_{1-3}$)alkyl, and furanyl($C_{1-3}$)alkyl; wherein phenyl, pyridinyl, and furanyl are optionally substituted with one to three $R^{11}$ substituents independently selected from the group consisting of $C_{1-3}$alkoxy; tetrazolyl; $C_{3-6}$cycloalkylaminocarbonyl; hydroxy($C_{1-4}$)alkylaminocarbonyl; $C_{6-10}$arylaminocarbonyl wherein $C_{6-10}$aryl is optionally substituted with carboxy or $C_{1-4}$alkoxycarbonyl; morpholin-4-ylcarbonyl; chloro; fluoro; trifluoromethoxy; and carboxy;

$R^2$ is hydrogen or methyl;

$R^3$ is one to two substituents independently selected from the group consisting of methyl and phenyl; wherein phenyl is optionally substituted with one to three substituents independently selected from the group consisting of chloro and carboxy;

$R^5$ is hydrogen;

$R^a$ and $R^b$ are each hydrogen;

is phenyl;

$R^{41P}$ is selected from methyl, ethyl, methoxy, ethoxy or fluoro.

$R^J$ and $R^K$ are each independently selected from hydrogen or $C_{1-3}$alkyl;

and pharmaceutically acceptable enantiomers, diastereomers, racemates, and salts thereof.

Additional embodiments of the present invention, include processes for the preparation of compounds wherein the substituents for one or more of the variables defined herein (i.e.

$R^J$, $R^K$, $R^{41P}$, $Pg^1$ etc.) are independently selected to be any individual substituent or any subset of substituents selected from the complete list as defined herein.

As used herein, unless otherwise noted, "alkyl" whether used alone or as part of a substituent group refers to straight and branched carbon chains having 1 to 8 carbon atoms or any number within this range. The term "alkoxy" refers to an —Oalkyl substituent group, wherein alkyl is as defined supra. Similarly, the terms "alkenyl" and "alkynyl" refer to straight and branched carbon chains having 2 to 8 carbon atoms or any number within this range, wherein an alkenyl chain has at least one double bond in the chain and an alkynyl chain has at least one triple bond in the chain. An alkyl and alkoxy chain may be substituted on a carbon atom. In substituent groups with multiple alkyl groups such as ($C_{1-6}$alkyl)$_2$amino- the $C_{1-6}$alkyl groups of the dialkylamino may be the same or different.

The term "cycloalkyl" refers to saturated or partially unsaturated, moncyclic or polycyclic hydrocarbon rings of from 3 to 14 carbon atom members. Examples of such rings include, and are not limited to cyclopropyl, cyclobutyl, cyclopentyl, cyclohexyl, cycloheptyl and adamantyl. Alternatively, the cycloalkyl ring may be fused to a benzene ring (benzo fused cycloalkyl), a 5 or 6 membered heteroaryl ring (containing one of O, S or N and, optionally, one additional nitrogen) to form a heteroaryl fused cycloalkyl.

The term "heterocyclyl" refers to a nonaromatic cyclic ring of 5 to 7 members in which 1 to 2 members are nitrogen, or a nonaromatic cyclic ring of 5 to 7 members in which zero, one or two members are nitrogen and up to two members are oxygen or sulfur; wherein, optionally, the ring contains zero to one unsaturated bonds, and, optionally, when the ring is of 6 or 7 members, it contains up to two unsaturated bonds. The term heterocyclyl includes 5 to 7 membered monocycle wherein the heterocyclyl may be fused to a benzene ring (benzo fused heterocyclyl), a 5 or 6 membered heteroaryl ring (containing one of O, S or N and, optionally, one additional nitrogen), a 5 to 7 membered cycloalkyl or cycloalkenyl ring, a 5 to 7 membered heterocyclyl ring (of the same definition as above but absent the option of a further fused ring) or fused with the carbon of attachment of a cycloalkyl, cycloalkenyl or heterocyclyl ring to form a spiro moiety. For instant compounds of the invention, the carbon atom ring members that form the heterocyclyl ring are fully saturated. Other compounds of the invention may have a partially saturated heterocyclyl ring. The term heterocyclyl include a 5 to 7 membered moncyclic ring bridged to form bicyclic rings. Such compounds are not considered to be fully aromatic and are not referred to as heteroaryl compounds. Examples of heterocyclyl groups include, and are not limited to, pyrrolinyl (including 2H-pyrrole, 2-pyrrolinyl or 3-pyrrolinyl), pyrrolidinyl, 2-imidazolinyl, imidazolidinyl, 2-pyrazolinyl, pyrazolidinyl, piperidinyl, morpholinyl, thiomorpholinyl and piperazinyl.

The term "aryl" refers to an unsaturated, aromatic monocyclic ring of 6 carbon members or to an unsaturated, aromatic polycyclic ring of from 10 to 14 carbon members. Examples of such aryl rings include, and are not limited to, phenyl, naphthalenyl or anthracenyl. Preferred aryl groups for the practice of this invention are phenyl and naphthalenyl.

The term "heteroaryl" refers to an aromatic ring of 5 or 6 members wherein the ring consists of carbon atoms and has at least one heteroatom member. Suitable heteroatoms include nitrogen, oxygen or sulfur. In the case of 5 membered rings, the heteroaryl ring contains one member of nitrogen, oxygen or sulfur and, in addition, may contain up to three additional nitrogens. In the case of 6 membered rings, the heteroaryl ring may contain from one to three nitrogen atoms. For the case wherein the 6 membered ring has three nitrogens, at most two nitrogen atoms are adjacent. Optionally, the heteroaryl ring is fused to a benzene ring (benzo fused heteroaryl), a. 5 or 6 membered heteroaryl ring (containing one of O, S or N and, optionally, one additional nitrogen), a 5 to 7 membered cycloalkyl ring or a 5 to 7 membered heterocyclo ring (as defined supra but absent the option of a further fused ring). Examples of heteroaryl groups include, and are not limited to, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl or pyrazinyl; fused heteroaryl groups include indolyl, isoindolyl, indolinyl, benzofuryl, benzothienyl, indazolyl, benzimidazolyl, benzthiazolyl, benzoxazolyl, benzisoxazolyl, benzothiadiazolyl, benzotriazolyl, quinolizinyl, quinolinyl, isoquinolinyl or quinazolinyl.

The term "arylalkyl" means an alkyl group substituted with an aryl group (e.g., benzyl, phenethyl). Similarly, the term "arylalkoxy" indicates an alkoxy group substituted with an aryl group (e.g., benzyloxy).

The term "halogen" refers to fluorine, chlorine, bromine and iodine.

Substituents that are substituted with multiple halogens are substituted in a manner that provides compounds, which are stable.

Whenever the term "alkyl" or "aryl" or either of their prefix roots appear in a name of a substituent (e.g., arylalkyl, alkylamino) it shall be interpreted as including those limitations given above for "alkyl" and "aryl." Designated numbers of carbon atoms (e.g., $C_1$-$C_6$) shall refer independently to the number of carbon atoms in an alkyl moiety or to the alkyl portion of a larger substituent in which alkyl appears as its prefix root. For alkyl, and alkoxy substituents the designated number of carbon atoms includes all of the independent members included in the range specified individually and all the combination of ranges within in the range specified. For example $C_{1-6}$ alkyl would include methyl, ethyl, propyl, butyl, pentyl and hexyl individually as well-as sub-combinations thereof (e.g. $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

An "independently" selected substituent-refers to a group of substituents, wherein the substituents may be different. Therefore, designated numbers of carbon atoms (e.g. $C_{1-8}$) shall refer independently to the number of carbon atoms in an alkyl or cycloalkyl moiety or to the alkyl portion of a larger substituent in which alkyl appears as its prefix root.

Under standard nomenclature used throughout this disclosure, the terminal portion of the designated side chain is described first, followed by the adjacent functionality toward the point of attachment. Thus, for example, a "phenyl-($C_{1-6}$alkyl)amino-carbonyl-($C_{1-6}$alkyl)" substituent refers to a group of the formula

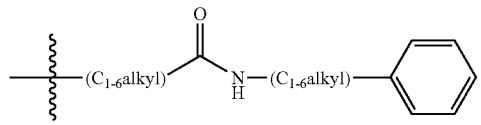

Abbreviations used in the specification, particularly the Schemes and Examples, are as follows:

| | |
|---|---|
| Ac = | Acetyl group (—C(O)—CH$_3$) |
| Ac$_2$O = | Acetic anhydride |
| Cbz or CBZ = | Benzyloxy-carbonyl- |
| Cpd = | Compound |
| DBU = | 1,8-Diazabicyclo[5.4.0]undec-7-ene |
| DCM = | Dichloromethane |
| DIPEA or DIEA = | Diisopropylethylamine |
| DMF = | N,N-Dimethylformamide |
| DPPE = | 1,2-Bis(diphenylphosphino)ethane |
| DPPF = | 1,1'-Bis(diphenylphosphino)ferrocene |
| DPPP = | 1,3-Bis(diphenylphosphino)propane |
| EDCI or EDC = | 1-(3-dimethylaminopropyl)-3-ethylcarbodiimide hydrochloride |
| Et$_2$O = | Diethyl ether |
| EtOAc = | Ethyl acetate |
| Fmoc = | 9-fluorenyl-methoxy-carbonyl- |
| HOAc = | Acetic acid |
| HOBT = | 1-Hydroxybenzotriazole |
| Me | Methyl |
| MeOH = | Methanol |
| MeO = | Methoxy |
| MTBE = | Methyl-tert-butyl ether |
| NaBH(OAc)$_3$ = | Sodium triacetoxybrohydride |
| Pd-C = | Palladium on Carbon Catalyst |
| Pd$_2$(OAc)$_2$ = | Palladium(II)acetate |
| Pd$_2$(dba)$_3$ = | Tris(dibenzylidene acetone)dipalladium(0) |
| Pd(PPh$_3$)$_4$ = | Tetrakis(triphenylphosphine)palladium (0) |
| Ph = | Phenyl |
| P(Ph)$_3$ = | Triphenylphosphine |
| PyBop = | Benzotriazol-1-yloxy-tris(pyrrolidino)phosphonium hexafluorophosphate |
| PyBrop = | Bromotri(pyrrolidino)phsophonium hexafluorophosphate |
| [Rh(cod)(R,R- | (R,R)-(—)-Bis[(o- |
| DIPAMP)]$^+$BF$_4^-$ | methoxyphenyl)(phenyl)phosphino]ethane(1,5-cyclo-octadiene)rhodium (I) tetrafluoroborate |
| rt or RT = | Room temperature |
| t-BOC or Boc = | tert-Butoxycarbonyl |
| TEA = | Triethylamine |
| Tf = | Trifluoromethyl-sulfonyl-(—SO$_2$—CF$_3$) |
| TFA = | Trifluoroacetic acid |
| THF = | Tetrahydrofuran |
| Tyr = | Tyrosine |

As used herein, the term "pain" shall include centrally mediated pain, peripherally mediated pain, structural or soft tissue injury related pain, pain related to inflammation, progressive disease related pain, neuropathic pain, acute pain and chronic pain. Further, the term "chronic pain" shall include neuropathic pain conditions, diabetic peripheral neuropathy, post-herpetic neuralgia, trigeminal neuralgia, post-stroke pain syndromes and cluster or migraine headaches.

As used herein, the term "gastrointestinal disorder" shall include diarrheic syndromes, motility disorders such as diarrhea-predominant, constipation-predominant, alternating irritable bowel syndrome, post-operative ileus and constipation, and inflammatory bowel disease. Further, the term "inflammatory bowel disease" shall include ulcerative colitis and Crohn's disease.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the term "aprotic solvent" shall mean any solvent that does not yield a proton. Suitable examples include, but are not limited to DMF, dioxane, THF, acetonitrile, pyridine, dichloroethane, dichloromethane, MTBE, toluene, and the like.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-b-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene &, P. G. M. Wuts, *Protective Groups in Organic Synthesis*, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

For use in medicine, the salts of the compounds of this invention refer to nontoxic pharmaceutically acceptable salts.

The present invention is directed to processes for the preparation of compounds of formula (I) as outlined in Scheme 1 below.

STEP 1: Preparation of Compounds of Formula (XII), wherein X is —OH and Y is Selected from Br or Cl

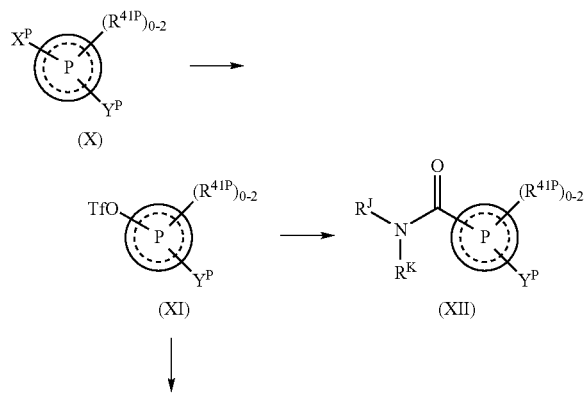

STEP 1: Preparation of Compounds of Formula (XII), wherein X is —OC(O)—$C_{1-4}$alkyl and Y is Selected from Br, Cl or I

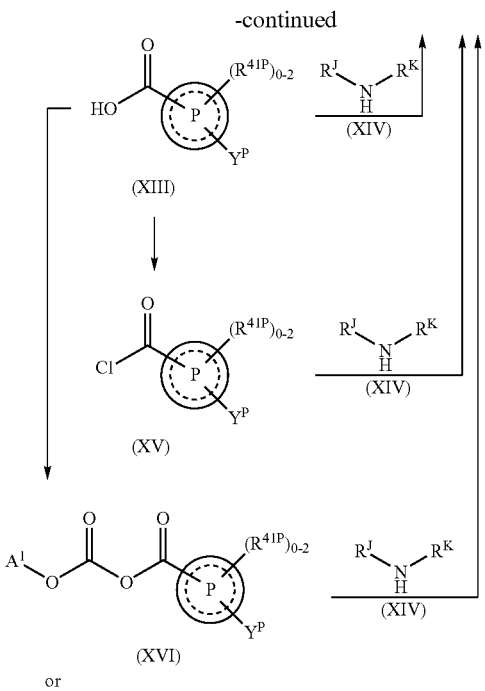

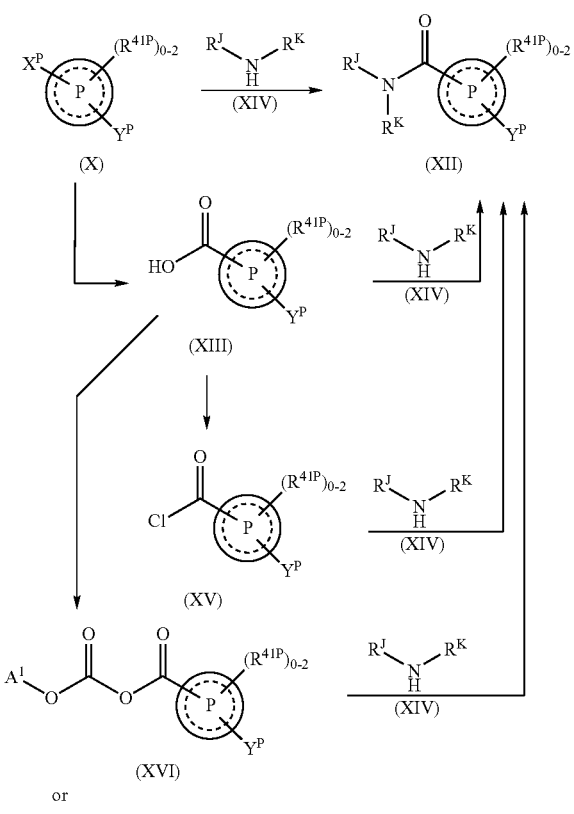

STEP 1: Preparation of Compounds of Formula (XII), wherein X is —CN and Y is Selected from Br, Cl or I

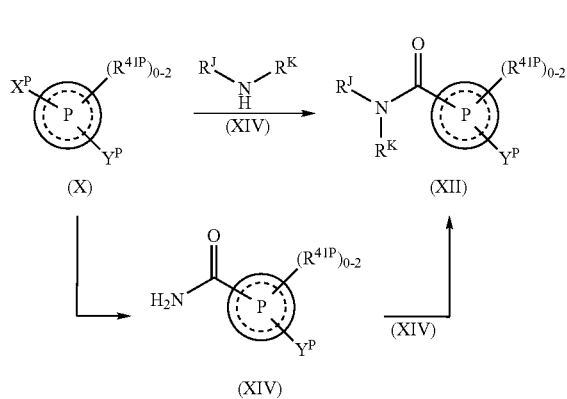

STEP 2: Preparation of Compound of Formula (XIX)

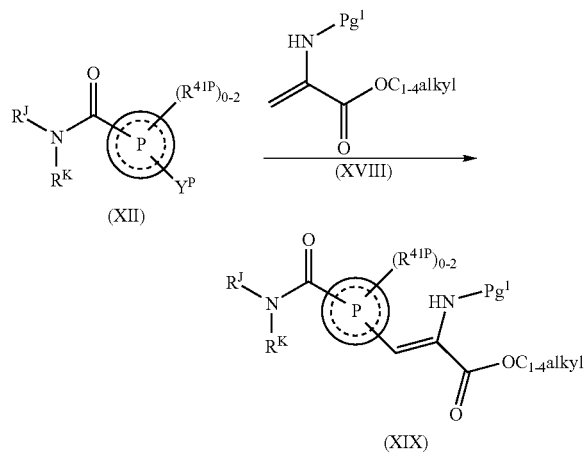

STEP 3: Preparation of Compounds of Formula (XX)

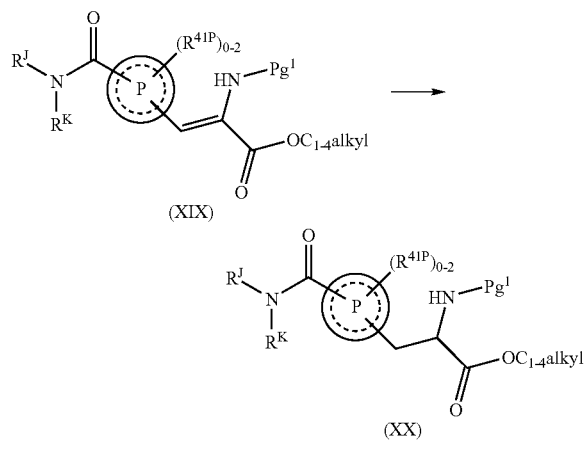

STEP 4: Preparation of Compounds of Formula (I)

Scheme 1

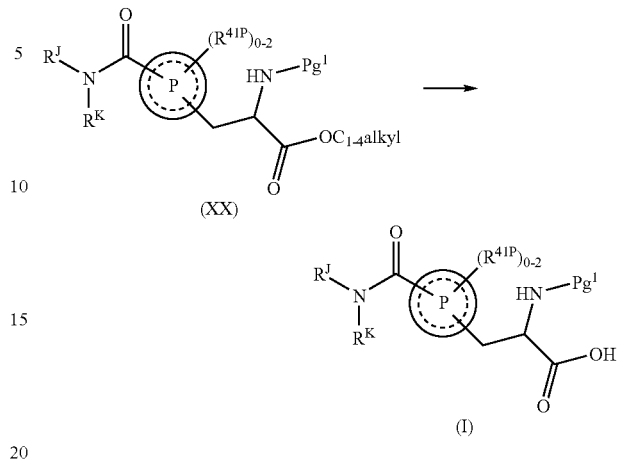

STEP 1: Wherein X is OH and Y is Selected from Br or Cl

Accordingly, a suitably substituted compound of formula (X), wherein $X^P$ is OH and wherein $Y^P$ is Br or Cl, preferably $Y^P$ is Br, a known compound or compound prepared by known methods; is reacted with a tritlating reagent such as triflic anhydride, N-phenyltrifluoromethanesulfonimide, and the like; in the presence of an organic or inorganic base such as pyridine, TEA, DIPEA, $K_3PO_4$, $K_2CO_3$, and the like; optionally in an organic solvent such as DCM, chloroform, THF, and the like; to yield the corresponding compound of formula (XI).

The compound of formula (XI) is reacted with carbon monoxide or a source of carbon monoxide such as $Ac_2O$ in combination with HCOONa (see for example, S. Cacchi, G. Fabrizi, A. Goggiamani, Org. Lett. (2003), 5(23), pp 4269-4272) and a suitably substituted amine, a compound of formula $NR^JR^K$ (a compound of formula (XIV)) or when $R^J$ and $R^K$ are each hydrogen, with a suitable source of ammonia such as HMDS, ammonia gas, and the like; in the presence of a palladium catalyst such $PdCl_2$, $Pd_2(OAc)_2$, and the like, in combination with a suitable ligand, such DPPP, DPPF, $P(Ph)_3$, and the like; or in the presence of a palladium:ligand complex such as $Pd(PPh_3)_4$, and the like; in an organic solvent such as DMF, THF, dioxane, and the like, preferably DMF; at a temperature in the range of from about 50° C. to about 160° C., preferably at a temperature in the range of from about 60° C. to about 120° C.; to yield the corresponding compound of formula (XII).

Alternatively, the compound of formula (XI) is reacted with carbon monoxide or a source of carbon monoxide such as $Ac_2O$ in combination with HCOONa (see for example, S. Cacchi, G. Fabrizi, A. Goggiamani, Org. Lett. (2003), 5(23), pp 4269-4272); in the presence of an inorganic base such as $K_2CO_3$, $Na_2CO_3$, and the like, in an organic solvent such as DMF, dioxane, THF, and the like; at a temperature in the range of from about 50° C. to about 160° C., preferably at a temperature in the range of from about 60° C. to about 80° C.; to yield the corresponding compound of formula (XIII).

The compound of formula (XIII) is reacted with a suitably substituted compound of formula (XIV), a known compound or compound prepared by known methods, or when $R^J$ and $R^K$ are each hydrogen, with a suitable source of ammonia such as HMDS, ammonia gas, and the like, preferably HMDS; in the presence of a coupling agent such as EDCl, HOBT, PyBop, PyBrop, and the like; preferably in the presence of an organic base such as TEA, DIPEA, pyridine, the like, or an amount of the compound of formula (XIV) or source of ammonia sufficient to act as the base, preferably greater than about 2 equivalents; in an organic solvent such as THF, dioxane, DMF, and the like; to yield the corresponding compound of formula (XII).

Alternatively, the compound of formula (XI) is reacted with carbon monoxide or a source of carbon monoxide such as $Ac_2O$ in combination with HCOONa (see for example, S. Cacchi, G. Fabrizi, A. Goggiamani, Org. Lett. (2003), 5(23), pp 4269-4272); in the presence of an inorganic base such as $K_2CO_3$, $Na_2CO_3$, and the like, in an organic solvent such as DMF, dioxane, THF, and the like; at a temperature in the range of from about 50° C. to about 160° C., preferably at a temperature in the range of from about 60° C. to about 80° C; to yield the corresponding compound of formula (XIII).

The compound of formula (XIII) is reacted with a suitably source of chlorine such as thionyl chloride, $PCl_3$, $PCl_5$, oxalyl chloride, oxalyl chloride in DMF, and the like; in an organic solvent such as DCM, chloroform, and the like, preferably at a temperature greater than about room temperature, more preferably at a temperature in the range of about 35° C. to about 60° C.; to yield the corresponding compound of formula (XV).

The compound of formula (XV) is reacted with a suitably substituted compound of formula (XIV), a known compound or compound prepared by known methods, or when $R^J$ and $R^K$ are each hydrogen, with a suitable source of ammonia such as ammonium chloride, $NH_4OH$, HMDS, ammonia gas, and the like, preferably ammonium chloride; preferably in the presence of an organic base such as TEA, DIPEA, pyridine, the like, or an amount of the compound of formula (XIV) or source of ammonia sufficient to act as the base, preferably greater than about 2 equivalents; in an organic solvent such as THF, dioxane, DMF, and the like; to yield the corresponding compound of formula (XII).

Alternatively, the compound of formula (XIII) is reacted with $C_{1-4}$alkyl-chloroformate, preferably, methylchloroformate; in the presence of a organic base such as TEA, DIPEA, pyridine and the like; preferably at a temperature less than about room temperature, more preferably at a temperature in the range of from about 0° C.; in an organic solvent such as DMF, DCM, chloroform, THF, and the like; to yield the corresponding compound of formula (XVI) wherein $A^1$ is the corresponding $C_{1-4}$alkyl, preferably methyl.

The compound of formula (XVI) is reacted with a suitably substituted compound of formula (XIV) or when $R^J$ and $R^K$ are each hydrogen, with a suitable source of ammonia such as $NH_4OH$, HMDS, ammonia gas, and the like, preferably $NH_4OH$; in the presence of a palladium catalyst such $PdCl_2$, $Pd_2(OAc)_2$, and the like, in combination with a suitable ligand, such DPPP, DPPF, $P(Ph)_3$, and the like; or in the presence of a palladium:ligand complex such as $Pd(PPh_3)_4$, and the like; at a temperature in the range of from about 50° C. to about 160° C., preferably at a temperature in the range of from about 60° C. to about 80° C.; to yield the corresponding compound of formula (XII).

One skilled in the art will further recognize that the compound of formula (XI) may be reacted according to known methods, to yield the corresponding compound of formula (X) wherein $X^P$ is —C(O)—$OC_{1-4}$alkyl or CN.

STEP 1: Wherein X is —C(O)—$OC_{1-4}$alkyl and wherein $Y^P$ is Br, Cl or I

Alternatively, a suitably substituted compound of formula (X), wherein $X^P$ is —C(O)—$OC_{1-4}$alkyl and wherein $Y^P$ is selected from Br, Cl or I, a known compound or compound prepared by known methods, is reacted with a suitably substituted compound of formula (XIV), a known compound or compound prepared by known methods, or when $R^J$ and $R^K$ are each hydrogen, with a suitable source of ammonia such as $NH_4OH$, HMDS, ammonia gas, and the like; at a temperature greater than room temperature, preferably at about reflux temperature; to yield the corresponding compound of formula (XII).

Alternatively, a suitably substituted compound of formula (X), wherein $X^P$ is —C(O)—$OC_{1-4}$alkyl and wherein $Y^P$ is selected from Br, Cl or I, a known compound or compound prepared by known methods, is reacted with a suitably substituted compound of formula (XIV), a known compound or compound prepared by known methods, or when $R^J$ and $R^K$ are each hydrogen, with a suitable source of ammonia such as $NH_4OH$, HMDS, ammonia gas, and the like; in the presence of an activating agent such as trimethylaluminum, triisopropylaluminum, and the like; in an aprotic organic solvent such as THF, dioxane, toluene, DCM, and the like; preferably at a temperature in the range of about 0° C. to about reflux temperature; to yield the corresponding compound of formula (XII).

Alternatively, a suitably substituted compound of formula (X), wherein $X^P$ is —C(O)—$OC_{1-4}$alkyl and wherein $Y^P$ is selected from Br, Cl or I, a known compound or compound prepared by known methods, is hydrolyzed according to known methods, for example by reacting with a base such as NaOH, LiOH, KOH, and the like, or by reacting with an acid such as HCl, $H_2SO_4$, and the like, preferably, the compound of formula (X) is reacted with an acid at a temperature greater than about room temperature, preferably at a temperature in the range of from about 60° to about 120° C., more preferably at a temperature of about 100° C.; to yield the corresponding compound of formula (XIII).

The compound of formula (XIII) is reacted with a suitably substituted compound of formula (XIV), a known compound or compound prepared by known methods, or when $R^J$ and $R^K$ are each hydrogen, with a suitable source of ammonia such as HMDS, ammonia gas, and the like, preferably HMDS; in the presence of a coupling agent such as EDCl, HOBT, PyBop, PyBrop, and the like; preferably in the presence of an organic base such as TEA, DIPEA, pyridine, the like, or in the presence of an amount of the compound of formula (XIV) or source of ammonia sufficient to act as the base, preferably greater than about 2 equivalents; in an organic solvent such as THF, dioxane, DMF, and the like, to yield the corresponding compound of formula (XII).

Alternatively, the compound of formula (X), wherein $X^P$ is —C(O)—$OC_{1-4}$alkyl and wherein $Y^P$ is selected from Br, Cl or I, a known compound or compound prepared by known methods, is reacted with carbon monoxide or a source of carbon monoxide such as $Ac_2O$ in combination with HCOONa (see for example, S. Cacchi, G. Fabrizi, A. Goggiamani, Org. Lett. (2003), 5(23), pp 4269-4272); in the presence of an inorganic base such as $K_2CO_3$, $Na_2CO_3$, and the like, in an organic solvent such as DMF, dioxane, THF, and the like; at a temperature in the range of from about 50° C. to about 160° C., preferably at a temperature in the range of from about 60° C. to about 80° C.; to yield the corresponding compound of formula (XIII).

The compound of formula (XIII) is reacted with a suitably source of chlorine such as thionyl chloride, $PCl_3$, $PCl_5$, oxalyl chloride, oxalyl chloride in DMF, and the like; in an organic solvent such as DCM, chloroform, and the like, preferably at a temperature greater than about room temperature, more preferably at a temperature in the range of about 35° C. to about 60° C., to yield the corresponding compound of formula (XV).

The compound of formula (XV) is reacted with a suitably substituted compound of formula (XIV), a known compound or compound prepared by known methods, or when $R^J$ and $R^K$ are each hydrogen, with a suitable source of ammonia such as ammonium chloride, $NH_4OH$, HMDS, ammonia gas, and the like, preferably ammonium chloride; preferably in the presence of an organic base such as TEA, DIPEA, pyridine, the like, or in the presence of an amount of the compound of formula (XIV) or source of ammonia sufficient to act as the base, preferably greater than about 2 equivalents; in an organic solvent such as THF, dioxane, DMF, and the like; to yield the corresponding compound of formula (XII).

Alternatively, the compound of formula (X), wherein $X^P$ is $-C(O)-OC_{1-4}$alkyl and wherein $Y^P$ is selected from Br, Cl or I, a known compound or compound prepared by known methods, is reacted with carbon monoxide or a source of carbon monoxide such as $Ac_2O$ in combination with HCOONa (see for example, S. Cacchi, G. Fabrizi, A. Goggiamani, Org. Lett. (2003), 5(23), pp 4269-4272); in the presence of an inorganic base such as $K_2CO_3$, $Na_2CO_3$, and the like, in an organic solvent such as DMF, dioxane, THF, and the like; at a temperature in the range of from about 50° C. to about 160° C., preferably at a temperature in the range of from about 60° C. to about 80° C.; to yield the corresponding compound of formula (XIII).

Alternatively, the compound of formula (XIII) is reacted with $C_{1-4}$alkyl-chloroformate, preferably, methylchloroformate; in the presence of a organic base such as TEA, DIPEA, pyridine and the like; preferably at a temperature less than about room temperature, more preferably at a temperature of about 0° C.; in an organic solvent such as DMF, DCM, chloroform, THF, and the like; to yield the corresponding compound of formula (XVI), wherein $A^1$ is the corresponding $C_{1-4}$alkyl, preferably methyl.

The compound of formula (XVI) is reacted with a suitably substituted compound of formula (XIV), a known compound or compound prepared by known methods, or when $R^J$ and $R^K$ are each hydrogen, with a suitable source of ammonia such as $NH_4OH$, HMDS, ammonia gas, and the like, preferably $NH_4OH$; in the presence of a palladium catalyst such $PdCl_2$, $Pd_2(OAc)_2$, and the like, in combination with a ligand, such DPPP, DPPF, $P(Ph)_3$, and the like; or in the presence of a palladium:ligand complex such as $Pd(PPh_3)_4$, and the like; at a temperature in the range of from about 50° C. to about 160° C., preferably at a temperature in the range of from about 60° C. to about 80° C.; to yield the corresponding compound of formula (XII).

STEP 1: Wherein X is $-CN$ and wherein $Y^P$ is Br, Cl or I

Alternatively, a suitably substituted compound of formula (X), wherein $X^P$ is CN and wherein $Y^P$ is selected from Br, Cl or I, a known compound or compound prepared by known methods, is reacted with a suitably substituted compound of formula (XIV), a known compound or compound prepared by known methods, according to known methods (for example as described in Parris, C. L., Org. Syn. Coll., (1973), 5, p 73; Lin, S., Synthesis, (April 1978), p. 330; Murahashi, S., Takeshi Naota, T., and Eiichiro Saito, E., JACS, (1986), 108 (24), p 7846), to yield the corresponding compound of formula (XII).

Alternatively, a suitably substituted compound of formula (X), wherein $X^P$ is CN and wherein $Y^P$ is selected from Br, Cl or I, a known compound or compound prepared by known methods, is reacted with an acid such as concentrated sulfuric acid, and the like; at a temperature greater than about room temperature, preferably at reflux temperature; to yield the corresponding compound of formula (XVI).

Alternatively, a suitably substituted compound of formula (X), wherein $X^P$ is CN and wherein $Y^P$ is selected from Br, Cl or I, a known compound or compound prepared by known methods, is reacted with an inorganic base such as NaOH, KOH, and the like; at a-temperature greater than about room temperature, preferably at about reflux temperature; to yield the corresponding compound of formula (XVI).

The compound of formula (XVI) is reacted according to known methods, for example, by alkylating in the presence of a base, to-yield the corresponding compound of formula (XII).

STEP 2:

The compound of formula (XII) is reacted with a suitably substituted compound of formula (XVII), wherein $Pg^1$ is a suitable nitrogen protecting group such as Boc, Cbz, Fmoc, acetyl, and the like, preferably $Pg^1$ is Boc, a known compound or compound prepared by known methods; in the presence of palladium catalyst such as $Pd_2(dba)_3$, $Pd(OAc)_2$, $PdCl_2$, and the like, preferably $Pd_2(dba)_3$; and preferably in the presence of a phosphorous ligand such as $P(o\text{-toluene})_3$, $P(Ph)_3$, $P(t\text{-butyl})_3$, DPPE, and the like, preferably $P(t\text{-butyl})_3$ or $P(o\text{-toluene})_3$; or in the presence of a palladium:ligand complex such as $Pd(PPh_3)_4$, and the like; in the presence of an organic or inorganic base such as dicyclohexylmethylamine, $Na_2CO_3$, $K_2CO_3$, TEA, DIPEA, pyridine, and the like, preferably TEA; in an organic solvent such as DMF, dioxane, and the like; at a temperature greater than about room temperature, preferably at a temperature in the range of about 60° C. to about 120° C.; to yield the corresponding compound of formula (XIX).

STEP 3:

The compound of formula (XIX) is hydrogenated according to known methods; for example by reacting with hydrogen or a source of hydrogen (such as cyclohexadiene, and the like); in the presence of a catalyst such as platinum oxide, palladium on carbon, nickel, $ClRh(PPh_3)_3$, $RuCl_2$, and the like, preferably palladium on carbon; in an organic solvent such as methanol, ethanol, THF, ethyl acetate, and the like, preferably methanol; at a temperature greater than room temperature, preferably at a temperature in the range of about 60° C. to about 120° C., to yield the corresponding compound of formula (XX).

One skilled in the art will recognize that the compound of formula (XIX) may be optionally reacted in the presence of a chiral catalyst, to yield the corresponding compound of formula (XX), wherein one stereo-isomer is present in an enantiomeric excess.

STEP 4:

The compound of formula (XX) is reacted with an aqueous base such as NaOH, LiOH, KOH, and the like; in an organic solvent such as methanol, THF, ethanol, and the like; to yield the corresponding compound of formula (I).

In an embodiment, the present invention is directed to processes for the preparation of compounds of formula (Ic).

In an embodiment, the present invention is directed to processes for the preparation of a compound of formula (Ib), a compound of formula (I) wherein

is phenyl; $R^J$ and $R^K$ are each hydrogen; the phenyl ring is further substituted with two $R^{41P}$ groups, which are each methyl and $Pg^1$ is Boc, also known as 2-tert-butoxycarbonylamino-3-(4-carbamoyl-2,6-dimethyl-phenyl)-propionic acid, as described in Scheme 1 above.

The present invention is further directed to processes for the preparation of the compound of formula (Ia) as outlined in Scheme 2 below.

STEP 1a: Preparation of the Compound of Formula (XIIa), wherein X is —OH and Y is Selected from Br or Cl

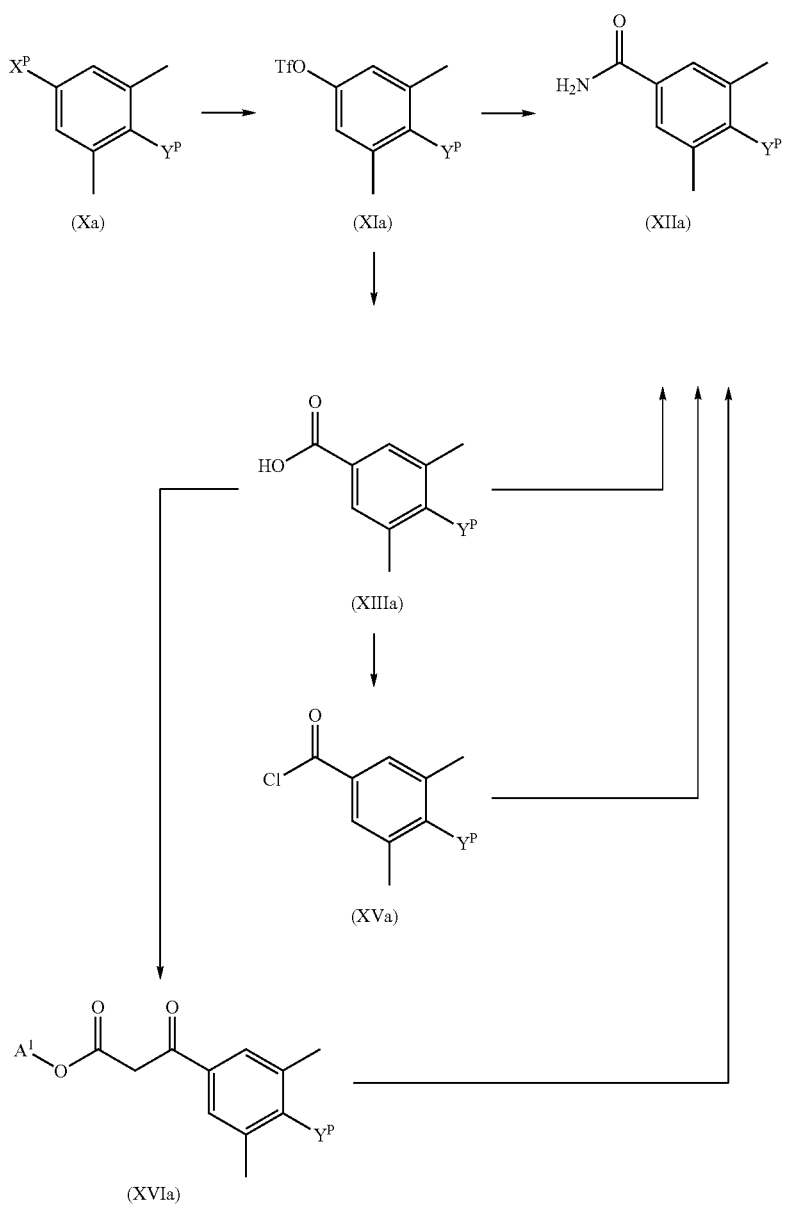

or

STEP 1a: Preparation of the Compound of Formula (XIIa), wherein X is —OC(O)—$C_{1-4}$alkyl and Y is Selected from Br, Cl or I
STEP 2a: Preparation of the Compound of Formula (XIXa)
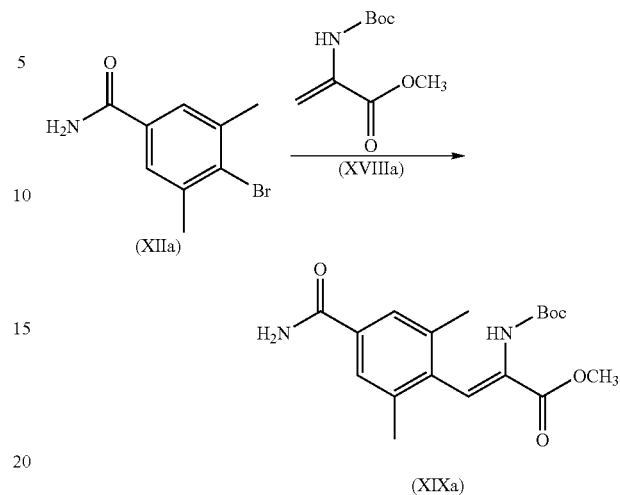
STEP 3a: Preparation of the Compound of Formula (XXa)
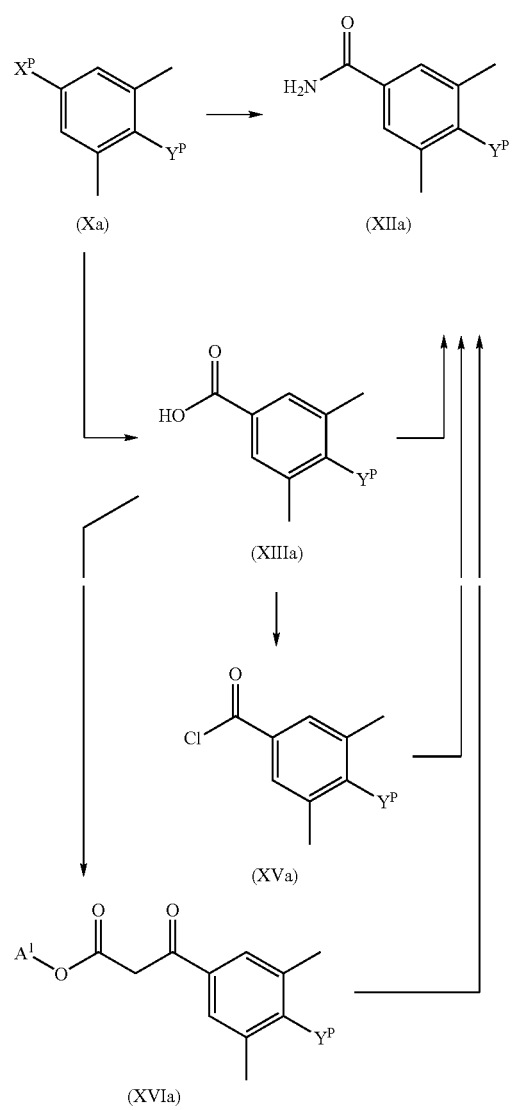
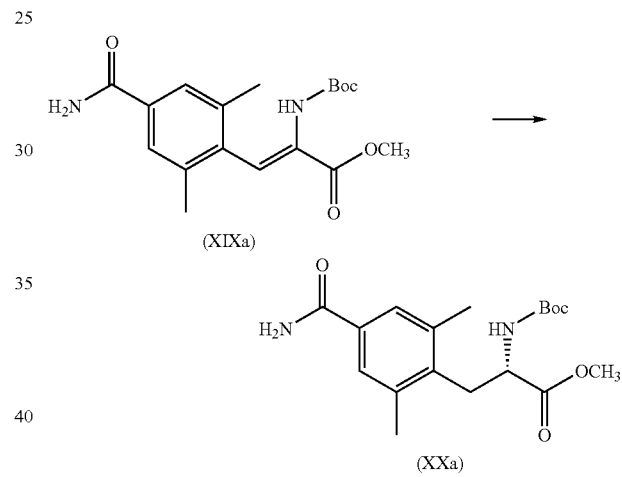
STEP 4a: Preparation of the Compound of Formula (Ia)
Scheme 2
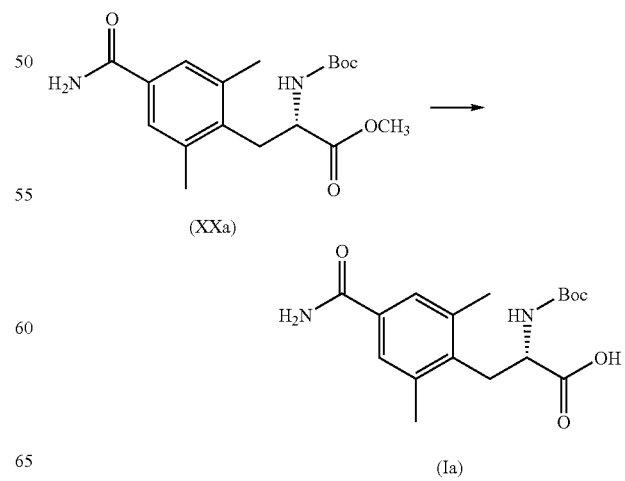
STEP 1a: Preparation of the Compound of Formula (XIIa), wherein X is —CN and Y is Selected from Br, Cl or I
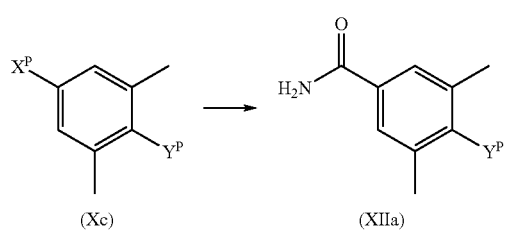

STEP 1a: Wherein X is —OH and Y is Selected from Br or Cl

Accordingly, a suitably substituted compound of formula (Xa), wherein $X^P$ is OH and wherein $Y^P$ is Br or Cl, preferably $Y^P$ is Br, a known compound or compound prepared by known methods, is reacted with a tritlating reagent such as triflic anhydride, N-phenyltrifluoromethanesulfonimide, and the like; in the presence of an organic or inorganic base such as pyridine, TEA, DIPEA, $K_3PO_4$, $K_2CO_3$, and the like, preferably pyridine; optionally in an organic solvent such as DCM, chloroform, THF, and the like, to yield the corresponding compound of formula (XIa).

The compound of formula (XIa) is reacted with carbon monoxide or a source of carbon monoxide such as $Ac_2O$ in combination with HCOONa (see for example, S. Cacchi, G. Fabrizi, A. Goggiamani, Org. Lett. (2003), 5(23), pp 4269-4272) and a suitable source of ammonia such as HMDS, ammonia gas, and the like; in the presence of a palladium catalyst such $PdCl_2$, $Pd_2(OAc)_2$, and the like, in combination with a ligand, such DPPP, DPPF, $P(Ph)_3$, and the like; or in the presence of a palladium:ligand complex such as $Pd(PPh_3)_4$, and the like; in an organic solvent such as DMF, THF, dioxane, and the like, preferably DMF; at a temperature in the range of from about 50° C. to about 160° C., preferably at a temperature in the range of from about 60° C. to about 120° C.; to yield the corresponding compound of formula (XIIa).

Alternatively, the compound of formula (XIa) is reacted with carbon monoxide or a source of carbon monoxide such as $Ac_2O$ in combination with HCOONa (see for example, S. Cacchi, G. Fabrizi, A. Goggiamani, Org. Lett. (2003), 5(23), pp 4269-4272); in the presence of an inorganic base such as $K_2CO_3$, $Na_2CO_3$, and the like; in an organic solvent such as DMF, dioxane, THF, and the like; at a temperature in the range of from about 50° C. to about 160° C., preferably at a temperature in the range of from about 60° C. to about 80° C.; to yield the corresponding compound of formula (XIIIa).

The compound of formula (XIIIa) is reacted with a suitable source of ammonia such as HMDS, ammonia gas, and the like, preferably HMDS; in the presence of a coupling agent such as EDCl, HOBT, PyBop, PyBrop, and the like; preferably in the presence of an organic base such as TEA, DIPEA, pyridine, the like, or in the presence of an amount of the source of ammonia sufficient to act as the base, preferably greater than about 2 equivalents; in an organic solvent such as THF, dioxane, DMF, and the like, to yield the corresponding compound of formula (XIIa).

Alternatively, the compound of formula (XIa) is reacted with carbon monoxide or a source of carbon monoxide such as $Ac_2O$ in combination with HCOONa (see for example, S. Cacchi, G. Fabrizi, A. Goggiamani, Org. Lett. (2003), 5(23), pp 4269-4272); in the presence of an inorganic base such as $K_2CO_3$, $Na_2CO_3$, and the like; in an organic solvent such as DMF, dioxane, THF, and the like; at a temperature in the range of from about 50° C. to about 160° C., preferably at a temperature in the range of from about 60° C. to about 80° C.; to yield the corresponding compound of formula (XIIIa).

The compound of formula (XIIIa) is reacted with a suitable source of chlorine such as thionyl chloride, $PCl_3$, $PCl_5$, oxalyl chloride, oxalyl chloride in DMF, and the like; in an organic solvent such as DCM, chloroform, and the like; preferably at a temperature greater than about room temperature, more preferably at a temperature in the range of about 35° C. to about 60° C.; to yield the corresponding compound of formula (XVa).

The compound of formula (XVa) is reacted with a suitable source of ammonia such as ammonium chloride, $NH_4OH$, HMDS, ammonia gas, and the like, preferably ammonium chloride; preferably in the presence of an organic base such as TEA, DIPEA, pyridine, the like, or in the presence of an amount of the source of ammonia sufficient to act as the base, preferably greater than about 2 equivalents; in an organic solvent such as THF, dioxane, DMF, and the like; to yield the corresponding compound of formula (XIIa).

Alternatively, the compound of formula (XIa) is reacted with carbon monoxide or a source of carbon monoxide such as $Ac_2O$ in combination with HCOONa (see for example, S. Cacchi, G. Fabrizi, A. Goggiamani, Org. Lett. (2003), 5(23), pp 4269-4272); in the presence of an inorganic base such as $K_2CO_3$, $Na_2CO_3$, and the like; in an organic solvent such as DMF, dioxane, THF, and the like; at a temperature in the range of from about 50° C. to about 160° C., preferably at a temperature in the range of from about 60° C. to about 80° C; to yield the corresponding compound of formula (XIIIa).

Alternatively, the compound of formula (XIIIa) is reacted with $C_{1-4}$alkyl-chloroformate, preferably, methylchloroformate; in the presence of a organic base such as TEA, DIPEA, pyridine and the like; preferably at a temperature less than, about room temperature, more preferably at a temperature of about 0° C.; in an organic solvent such as DMF, DCM, chloroform, THF, and the like; to yield the corresponding compound of formula (XVIa), wherein $A^1$ is the corresponding $C_{1-4}$alkyl, preferably methyl.

The compound of formula (XVIa) is reacted with a suitable source of ammonia such as $NH_4OH$, HMDS, ammonia gas, and the like, preferably $NH_4OH$; in the presence of a palladium catalyst such $PdCl_2$, $Pd_2(OAc)_2$, and the like, in combination with a ligand, such DPPP, DPPF, $P(Ph)_3$, and the like; or in the presence of a palladium:ligand complex such as $Pd(PPh_3)_4$, and the like; at a temperature in the range of from about 50° C. to about 160° C., preferably at a temperature in the range of from about 60° C. to about 80° C; to yield the corresponding compound of formula (XIIa).

One skilled in the art will further recognize that the compound of formula (XIa) may be reacted according to known methods, to yield the corresponding compound of formula (Xa) wherein $X^P$ is —C(O)—$OC_{1-4}$alkyl or CN.

STEP 1a: Wherein X is —C(O)—$C_{1-4}$alkyl and wherein $Y^P$ is Br, Cl or I

Alternatively, a suitably substituted compound of formula (Xa), wherein $X^P$ is —C(O)—$OC_{1-4}$alkyl and wherein $Y^P$ is selected from Br, Cl or I, a known compound or compound prepared by known methods, is reacted with a suitable source of ammonia such as $NH_4OH$, HMDS, ammonia gas, and the like; at a temperature greater than room temperature, preferably at about reflux temperature; to yield the corresponding compound of formula (XIIa).

Alternatively, a suitably substituted compound of formula (Xa), wherein $X^P$ is —C(O)—$OC_{1-4}$alkyl and wherein $Y^P$ is selected from Br, Cl or I,.a known compound or compound prepared by known methods, is reacted with a suitable source of ammonia such as $NH_4OH$, HMDS, ammonia gas, and the like; in the presence of a activating agent such as trimethylaluminum, triisopropylaluminum, and the like; in an aprotic organic solvent such as THF, dioxane, toluene, DCM, and the like; preferably, at a temperature in the range of about 0° C. to reflux temperature; to yield the corresponding compound of formula (XIIa).

Alternatively, a suitably substituted compound of formula (Xa), wherein $X^P$ is —C(O)—$OC_{1-4}$alkyl and wherein $Y^P$ is selected from Br, Cl or I, a known compound or compound prepared by known methods, is hydrolyzed according to known methods; for example by reacting with a base such as NaOH, LiOH, KOH, and the like, or by reacting with an acid such as HCl, $H_2SO_4$, and the like; preferably, the compound of formula (Xa) is reacted with an acid at a temperature greater than about room temperature, preferably at a temperature in the range of from about 600 to about 120° C., preferably at a temperature of about 100° C.; to yield the corresponding compound of formula (XIIIa).

The compound of formula (XIIIa) is reacted with a suitable source of ammonia such as HMDS, ammonia gas, and the like, preferably HMDS; in the presence of a coupling agent such as EDCl, HOBT, PyBop, PyBrop, and the like; preferably in the presence of an organic base such as TEA, DIPEA, pyridine, the like, or in the presence of an amount of the source of ammonia sufficient to act as the base, preferably greater than about 2 equivalents; in an organic solvent such as THF, dioxane, DMF, and the like, to yield the corresponding compound of formula (XIIa).

Alternatively, the compound of formula (Xa), wherein $X^P$ is $—C(O)—OC_{1-4}$alkyl and wherein $Y^P$ is selected from Br, Cl or I, a known compound or compound prepared by known methods, is reacted with carbon monoxide or a source of carbon monoxide such as $Ac_2O$ in combination with HCOONa (see, for example, S. Cacchi, G. Fabrizi, A. Goggiamani, Org. Lett. (2003), 5(23), pp 4269-4272); in the presence of an inorganic base such as $K_2CO_3$, $Na_2CO_3$, and the like; in an organic solvent such as DMF, dioxane, THF, and the like; at a temperature in the range of from about 50° C. to about 160° C., preferably at a temperature in the range of from about 60° C. to about 80° C; to yield the corresponding compound of formula (XIIIa).

The compound of formula (XIIIa) is reacted with a suitable source of chlorine such as thionyl chloride, $PCl_3$, $PCl_5$, oxalyl chloride, oxalyl chloride in DMF, and the like; in an organic solvent such as DCM, chloroform, and the like; preferably at a temperature greater than about room temperature, more preferably at a temperature in the range of about 35° C. to about 60° C., to yield the corresponding compound of formula (XVa).

The compound of formula (XVa) is reacted with a suitable source of ammonia such as ammonium chloride, $NH_4OH$, HMDS, ammonia gas, and the like, preferably ammonium chloride; preferably in the presence of an organic base such as TEA, DIPEA, pyridine, the like; or in the presence of an amount of the source of ammonia sufficient to act as the base, preferably greater than about 2 equivalents; in an organic solvent such as THF, dioxane, DMF, and the like; to yield the corresponding compound of formula (XIIa).

Alternatively, the compound of formula (Xa), wherein $X^P$ is $—C(O)—OC_{1-4}$alkyl and wherein $Y^P$ is selected from Br, Cl or I, a known compound or compound prepared by known methods, is reacted with carbon monoxide or a source of carbon monoxide such as $Ac_2O$ in combination with HCOONa (see for example, S. Cacchi, G. Fabrizi, A. Goggiamani, Org. Lett. (2003), 5(23), pp 4269-4272); in the presence of an inorganic base such as $K_2CO_3$, $Na_2CO_3$, and the like; in an organic solvent such as DMF, dioxane, THF, and the like; at a temperature in the range of from about 50° C. to about 160° C., preferably at a temperature in the range of from about 60° C. to about 80° C; to yield the corresponding compound of formula (XIIIa).

Alternatively, the compound of formula (XIIIa) is reacted with $C_{1-4}$alkyl-chloroformate, preferably, methylchloroformate; in the presence of a organic base such as TEA, DIPEA, pyridine and the like; preferably at a temperature less than about room temperature, more preferably at a temperature of about 0° C.; in an organic solvent such as DMF, DCM, chloroform, THF, and the like; to yield the corresponding compound of formula (XVIa), wherein $A^1$ is the corresponding $C_{1-4}$alkyl, preferably methyl.

The compound of formula (XVIa) is reacted with a suitable source of ammonia such as $NH_4OH$, HMDS, ammonia gas, and the like, preferably $NH_4OH$; in the presence of a palladium catalyst such $PdCl_2$, $Pd_2(OAc)_2$, and the like, in combination with a ligand, such DPPP, DPPF, $P(Ph)_3$, and the like, or in the presence of a palladium:ligand complex such as $Pd(PPh_3)_4$, and the like; at a temperature in the range of from about 50° C. to about 160° C., preferably at a temperature in the range of from about 60° C. to about 80° C.; to yield the corresponding compound of formula (XIIa).

STEP 1a: Wherein X is —CN and wherein $Y^P$ is Br, Cl or I

Alternatively, a suitably substituted compound of formula (Xa), wherein $X^P$ is CN and wherein $Y^P$ is selected from Br, Cl or I, a known compound or compound prepared by known methods, is reacted with an acid such as concentrated sulfuric acid, and the like; at a temperature greater than about room temperature, preferably at about reflux temperature; to yield the corresponding compound of formula (XVIa).

Alternatively, a suitably substituted: compound of formula (Xa), wherein $X^P$ is CN and wherein $Y^P$ is selected from Br, Cl or I, a known compound or compound prepared by known methods, is reacted with an inorganic base such as NaOH, KOH, and the like; at a temperature greater than about room temperature, preferably at about reflux temperature; to yield the corresponding compound of formula (XVIa).

Preferably, a suitably substituted compound of formula (Xa), a known compound or compound prepared by known methods, is reacted with a triflating reagent such as triflic anhydride, N-phenyltrifluoromethanesulfonimide, and the like, preferably triflic anhydride; in the presence of an organic or inorganic base such as pyridine, TEA, DIPEA, $K_3PO_4$, $K_2CO_3$, and the like, preferably pyridine; optionally in an organic solvent such as DCM, chloroform, THF, and the like; to yield the corresponding compound of formula (XIa).

The compound of formula (XIa) is reacted with carbon monoxide or a source of carbon monoxide such as $Ac_2O$ in combination with HCOONa (see for example, S. Cacchi, G. Fabrizi, A. Goggiamani, Org. Lett. (2003), 5(23), pp 4269-4272) and a suitable source of ammonia such as HMDS, ammonia gas, and the like; preferably the compound of formula (XIa) is reacted with carbon monoxide and HMDS; in the presence of a palladium catalyst such $PdCl_2$, $Pd_2(OAc)_2$, and the like, in combination with a suitable ligand, such DPPP, DPPF, $P(Ph)_3$, and the like; or in the presence of a palladium:ligand complex such as $Pd(PPh_3)_4$, and the like; preferably, in the presence of $PdCl_2$ in combination with DPPP; at a temperature in the range of from about 50° C. to about 160° C., preferably at a temperature in the range of from about 60° C. to about 120° C., more preferably, at a temperature of about 100° C.; in an organic solvent such as DMF, THF, dioxane, and the like, preferably, in DMF; to yield the corresponding compound of formula (XII).

STEP 2a:

The compound of formula (XIIa) is reacted with a suitably substituted compound of formula (XVIIIa), a known compound or compound prepared by known methods, in the presence of palladium catalyst such as $Pd_2(dba)_3$, $Pd(OAc)_2$, $PdCl_2$, and the like, preferably $Pd_2(dba)_3$; and preferably in the presence of a phosphorous ligand such as $P(o-toluene)_3$, $P(Ph)_3$, $P(t-butyl)_3$, DPPE, and the like, preferably P(o-toluene)$_3$; or in the presence of a palladium:ligand complex such as $Pd(PPh_3)_4$, and the like; in the presence of an organic or inorganic base such as dicyclohexylmethylamine, $Na_2CO_3$, $K_2CO_3$, TEA, DIPEA, pyridine, and the like, preferably TEA; in an organic solvent such as DMF, dioxane, and the like, preferably DMF; at a temperature greater than about room temperature, preferably at a temperature in the range of about 60° C. to about 120° C., preferably at about 120° C.; to yield the corresponding compound of formula (XIXa).

STEP 3a:

The compound of formula (XIXa) is reacted with hydrogen gas, at a pressure sufficient to hydrogenate, preferably at a pressure greater than about 500 psi, more preferably, at a pressure greater than about 800 psi, more preferably still, at a pressure about 1000 psi; in the presence of a suitable chiral catalyst such as [Rh(cod)(R,R-DIPAMP)]$^+$BF$_4^-$, [Rh(cod)(R,R-DIPAMP)]$^+$SO$_2$CF$_3^-$, and the like; wherein the chiral catalyst is preferably present in an amount greater than about 0.01 equivalents, more preferably, in an amount of about 0.04 equivalents; at a temperature greater than about room temperature, preferably at a temperature in the range of about 60° C. to about 100° C., more preferably, at a temperature of about 60° C.; in an organic solvent such as methanol, ethanol, THF, ethyl acetate, and the like, preferably methanol; preferably not under vacuum; to yield the corresponding compound of formula (XXa), wherein the S-enantiomer is present in an enantiomeric excess of greater than about 80%, preferably, in an enantiomeric excess of greater than about 90%, more preferably, in an enantiomeric excess of greater than about 95%, more preferably, in an enantiomeric excess of greater than about 98%, most preferably, in an enantiomeric excess of greater than about 99%.

One skilled in the art will recognize that if the chiral catalyst is oxygen sensitive, then the hydrogenation reaction vessel is purged with an inert gas such as argon, nitrogen, and the like, prior to charging the vessel with the oxygen sensitive catalyst reagents and hydrogen gas.

One skilled in the art will recognize that the compound of formula (XIXa) may be optionally reacted to yield the corresponding racemic compound of formula (XXb), as outlined in the scheme below,

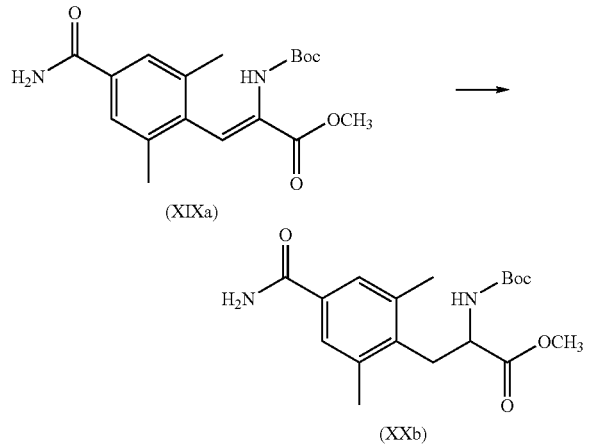

(XIXa)

(XXb)

by hydrogenating the compound of formula (XIXa) according to known methods, for example, by reacting with hydrogen or a source of hydrogen (such as cyclohexadiene, and the like); in the presence of a catalyst such as platinum oxide, palladium on carbon, nickel, ClRh(PPh$_3$)$_3$, RuCl$_2$, and the like, preferably palladium on carbon; in a solvent such as methanol, ethanol, THF, ethyl acetate, and the like; in an organic solvent such as methanol, ethanol, THF, ethyl acetate, and the like, preferably methanol; at a temperature greater than room temperature, preferably at a temperature in the range of about 60° C. to about 120° C.

Preferably, for the preparation of the compound of formula (Ib), the compound of formula (XIXa) is reacted with hydrogen gas; at a pressure sufficient to hydrogenate, preferably at a pressure greater than about 40 psi, more preferably at a pressure of about 51 psi; in a solvent such as methanol, ethanol, THF, and the like, preferably methanol; preferably, at about room temperature; to yield the corresponding compound of formula (XXb).

The compound of formula (XXb) is then reacted according to the process described in Step 4a below, to yield the corresponding compound of formula (Ib).

STEP 4a:

The compound of formula (XXa) is reacted with an aqueous base such as NaOH, LiOH, KOH, and the like, preferably LiOH; in an organic solvent such as methanol, THF, ethanol, and the like, preferably THF; to yield the corresponding compound of formula (Ia).

The present invention is further directed to processes for the preparation of compounds of formula (II).

The compounds of formula (I) may be further reacted according to known processes, for example as disclosed in U.S. patent application Ser. No.11/079,647, filed Mar. 14, 2005, and published as US Patent Publication US-2005-0203143-A1, Sep. 15, 2005, to yield the corresponding compounds of formula (II). More specifically, the compounds of formula (II) may be prepared according to the process outlined in Scheme 3 below.

Scheme 3

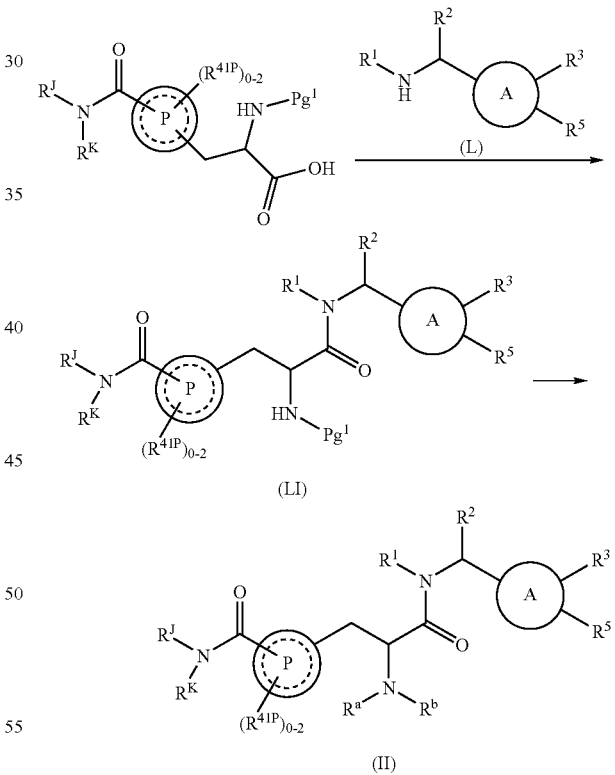

Accordingly, a suitably substituted compound of formula (I) is reacted with a suitably substituted compound of formula (L), a known compound or compound prepared by known methods, under standard peptide coupling conditions (for example, with a coupling agent such as EDCl and an additive such as HOBT), to yield the corresponding compound of formula (LI).

The compound of formula (LI) is then de-protected according to known methods, and then further, optionally reacted according to know methods, to yield the corresponding compound of formula (II) wherein $R^a$ and $R^b$ are each other than hydrogen. For example, the compound of formula (LI) is de-protected and the alkylated, according to known methods, to yield the corresponding compound of formula (II) wherein one or both of $R^a$ and $R^b$ is alkyl. Alternatively, for compounds of formula (II) wherein $R^a$ and $R^b$ are taken together to form a ring, the compound of formula (LI) is de-protected and then converted to the corresponding ring by reductive cyclization with a suitably selected di-aldehyde.

The present invention is further directed to processes for the preparation of compounds of formula (XIX). More specifically, in an embodiment, the present invention is directed to a process for the preparation of compounds of formula (XIX) as outlined in Scheme 4.

Scheme 4

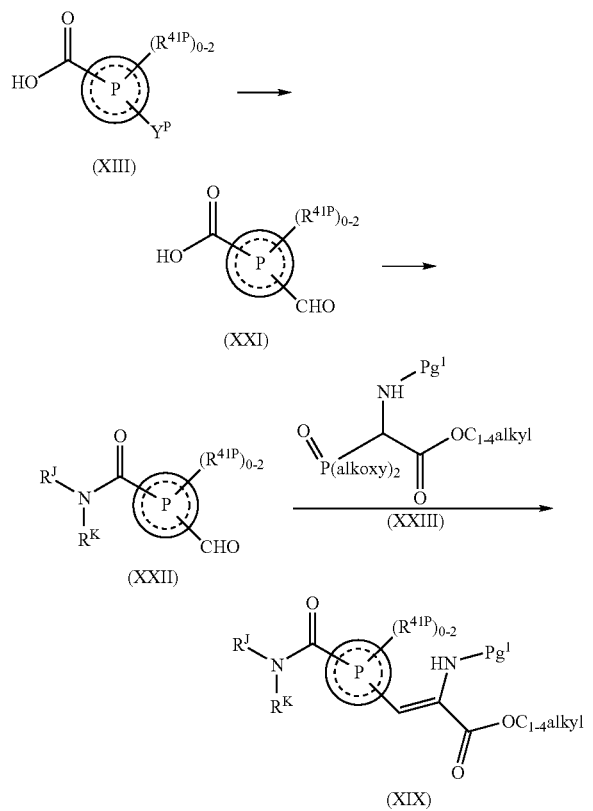

Accordingly, a suitably substituted compound of formula (XIII), wherein $Y^P$ is Br or Cl, is reacted with a formylating reagent such as a DMF, $HC(O)$—$N(CH_3)(OCH_3)$, and the like; in the presence of a base such as n-butyl lithium, NaH, and the like; in an organic solvent such as THF, dioxane, and the like; at a temperature less than about room temperature, preferably at a temperature in the range of about $-130°$ C. to about $0°$ C., more preferably, at about $-100°$ C.; to yield the corresponding compound of formula (XXI).

The compound of formula (XXI) is reacted with a suitably substituted compound of formula (XIV), a known compound or compound prepared by known methods, or when $R^J$ and $R^K$ are each hydrogen, with a suitable source of ammonia such as HMDS, ammonia gas, and the like, preferably HMDS; in the presence of a coupling agent such as EDCl, HOBT, PyBop, PyBrop, and the like; preferably in the presence of an organic base such as TEA, DIPEA, pyridine, the like, or an amount of the compound of formula (XIV) or source of ammonia sufficient to act as the base, preferably greater than about 2 equivalents; in an organic solvent such as THF, dioxane, DMF, and the like; to yield the corresponding compound of formula (XXII).

The compound of formula (XXII) is reacted with a suitably selected compound of formula (XXIII), a known compound or compound prepared by known methods; in the presence of a base such as DBU, potassium t-butoxide, NaH, and the like; in an organic solvent such as THF, dioxane, and the like; preferably at about room temperature, to yield the corresponding compound of formula (XIX).

In another embodiment, the present invention is directed to a process for the preparation of compounds of formula (XIX) as outlined in Scheme 5.

Scheme 5

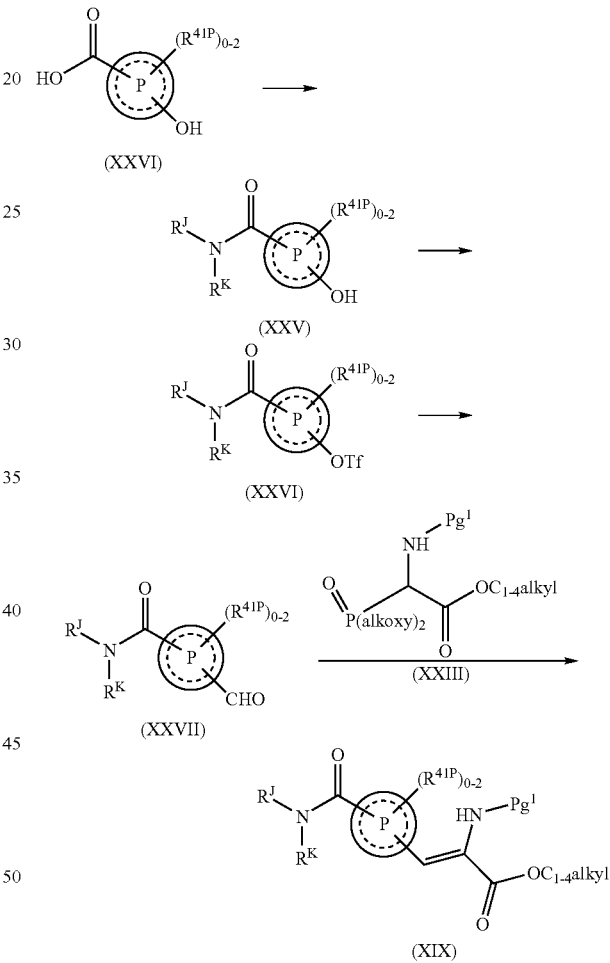

Accordingly, a suitably substituted compound of formula (XXIV), a known compound or compound prepared by known methods, is reacted with a suitably substituted compound of formula (XIV), a known compound or compound prepared by known methods, or when $R^J$ and $R^K$ are each hydrogen, with a suitable source of ammonia such as HMDS, ammonia gas, and the like, preferably HMDS; in the presence of a coupling agent such as EDCl, HOBT, PyBop, PyBrop, and the like; preferably in the presence of an organic base such as TEA, DIPEA, pyridine, the like, or an amount of the compound of formula (XIV) or source of ammonia sufficient to act as the base, preferably greater than about 2 equivalents;

in an organic solvent such as THF, dioxane, DMF, and the like; to yield the corresponding compound of formula (XXV).

The compound of formula (XXV) is reacted with triflating reagent such as triflic anhydride, N-phenyltrifluoromethane-sulfonimide, and the like; in the presence of an organic or inorganic base such as pyridine, TEA, DIPEA, $K_3PO_4$, $K_2CO_3$, and the like; optionally in an organic solvent such as DCM, chloroform, THF, and the like; to yield the corresponding compound of formula (XXVI).

The compound of formula (XXVI) is reacted with carbon monoxide; in the presence of a palladium catalyst such $PdCl_2$, $Pd_2(OAc)_2$, and the like, in combination with a suitable ligand, such DPPP, DPPF, $P(Ph)_3$, and the like; or in the presence of a palladium:ligand complex such as $Pd(PPh_3)_4$, and the like; in the presence of an organic base such as TEA, DIPEA, pyridine, and the like;

in the presence of $(alkyl)_3SiH$; in an organic solvent such as DMF, THF, dioxane, and the like; to yield the corresponding compound of formula (XXVII).

The compound of formula (XXVII) is reacted with a suitably selected compound of formula (XXIII), a known compound or compound prepared by known methods; in the presence of a base such as DBU, potassium t-butoxide, NaH, and the like; in an organic solvent such as THF, dioxane, and the like; preferably at about room temperature, to yield the corresponding compound of formula (XIX).

In an embodiment, the present invention is directed to processes for the preparation of the compound of formula (XIX). More specifically, in an embodiment, the present invention is directed to a process for the preparation of compounds of formula (XIXa) as outlined in Scheme 6.

Scheme 6

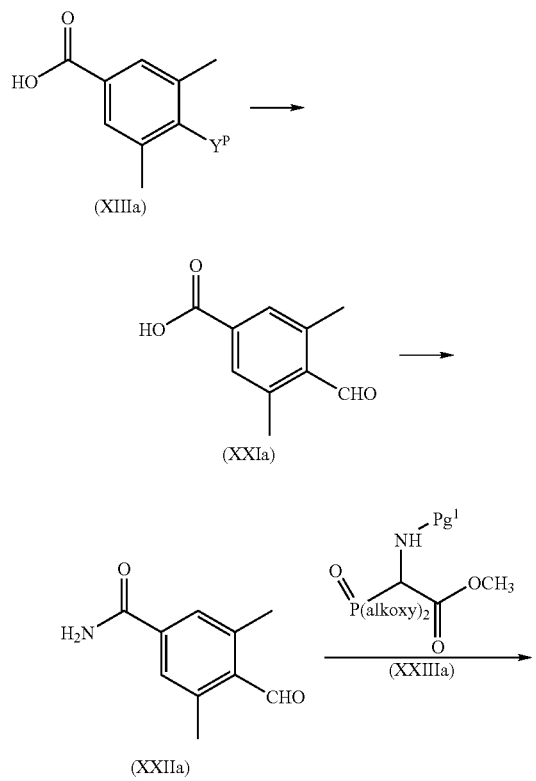

-continued

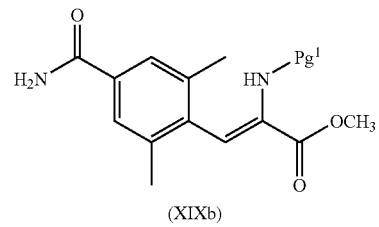

Accordingly, a suitably substituted compound of formula (XIIIa), wherein $Y^P$ is Br or Cl, is reacted with a formylating reagent such as a DMF, $HC(O)-N(CH_3)(OCH_3)$, and the like; in the presence of a base such as n-butyl lithium, -NaH, and the like; in an organic solvent such as THF, dioxane, and the like; at a temperature less than about room temperature, preferably at a temperature in the range of about −130° C. to about 0° C., more preferably, at about −100° C.; to yield the corresponding compound of formula (XXIa).

The compound of formula (XXIa) is reacted with a suitable source of ammonia such as HMDS, ammonia gas, and the like, preferably HMDS; in the presence of a coupling agent such as EDCl, HOBT, PyBop, PyBrop, and the like; preferably in the presence of an organic base such as TEA, DIPEA, pyridine, the like, or an amount of the source of ammonia sufficient to act as the base, preferably greater than about 2 equivalents; in an organic solvent such as THF, dioxane, DMF, and the like; to yield the corresponding compound of formula (XXIIa).

The compound of formula (XXIIa) is reacted with a suitably selected compound of formula (XXIIIa), wherein Pg1 is a suitable nitrogen protecting group such as Boc, Cbz, and the like, a known compound or compound prepared by known methods; in the presence of a base such as DBU, potassium t-butoxide, NaH, and the like; in an organic solvent such as THF, dioxane, and the like; preferably at about room temperature, to yield the corresponding compound of formula (XIXb).

In another embodiment, the present invention is directed a process for the preparation of compounds of formula (XIXa) as outlined in Scheme 7.

Scheme 7

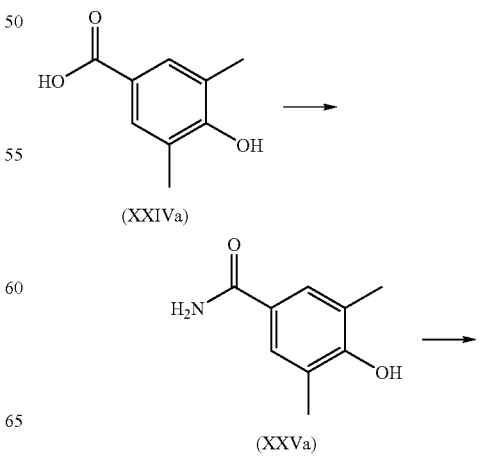

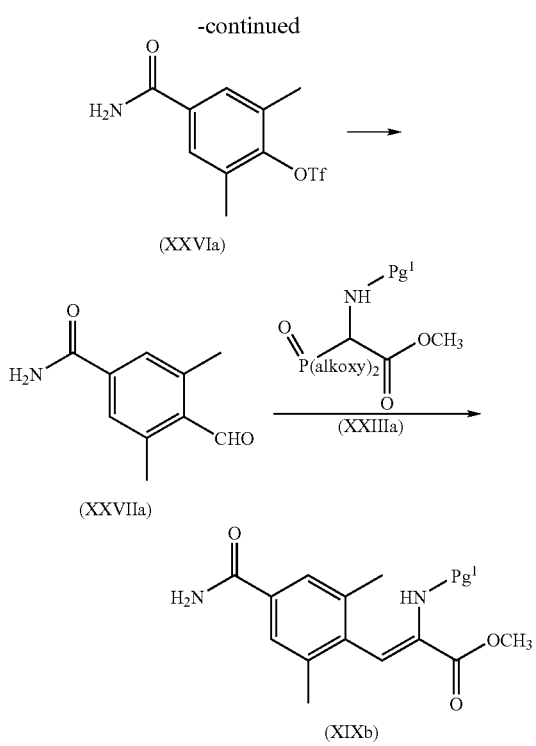

Accordingly, a suitably substituted compound of formula (XXIVa), a known compound or compound prepared by known methods, is reacted with a suitable source of ammonia such as HMDS, ammonia gas, and the like, preferably HMDS; in the presence of a coupling agent such as EDCl, HOBT, PyBop, PyBrop, and the like; preferably in the presence of an organic base such as TEA, DIPEA, pyridine, the like, or in the presence of an amount of the source of ammonia sufficient to act as the base, preferably greater than about 2 equivalents; in an organic solvent such as THF, dioxane, DMF, and the like; to yield the corresponding compound of formula (XXVa).

The compound of formula (XXVa) is reacted with triflating reagent such as triflic anhydride, N-phenyltrifluoromethanesulfonimide, and the like; in the presence of an organic or inorganic base such as pyridine, TEA, DIPEA, $K_3PO_4$, $K_2CO_3$, and the like; optionally in an organic solvent such as DCM, chloroform, THF, and the like; to yield the corresponding compound of formula (XXVIa).

The compound of formula (XXVIa) is reacted with carbon monoxide; in the presence of a palladium catalyst such $PdCl_2$, $Pd_2(OAc)_2$, and the like, in combination with a suitable ligand, such DPPP, DPPF, $P(Ph)_3$, and the like; or in the presence of a palladium:ligand complex such as $Pd(PPh_3)_4$, and the like; in the presence of an organic base such as TEA, DIPEA, pyridine, and the like; in the presence of $(alkyl)_3SiH$; in an organic solvent such as DMF, THF, dioxane, and the like; to yield the corresponding compound of formula (XXVIIa).

The compound of formula (XXVIIa) is reacted with a suitably selected compound of formula (XXIIIa), wherein Pg1 is a suitable nitrogen protecting group such as Boc, Cbz, abd the like, a known compound or compound prepared by known methods; in the presence of a base such as DBU, potassium t-butoxide, NaH, and the like; in an organic solvent such as THF, dioxane, and the like; preferably at about room temperature, to yield the corresponding compound of formula (XIXb).

The present invention further comprises pharmaceutical compositions containing one or more compounds prepared according to any of the processes described herein with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms-depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

EXAMPLE 1

(S)-2-tert-Butoxycarbonylamino-3-(4-carbamoyl-2, 6-dimethyl-phenyl)-propionic acid

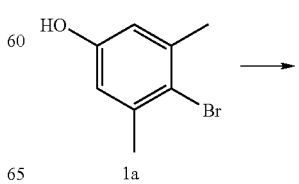

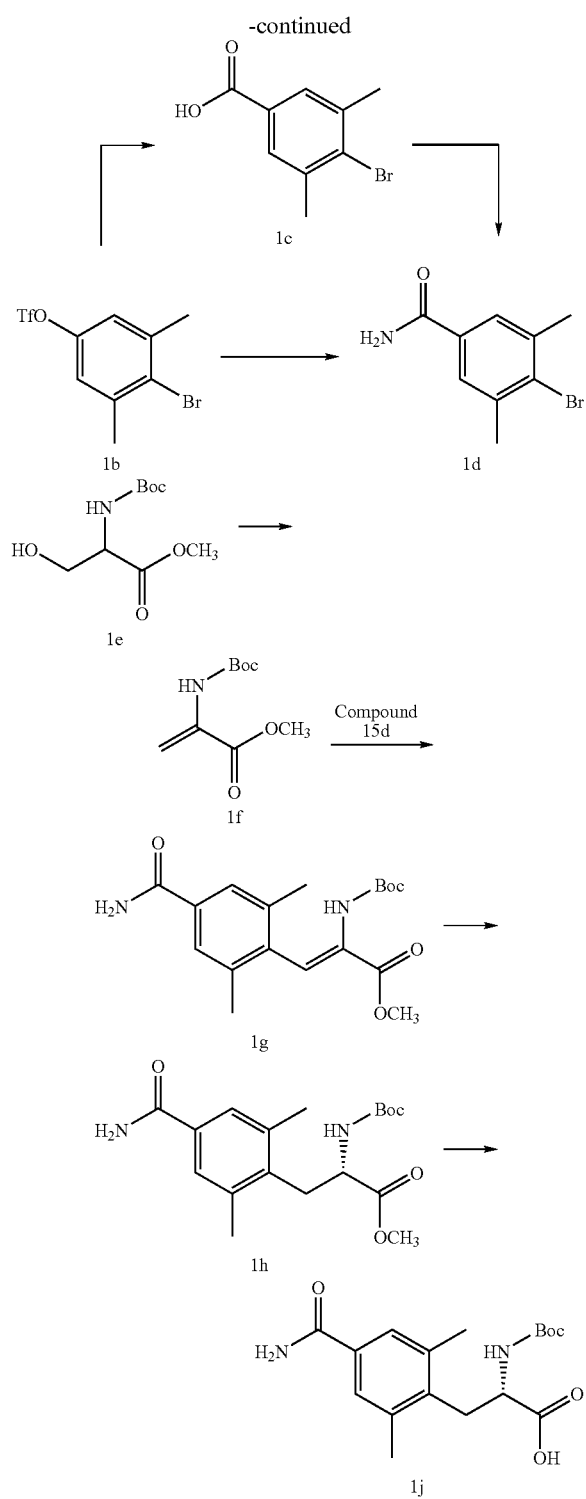

Step A: Trifluoromethanesulfonic acid 4-bromo-3,5-dimethyl-phenyl ester

To a cooled (0° C.) solution of 4-bromo-3,5-dimethylphenol (3.05 g, 15.2 mmol) in pyridine (8 mL) was added trifluoromethanesulfonic anhydride (5.0 g, 17.7 mmol) dropwise. After completion of addition, the resulting mixture was stirred at 0° C. for 15 min, and then at room temperature overnight. The reaction was quenched by addition of water, and then extracted with EtOAc. The organic extracts were washed sequentially with water, 2N HCl (2×), brine, and then dried over $MgSO_4$. Filtration and evaporation to dryness yielded compound 1b as a colorless oil.

$^1$H NMR (300 MHz, $CDCl_3$): δ 2.45 (6H, s), 7.00 (2H, s).

Step B: 4-Bromo-3,5-dimethylbenzoic acid

Into a solution of compound 1b (6.57 g, 19.7 mmol) in DMF (65 mL) were added $K_2CO_3$ (13.1 g, 94.7 mmol), $Pd(OAc)_2$ (0.44 g, 1.97 mmol) and 1,1'-bis(diphenylphosphino)ferrocene (2.29 g, 4.14 mmol). The resulting mixture was bubbled in gaseous CO for 10 min and was heated to 60° C. for 7.5 h with a $CO_{(g)}$ balloon. The cooled mixture was partitioned between aqueous $NaHCO_3$ and EtOAc, and filtered. The aqueous phase was separated, acidified with aqueous 6N HCl, extracted with EtOAc, and then dried over $Na_2SO_4$. Filtration and concentration of the filtrate yielded crude compound 1c as a brown residue, which was used in the next step without further purification.

Step C: Method A:
4-Bromo-3,5-dimethyl-benzamide

Into a suspension of compound 1c in DCM (40 mL) was added $SOCl_2$ (3.1 mL, 42 mmol) and the mixture was heated at reflux for 2 h. Upon removal of the solvent by evaporation, the residue was dissolved in DCM (40 mL) and then ammonium hydroxide (28% $NH_3$ in water, 2.8 mL) was added. The reaction mixture was heated at 50° C. for 2 h and concentrated. The residue was diluted with $H_2O$, extracted with EtOAc, and the organic portion was dried over $Na_2SO_4$. After filtration and evaporation, the residue was purified by flash column chramotagraphy (eluent: EtOAc) to yield compound 1d as an off-white solid.

$^1$H NMR (300 MHz, $CD_3CN$): δ 2.45 (6H, s), 5.94 (1H, br s), 6.71 (1H, br s), 7.57 (2H, s) MS(ES$^+$)(relative intensity): 228.0 (100%) (M+1).

Step C: Method B:
4-Bromo-3,5-dimethyl-benzamide

A mixture of compound 1b (3.33 g, 10 mmol), $PdCl_2$ (0.053 g, 0.3 mmol), hexamethyldisilazane (HMDS, 8.4 mL, 40 mmol), and DPPP (0.12 g, 0.3 mmol) was bubbled with a gaseous CO for 5 min. and then stirred in a CO balloon at 80° C. for 4 h. To the reaction mixture was added MeOH (5 mL). The reaction mixture was stirred for 10 min, diluted with 2N $H_2SO_4$ (200 mL), and then extracted with EtOAc. The EtOAc extract was washed with saturated aqueous $NaHCO_3$, brine, and then dried over $Na_2SO_4$. Filtration and evaporation of the resultant filtrate yielded a residue, which was purified by flash column chromatography (eluent: EtOAc) to yield compound 1d as a white solid.

Step D: 2-tert-Butoxycarbonylaminoacrylic acid methyl ester

To a suspension of N-Boc-serine methyl ester (Compound 1e, 2.19 g, 10 mmol) and EDCl (2.01 g, 10.5 mmol) in DCM (70 mL) was added CuCl (1.04 g, 10.5 mmol). The reaction mixture was stirred at room temperature for 72 h. Upon removal of the solvent, the residue was diluted with EtOAc, washed sequentially with water and brine and then dried over MgSO₄. The crude product was purified by flash column chromatography (eluent: EtOAc:hexane ~1:4) to yield compound if as a colorless oil.

¹H NMR (300 MHz, CDCl₃): δ 1.49 (9H, s), 3.83 (3H, s), 5.73 (1H, d, J=1.5 Hz), 6.16 (1 H, s), 7.02 (1H, s).

Step E: (Z)-2-tert-Butoxycarbonylamino-3-(4-carbamoyl-2,6-dimethyl-phenyl)acrylic acid methyl ester A flask charged with compound 1d (0.46 g, 2.0 mmol), compound if (0.80 g, 4.0 mmol), tri-o-tolylphosphine (0.098 g, 0.32 mmol) and DMF (8 mL) was purged with N₂(g) 3 times. After the addition of tris(dibenzylideneacetone)dipalladium (0) (0.074 g, 0.08 mmol) and TEA (0.31 mL, 2.2 mol), the reaction mixture was heated at 110° C. for 24 h. At that time, the reaction was quenched by addition of water, and then extracted with EtOAc. The organic phase was washed with 1N HCl, saturated aqueous NaHCO₃, brine, and dried over MgSO₄. The mixture was concentrated to a residue, which was purified by flash column chromatography (eluent: EtOAc:hexane-1:1 to EtOAc only) to yield compound 1g as a white solid.

¹H NMR (300 MHz, CD₃OD): δ 1.36 (9H, s), 2.26 (6H, s), 3.83 (3H, s), 7.10 (1H, s), 7.56 (2H, s);

¹³C NMR (75 MHz, DMSO-d₆): δ 17.6, 25.7, 50.2, 78.7, 124.9, 126.4, 128.3, 131.2, 135.2, 135.5, 152.8, 164.3, 169.6;

MS (ES⁺) (relative intensity): 349.1 (38%)(M+1).

Step F: (S)-2-tert-Butoxycarbonylamino-3-(4-carbamoyl-2,6-dimethyl-phenyl)propionic acid methyl ester Into a reactor charged with a solution of compound 1g (0.56 g, 1.6 mmol) in degassed MeOH (80 mL) was added [Rh(cod)(R,R-DIPAMP)]⁺BF₄⁻ under a stream of argon. The reactor was sealed and flushed with H₂, stirred at 60° C. under 1000 psi of H₂ for 14 days. The crude product was purified by flash column chromatography (eluent: EtOAc:hexane ~1:1) to yield compound 1 h as a white solid.

ee: >99%; ¹H NMR (300 MHz, CDCl₃): δ 1.36 (9H, s), 2.39 (6H, s), 3.11 (2H, J=7.2 Hz), 3.65 (3H, s), 4.53-4.56 (1 H, m), 5.12 (1H, d, J=8.7 Hz), 5.65 (1 H, br s), 6.09 (1 H, br s), 7.46 (2H, s); MS(ES⁺) (relative intensity): 250.9 (100) (M-Boc)⁺.

Step G: (S)-2-tert-Butoxycarbonylamino-3-(4-carbamoyl-2,6-dimethyl-phenyl)propionic acid Into an ice-cooled solution of compound 1 h (0.22 g, 0.63 mmol) in THF (3.5 mL) was added an aqueous LiOH solution (1 N, 3.5 mL) and the reaction mixture stirred at 0° C. Upon completion of the reaction, the reaction mixture was concentrated and the aqueous phase was neutralized with cooled aqueous 1 N HCl at 0° C., and then extracted with EtOAc. The combined extracts were dried over Na₂SO₄ overnight. Filtration and evaporation of the filtrate to dryness yielded compound 1j as a white solid.

¹H NMR (300 MHz, DMSO-d₆): δ 1.30 (9H, s), 2.32 (6H, s), 2.95(1 H, dd, J=8.8, 13.9 Hz), 3.10 (1H, dd, J=6.2, 14.0 Hz), 4.02-4.12 (1H, m), 7.18-7.23 (2H, m), 7.48 (2H, s), 7.80 (1H, s); MS(ES⁺) (relative intensity): 236.9 (6) (M-Boc)⁺.

EXAMPLE 2

Racemic 2-tert-Butoxycarbonylamino-3-(4-carbamoyl-2,6-dimethyl-phenyl)-propionic acid

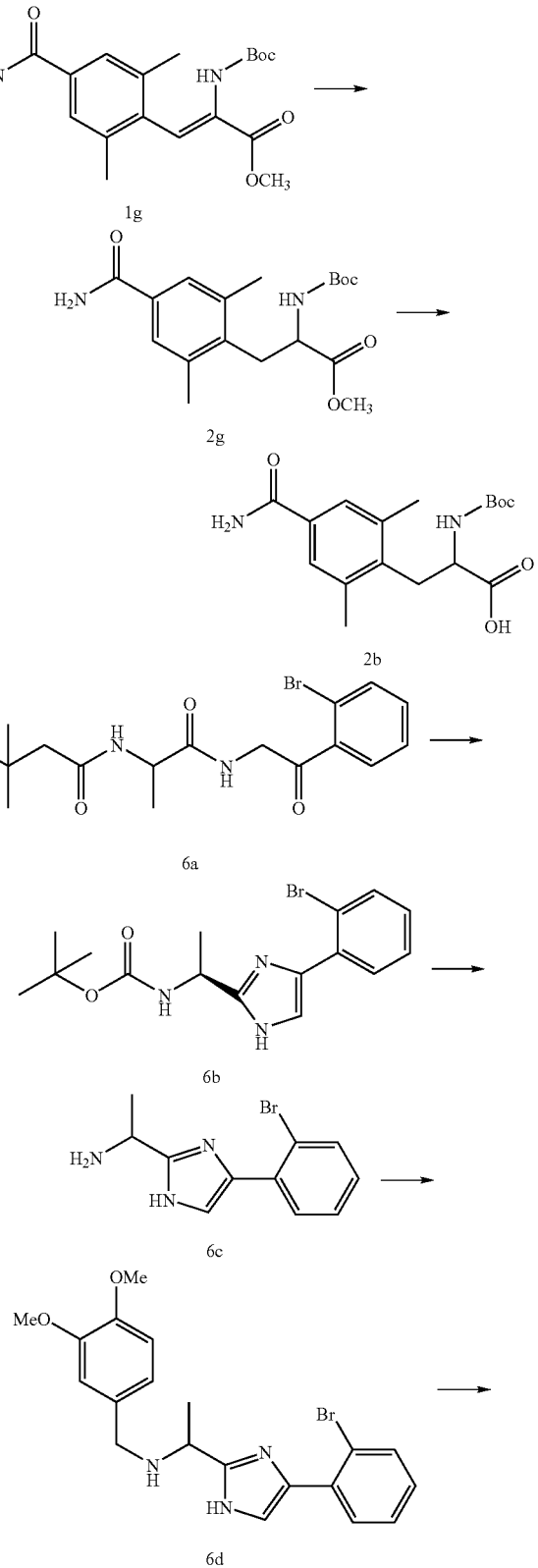

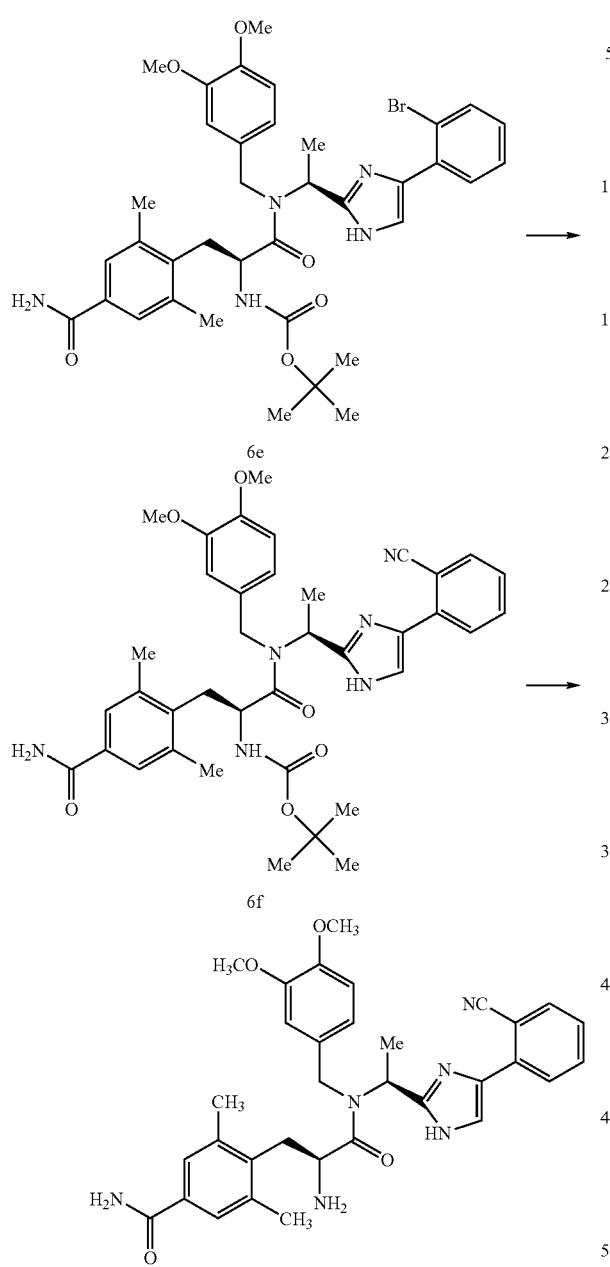

Step A: Racemic 2-tert-butoxycarbonylamino-3-(4-carbamoyl-2,6-dimethyl-phenyl)propionic acid methyl ester To a reactor charged with a solution of compound 1g (0.68 g, 1.95 mmol) in MeOH (80 mL) was added 10% Pd—C (0.5 g). The reactor was connected to a hydrogenator and shaken under 51 psi of $H_2$ overnight. The mixture was filtered through a pad of Celite and the filtrate was concentrated to dryness to yield compound 2a as a white solid.

The $^1$H NMR spectrum was identical to that of (S)-2-tert-butoxycarbonylamino-3-(4-carbamoyl-2,6-dimethyl-phenyl)propionic acid methyl ester, compound 1 h.

Step B: Racemic 2-tert-butoxycarbonylamino-3-(4-carbamoyl-2,6-dimethyl-phenyl)propionic acid Following the procedure described for Example 1, STEP G (preparation of (S)-2-tert-Butoxycarbonylamino-3-(4-carbamoyl-2,6-dimethyl-phenyl)propionic acid), compound 2b -racemic 2-tert-butoxycarbonylamino-3-(4-carbamoyl-2,6-dimethyl-phenyl)propionic acid—was prepared.

EXAMPLE 3

2-Amino-3-(4-hydroxy-2,6-dimethyl-phenyl)-N-isopropyl-N-[1-(4-phenyl-1H-imidazol-2-yl)-ethyl]-propionamide

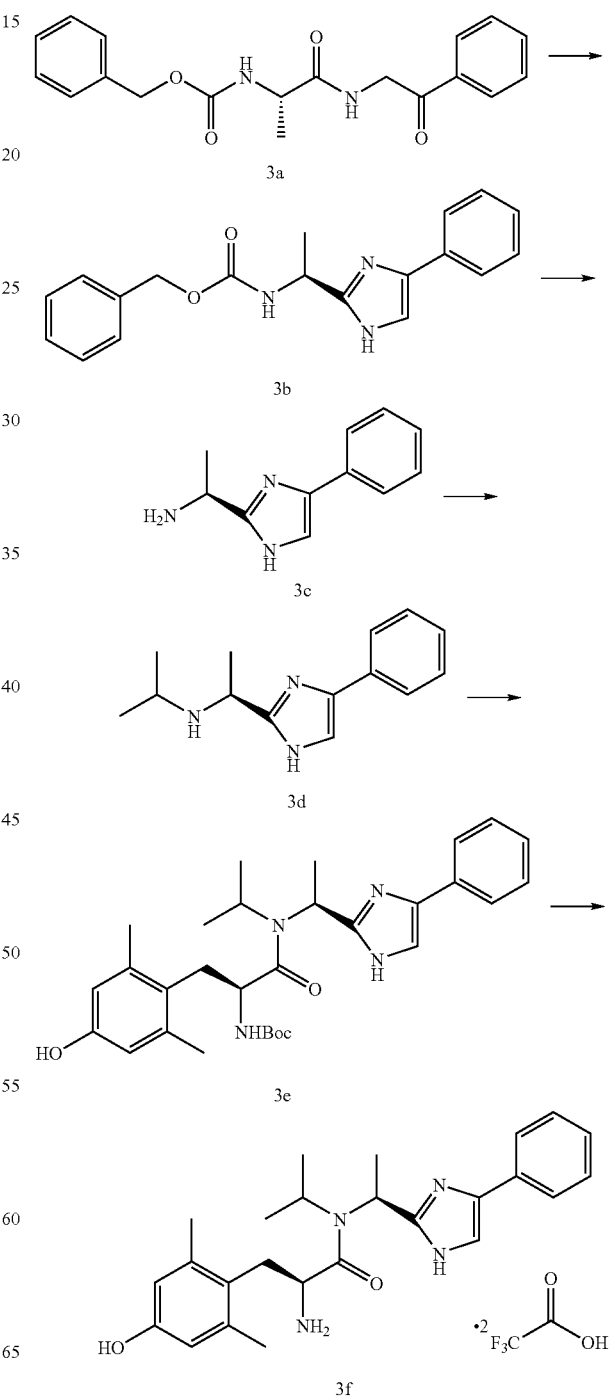

Step A.
[1-(2-Oxo-2-phenyl-ethylcarbamoyl)-ethyl]-carbamic acid benzyl ester To a solution of commercially available N-α-CBZ-L-alanine (2.11 g, 9.5 mmol) in dichloromethane (50 mL) was added 2-aminoacetophenone hydrochloride (1.62 g, 9.5 mmol). The resulting solution was cooled to 0° C. and N-methylmorpholine (1.15 g, 11 mmol), 1-hydroxybenzotriazole (2.55 g, 18.9 mmol) and 1-[3-(dimethylamino)propyl]-3-ethylcarbodiimide hydrochloride (2.35 g, 12.3 mmol), in that order, were added under an Argon atmosphere. The reaction mixture was warmed to room temperature and stirred overnight. The reaction was quenched by addition of saturated aqueous NaHCO$_3$ solution; the separated organic phase was washed with 2N citric acid, saturated NaHCO$_3$ solution and brine, then dried over MgSO$_4$ overnight. After filtration and concentration, the residue was purified by column chromatography on silica gel (eluent, EtOAc:hexane-1:1) to yield the title compound, [1-(2-oxo-2-phenyl-ethylcarbamoyl)-ethyl]-carbamic acid benzyl ester.

$^1$H NMR (300 MHz, CDCl$_3$): δ 1.46 (3H, d), 4.39 (1H, m), 4.75 (2H, d), 5.13 (2H, d), 5.40 (1H, m), 7.03 (1 H, m), 7.36 (5H, m), 7.50 (2H, m), 7.63 (1H, m), 7.97(2H, m) MS(ES$^+$): 341.1 (100%).

Step B.
[1-(4-Phenyl-1H-imidazol-2-yl)-ethyl]-carbamic acid benzyl ester To a suspension of [1-(2-oxo-2-phenyl-ethylcarbamoyl)-ethyl]-carbamic acid benzyl ester (2.60 g, 7.64 mmol) in xylene (60 mL) was added NH$_4$OAc (10.3 g, 134 mmol) and HOAc (5 mL). The resulting mixture was heated at reflux for 7 h. After being cooled to room temperature, brine was added and the mixture was separated. The aqueous phase was extracted with EtOAc, and the combined organic phases were dried over Na$_2$SO$_4$ overnight. After filtration and concentration, the residue was purified by column chromatography on silica gel (eluent, EtOAc:hexane-1:1) to yield the title compound.

$^1$H NMR (300 MHz, CDCl$_3$): δ 1.65 (3H, d), 5.06 (1H, m), 5.14 (2H, q), 5.94 (1H, d), 7.32 (10H, m), 7.59 (2H, d) MS(ES$^+$): 322.2 (100%).

Step C. 1-(4-Phenyl-1H-imidazol-2-yl)-ethylamine

To a solution of [1-(4-phenyl-1H-imidazol-2-yl)-ethyl]-carbamic acid benzyl ester (1.5 g, 4.67 mmol) in methanol (25 mL) was added 10% palladium on carbon (0.16 g). The mixture was shaken in a hydrogenation apparatus at rt under a hydrogen atmosphere (10 psi) for 8 h. Filtration followed by evaporation to dryness under reduced pressure yielded the crude product 1-(4-phenyl-1H-imidazol-2-yl)-ethylamine.

$^1$H NMR (300 MHz, CDCl$_3$): δ 1.53 (3H, d), 4.33 (1H, q), 7.23 (3H, m), 7.37 (2H, m), 7.67 (2H, m) MS(ES$^+$): 188.1 (38%).

Step D. Isopropyl-[1-(4-phenyl-1H-imidazol-2-yl)-ethyl]-amine 1-(4-Phenyl-1H-imidazol-2-yl)-ethylamine (0.20 g, 1.07 mmol) and acetone (0.062 g, 1.07 mmol) were mixed in 1,2-dichloroethane (4 mL), followed by the addition of NaBH(OAc)$_3$ (0.34 g, 1.61 mmol). The resulting mixture was stirred at rt for 3 h. The reaction was quenched with saturated NaHCO$_3$ solution. The mixture was extracted with EtOAc and the combined extracts were dried over Na$_2$SO$_4$. Filtration followed by evaporation to dryness under reduced pressure yielded crude isopropyl-[1-(4-phenyl-1H-imidazol-2-yl)-ethyl]-amine, which was used for the next reaction without further purification.

$^1$H NMR (300 MHz, CDCl$_3$): δ 1.10 (3H, d), 1.18 (3H, d), 1.57 (3H, d), 2.86 (1H, m), 4.32 (1H, m), 7.24 (2H, m), 7.36 (2H, m), 7.69 (2H, m) MS(ES$^+$): 230.2 (100%).

Step E. (2-(4-Hydroxy-2,6-dimethyl-phenyl)-1-{isopropyl-[1-(4-phenyl-1H-imidazol-2-yl)-ethyl]-carbamoyl}-ethyl)-carbamic acid tert-butyl ester Into a solution of 2-tert-Butoxycarbonylamino-3-(4-hydroxy-2,6-dimethyl-phenyl)-propionic acid (0.18 g, 0.6 mmol) in DMF (7 mL) was added isopropyl-[1-(4-phenyl-1H-imidazol-2-yl)-ethyl]-amine (0.11 g, 0.5 mmol), 1-hydroxybenzotriazole (0.22 g, 1.6 mmol) and 1-[3-(dimethylamino)propyl]-3-ethylcarbodiimide hydrochloride (0.12 g, 0.6 mmol). The resulting mixture was stirred under an Argon atmosphere at room temperature overnight. The reaction mixture was extracted with EtOAc and the combined organic extracts were washed sequentially with saturated aqueous NaHCO$_3$ solution, 1N HCl, saturated aqueous NaHCO$_3$ solution, and brine. The organic phase was then dried over MgSO$_4$, filtered, and the filtrate was concentrated under reduced pressure. The resulting residue was purified by flash column chromatography (eluent: EtOAc) to yield the product (2-(4-hydroxy-2,6-dimethyl-phenyl)-1-{isopropyl-[1-(4-phenyl-1H-imidazol-2-yl)-ethyl]-carbamoyl}-ethyl)-carbamic acid tert-butyl ester.

MS(ES$^+$): 521.5 (100%).

Step F. 2-Amino-3-(4-hydroxy-2,6-dimethyl-phenyl)-N-isopropyl-N-[1-(4-phenyl-1H-imidazol-2-yl)-ethyl]-propionamide A solution of (2-(4-hydroxy-2,6-dimethyl-phenyl)-1-{isopropyl-[1-(4-phenyl-1H-imidazol-2-yl)-ethyl]-carbamoyl}-ethyl)-carbamic acid tert-butyl ester (0.13 g, 0.25 mmol) in trifluoroacetic acid (5 mL) was stirred at room tempertaure for 2 h. Upon removal of the solvents, the residue was purified by preparative LC and lyophilized to yield the TFA salt of the title compound as a white powder.

$^1$H NMR (300 MHz, CDCl$_3$): δ 0.48 (3H, d), 1.17 (3H, d), 1.76 (3H, d), 2.28 (6H, s), 3.19 (2H, m), 3.74 (1H, m), 4.70 (1H, m), 4.82 (1H, q), 6.56 (2H, s), 7.45 (4H, m), 7.74 (2H, m) MS(ES$^+$): 421.2 (100%).

EXAMPLE 4

(3,4-Dimethoxy-benzyl)-[1-(4-phenyl-1H-imidazol-2-yl)-ethyl]-amine

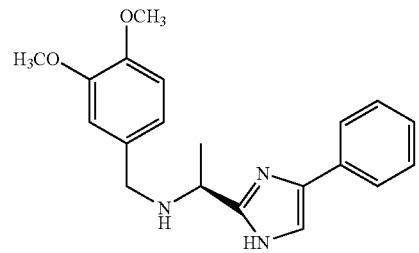

A solution of 1-(4-phenyl-1H-imidazol-2-yl)-ethylamine (0.061 g, 0.33 mmol) of Example 3, and 0.55 g (0.33 mmol)

of 3,4-dimethoxybenzaldehyde in 5 mL of anhydrous methanol was stirred at room temperature for 1 h and then cooled to about 0-10° C. in an ice bath for 1 h. The reaction was treated carefully with 0.019 g (0.49 mmol) of sodium borohydride in one portion and maintained at about 0-10° C. for 21 h. Cold 2M aqueous HCl was added dropwise (30 drops), the mixture was stirred for 5 min, and then partially concentrated in vacuo unheated. The residual material was taken up in EtOAc to yield a suspension that was treated with 5 mL of cold 3M aqueous NaOH and stirred vigorously until clear. The phases were separated and the aqueous layer was extracted three times additional with EtOAc. The combined extracts were dried over MgSO$_4$, filtered, and concentrated to yield (3,4-dimethoxy-benzyl)-[1-(4-phenyl-1H-imidazol-2-yl)-ethyl]-amine as a light yellow oil (HPLC: 87% @ 254 nm and 66% @ 214 nm).

MS (ES$^+$) (relative intensity): 338.1 (100) (M+1)

This sample was of sufficient quality to use in the next reaction without further purification.

EXAMPLE 5

5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid

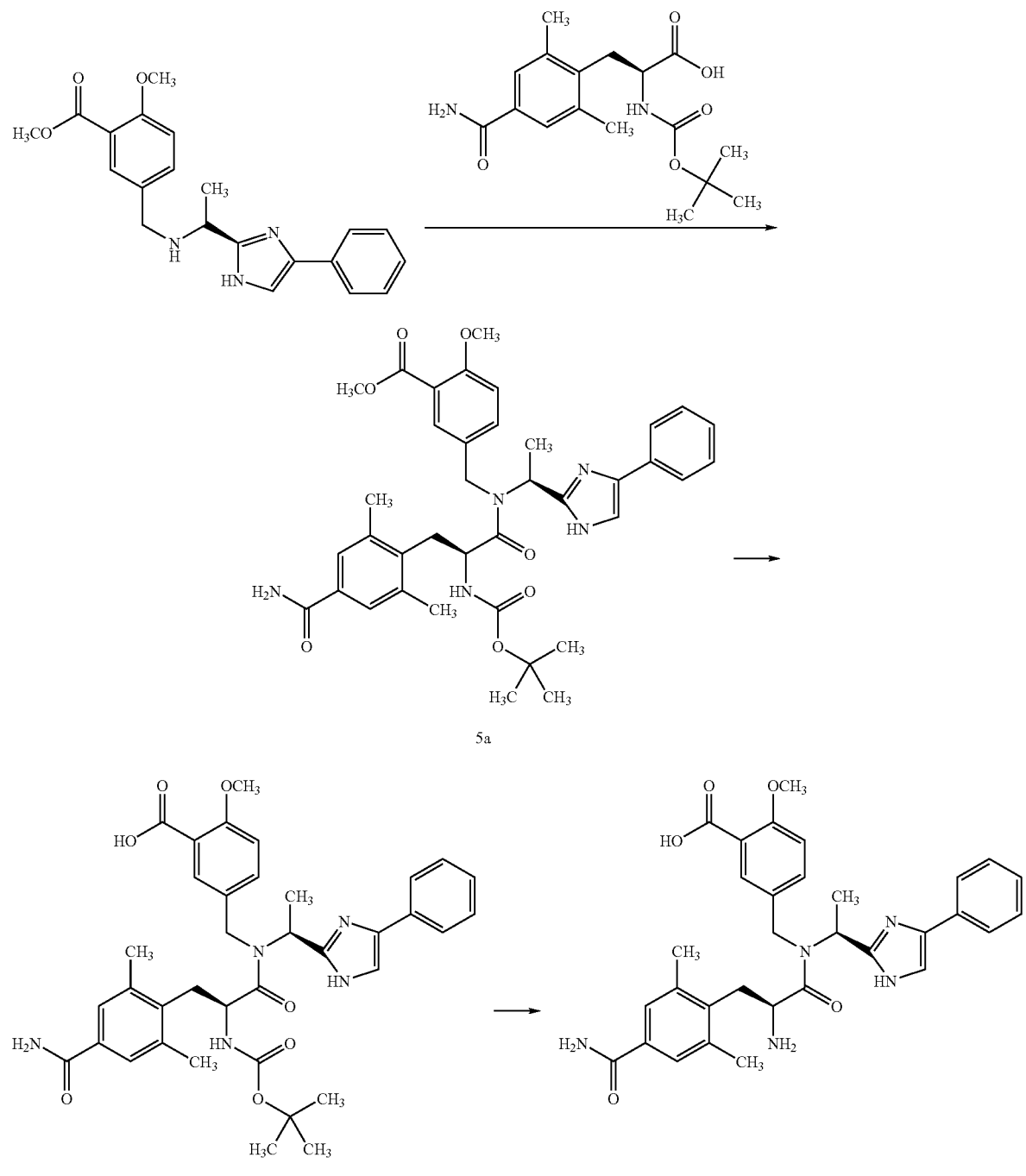

Step A. 2-Methoxy-5-{[1-(4-phenyl-1H-imidazol-2-yl)-ethylamino]-methyl}-benzoic acid methyl ester Using the procedures described for Example 4, substituting 5-formyl-2-methoxy-benzoic acid methyl ester (WO 02/22612) for 3,4-dimethoxybenzaldehyde, 2-methoxy-5-{[1-(4-phenyl-1H-imidazol-2-yl)-ethylamino]-methyl}-benzoic acid methyl ester was prepared.

Step B. 5-({[2-tert-Butoxycarbonylmethyl-3-(4-carbamoyl-2,6-dimethyl-phenyl)-propionyl]-[1-(4-phenyl-1H-imidazol-2-yl)-ethyl]-amino}-methyl)-2-methoxy-benzoic acid methyl ester Using the procedure of Example 3 for the conversion of Cpd 3d to Cpd 3e, substituting 2-methoxy-5-{[1-(4-phenyl-1H-imidazol-2-yl)-ethylamino]-methyl}-benzoic acid methyl ester for Cpd 3d and substituting 2-tert-Butoxycarbonylamino-3-(4-carbamoyl-2,6-dimethyl-phenyl)-propionic acid for 2-tert-Butoxycarbonylamino-3-(4-hydroxy-2,6-dimethyl-phenyl)-propionic acid, Cpd 5a was prepared.

Step C. 5-({[2-tert-butoxycarbonylamino-3-(4-carbamoyl-2,6-dimethyl-phenyl)-propionyl]-[1-(4-phenyl-1H-imidazol-2-yl)-ethyl]-amino}-methyl)-2-methoxy-benzoic acid 5-({[2-tert-Butoxycarbonylmethyl-3-(4-carbamoyl-2,6-dimethyl-phenyl)-propionyl]-[1-(4-phenyl-1H-imidazol-2-yl)-ethyl]-amino}-methyl)-2-methoxy-benzoic acid methyl ester was dissolved in an ice-chilled (0-10° C.), mixed solvent system of THF (10 mL) and MeOH (5 mL). A LiOH·H₂O/water suspension (2.48 M; 3.77 mL) was added dropwise, then the reaction was allowed to warm to room temperature and stirred overnight. The resulting mixture was cooled in an ice bath and the basic solution was neutralized with 2N citric acid until slightly acidic. The mixture was concentrated under reduced pressure to remove the volatile materials, after which time the remaining aqueous phase was extracted with EtOAc (3×26 mL). These combined organic phases were dried over MgSO₄, filtered, and concentrated under reduced pressure to yield a pale yellowish white solid. This crude material was dissolved in a 10% MeOH/CH₂Cl₂ solution and adsorbed onto 30 g of silica. The adsorbed material was divided and chromatographed on an ISCO normal phase column over two runs, using a 40 g Redi-Sep column for both runs. The solvent system was a gradient MeOH/CH₂Cl₂ system as follows: Initial 100% CH₂Cl₂, 98%-92% over 40 min; 90% over 12 min, and then 88% over 13 min. The desired product eluted cleanly between 44-61 min. The desired fractions were combined and concentrated under reduced pressure to yield 5-({[2-tert-butoxycarbonylamino-3-(4-carbamoyl-2,6-dimethyl-phenyl)-propionyl]-[1-(4-phenyl-1H-imidazol-2-yl)-ethyl]-amino}-methyl)-2-methoxy-benzoic acid, Cpd 5b, as a white solid.

Step D. 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid A portion of Cpd 5b (0.27 g, 0.41 mmol) was dissolved in EtOAc (39 mL)/THF (5 mL), filtered, and subsequently treated with gaseous HCl for 15 min. After completion of the HCl addition, the reaction was slowly warmed to room temperature and a solid precipitate formed. After 5 h the reaction appeared >97% complete by LC (@214 nm; 2.56 min.). The stirring was continued over 3 d, then the solid was collected and rinsed with a small amount of EtOAc. The resulting solid was dried under high vacuum under refluxing toluene for 2.5 h to yield Cpd 5c as a white solid di-HCl salt.

EXAMPLE 6

4-{2-Amino-2-[{1-[4-(2-cyano-phenyl)-1H-imidazol-2]-yl-ethyl}-(3,4-dimethoxy-benzyl)-carbamoyl]-ethyl}-3,5-dimethyl-benzamide

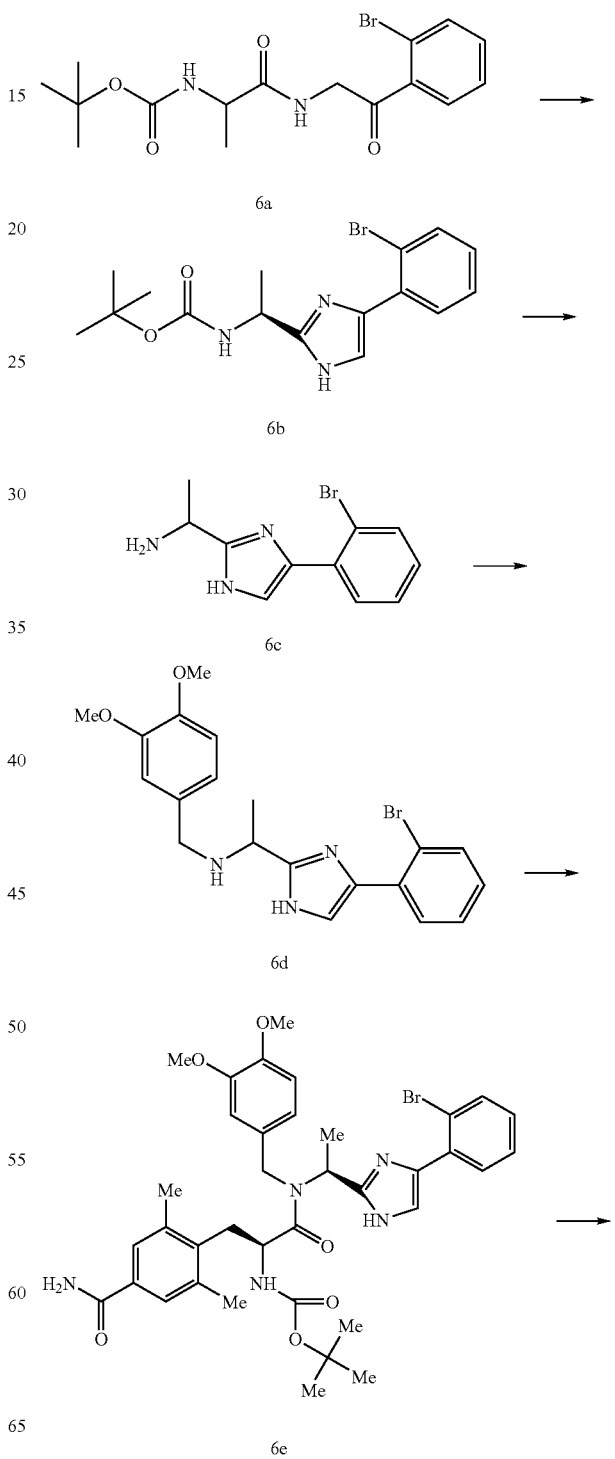

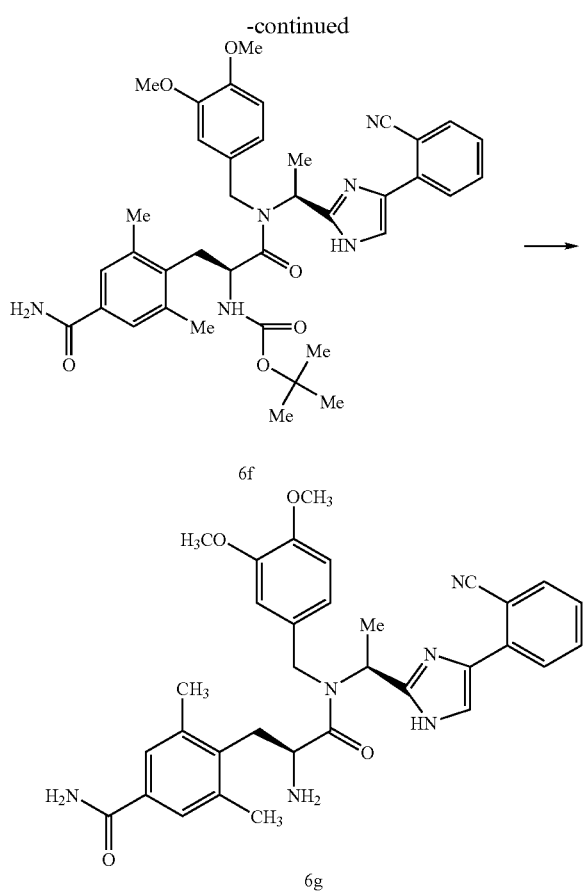

Step A: {1-[2-(2-Bromo-phenyl)-2-oxo-ethylcarbamoyl]-ethyl}-carbamic acid tert-butyl ester Compound 6a was prepared according to Example 3 using the appropriate reagents, starting materials and methods known to those skilled in the art.

Step B. {1-[4-(2-Bromo-phenyl)-1H-imidazol-2-yl]-ethyl}-carbamic acid tert-butyl ester Following the procedure described in Example 3 for the conversion of Compound 3a to Compound 3b, and using the appropriate reagents and methods known to those skilled in the art, Cpd 6b, was prepared.

Step C. 1-[4-(4-Bromo-phenyl)-1H-imidazol-2-yl]-ethylamine

Using the procedure described for the conversion of Cpd 3e to 3f, Compound 6c was prepared.

Step D. [1-[{1-[4-(2-Bromo-phenyl)-1H-imidazol-2-yl]-ethyl}-(3,4-dimethoxy-benzyl)-carbamoyl]-2-(4-carbamoyl-2,6-dimethyl-phenyl)-ethyl]-carbamic acid tert-butyl ester Using the procedure described in Example 5, STEP B, and substituting 1-[4-(4-bromo-phenyl)-1H-imidazol-2-yl]-ethylamine for 1-(4-phenyl-1H-imidazol-2-yl)-ethylamine, the product was prepared.

Step E. {2-(4-Carbamoyl-2,6-dimethyl-phenyl)-1-[{1-[4-(2-cyano-phenyl)-1H-imidazol-2-yl]-ethyl}-(3,4-dimethoxy-benzyl)-carbamoyl]-ethyl}-carbamic acid tert-butyl ester To a solution of [1-[{1-[4-(2-bromo-phenyl)-1H-imidazol-2-yl]-ethyl}-(3,4-dimethoxy-benzyl)-carbamoyl]-2-(4-carbamoyl-2,6-dimethyl-phenyl)-ethyl]-carbamic acid tert-butyl ester (294 mg; 0.4 mmol) in DMF (2 mL) was added $Zn(CN)_2$ (28 mg; 0.24 mmol). The resulting mixture was degassed with Argon for 5 min, then $Pd(PPh_3)_4$ (92 mg; 0.08 mmol) was added neat, and the system was immediately warmed to 100° C. After heating for 6 h, the reaction was cooled to room temperature and partitioned between EtOAc and water. The organic phase was dried over $Na_2SO_4$, filtered, and concentrated under reduced pressure. The crude material was subjected to reverse phase HPLC (water/acetonitrile/ 0.1% TFA). The fractions of interest were combined, basified with saturated aqueous $NaHCO_3$ and extracted twice with EtOAc. The EtOAc extracts were combined, dried over $Na_2SO_4$, filtered, and concentrated to yield {2-(4-carbamoyl-2,6-dimethyl-phenyl)-1-[{(1-[4-(2-cyano-phenyl)-1H-imidazol-2-yl]-ethyl}-(3,4-dimethoxy-benzyl)-carbamoyl]-ethyl}-carbamic acid tert-butyl ester (HPLC: 96% @ 254 nm and 97% @ 214 nm). This sample was of sufficient quality to use in the next reaction without further purification.

Step F. 4-{2-Amino-2-[{1-[4-(2-cyano-phenyl)-1H-imidazol-2-yl]-ethyl}-(3,4-dimethoxy-benzyl)-carbamoyl]-ethyl}-3,5-dimethyl-benzamide {2-(4-carbamoyl-2,6-dimethyl-phenyl)-1-[{1-[4-(2-cyano-phenyl)-1H-imidazol-2-yl]-ethyl}-(3,4-dimethoxy-benzyl)-carbamoyl]-ethyl}-carbamic acid tert-butyl ester may be BOC-deprotected using the procedure described in Example 3 for the conversion of Cpd 3e to Cpd 3f to yield the title compound.

EXAMPLE 7

3-(2-{1-[[2-Amino-3-(4-carbamoyl-2,6-dimethyl-phenyl)-propionyl]-(3,4-dimethoxy-benzyl)-amino]-ethyl}-1H-imidazol-4-yl)-benzoic acid

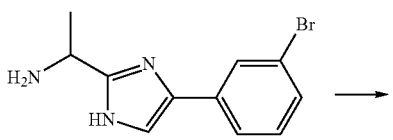

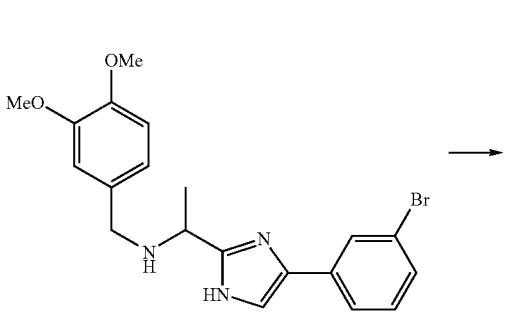

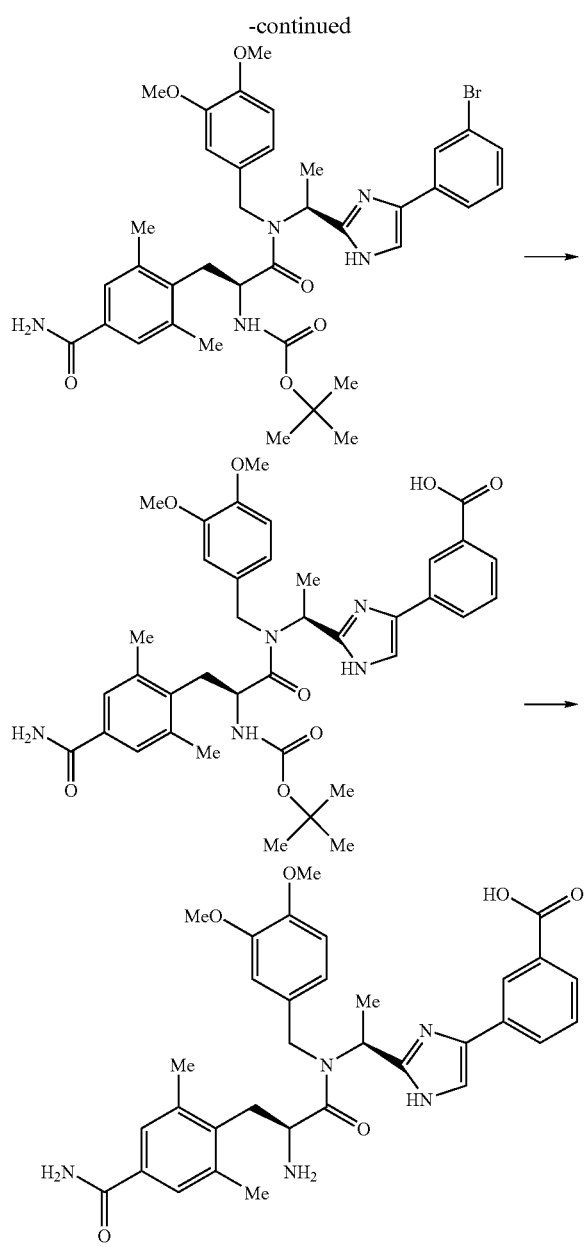

Step A. 1-[4-(3-Bromo-phenyl)-1H-imidazol-2-yl]-ethylamine

Using the procedure described in Example 6, and the appropriately substituted starting materials and reagents, 1-[4-(3-bromo-phenyl)-1H-imidazol-2-yl]-ethylamine was prepared.

Step B. {1-[4-(3-Bromo-phenyl)-1H-imidazol-2-yl]-ethyl}-(3,4-dimethoxy-benzyl)-amine Using the procedure described in Example 4, and substituting 1-[4-(3-bromo-phenyl)-1H-imidazol-2-yl]-ethylamine for 1-(4-phenyl-1H-imidazol-2-yl)-ethylamine, the product was prepared.

Step C. [1-[{1-[4-(3-Bromo-phenyl)-1H-imidazol-2-yl]-ethyl}-(3,4-dimethoxy-benzyl)-carbamoyl]-2-(4-carbamoyl-2,6-dimethyl-phenyl)-ethyl]-carbamic acid tert-butyl ester Using the procedure of Example 3 for the conversion of Cpd 3d to Cpd 3e, substituting {1-[4-(3-Bromo-phenyl)-1H-imidazol-2-yl]-ethyl}-(3,4-dimethoxy-benzyl)-amine for Cpd 3d and substituting 2-tert-Butoxycarbonylamino-3-(4-carbamoyl-2,6-dimethyl-phenyl)-propionic acid for 2-tert-Butoxycarbonylamino-3-(4-hydroxy-2,6-dimethyl-phenyl)-propionic acid, the product was prepared.

Step D. 3-(2-{1-[[2-tert-Butoxycarbonylamino-3-(4-carbamoyl-2,6-dimethyl-phenyl)-propionyl]-(3,4-dimethoxy-benzyl)-amino]-ethyl}-1H-imidazol-4-yl)-benzoic acid To a solution of [1-[{1-[4-(3-bromo-phenyl)-1H-imidazol-2-yl]-ethyl}-(3,4-dimethoxy-benzyl)-carbamoyl]-2-(4-carbamoyl-2,6-dimethyl-phenyl)-ethyl]-carbamic acid tert-butyl ester (290 mg; 0.40 mmol) in DMF (5 mL) was added $K_2CO_3$ (262 mg; 1.9 mmol) and the resulting mixture was degassed with Argon for 5 min. At this time, $Pd(OAc)_2$ (8.9 mg; 0.04 mmol) and 1,1-bis(diphenylphosphino)ferrocene (46 mg; 0.083 mmol) were added. Carbon monoxide was then bubbled through the resulting mixture for 10 min at room temperature, the reaction was capped, and warmed to 100° C. for 6 h. After cooling to room temperature the mixture was partitioned between EtOAc and water, filtered through Celite, and then separated. The aqueous phase was then washed with a second portion of EtOAc. The aqueous phase was then acidified to pH 5 with 2N citric acid and the resulting aqueous solution extracted with EtOAc (4×). These latter EtOAc extracts were combined, dried over $Na_2SO_4$, filtered, and concentrated under reduced pressure to yield the crude product (HPLC: 87% at 254 nm).

Step E. 3-(2-{1-[[2-Amino-3-(4-carbamoyl-2,6-dimethyl-phenyl)-propionyl]-(3,4-dimethoxy-benzyl)-amino]-ethyl}-1H-imidazol-4-yl)-benzoic acid 3-(2-{1-[[2-tert-Butoxycarbonylamino-3-(4-carbamoyl-2,6-dimethyl-phenyl)-propionyl]-(3,4-dimethoxy-benzyl)-amino]-ethyl}-1H-imidazol-4-yl)-benzoic acid may be BOC-de-protected using the procedure described in Example 3 for the conversion of Cpd 3e to Cpd 3f to yield the title compound.

EXAMPLE 8

4-(2-Amino-2-{[2-hydroxy-1-(4-phenyl-1H-imidazol-2-yl)-ethyl]-isopropyl-carbamoyl}-ethyl)-3,5-dimethyl-benzamide

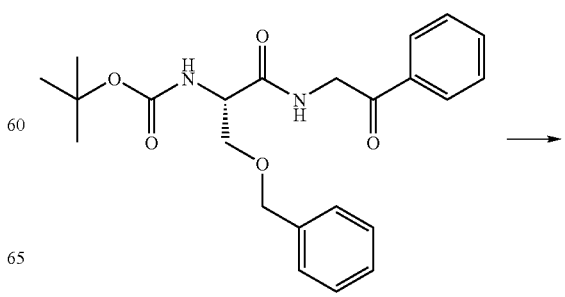

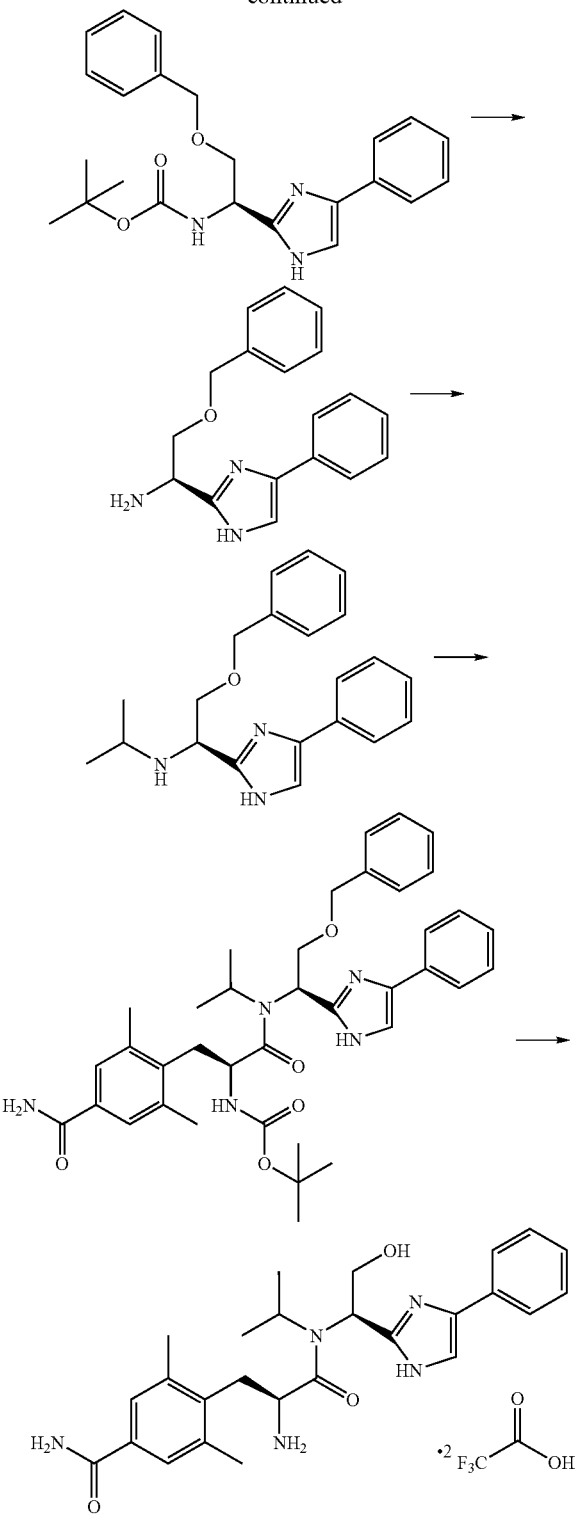

Step A. [2-Benzyloxy-1-(2-oxo-2-phenyl-ethylcarbamoyl-ethyl]-carbamic acid tert butyl ester The product was prepared using the procedure described in Example 3 and substituting N-α-BOC-L-serine benzyl ester for N-α-CBZ-L-alanine.

Step B. [2-Benzyloxy-1-(4-phenyl-1H-imidazol-2-yl-ethyl]-carbamic acid tert butyl ester By the procedure described in Example 3 for the conversion of Cpd 3a to Cpd 3b, [2-benzyloxy-1-(2-oxo-2-phenyl-ethylcarbamoyl-ethyl]-carbamic acid tert butyl ester was converted to the product.

Step C. [2-Benzyloxy-1-(4-phenyl-1H-imidazol-2-yl-ethylamine

[2-benzyloxy-1-(4-phenyl-1H-imidazol-2-yl-ethyl]-carbamic acid tert butyl ester may be BOC-deprotected using the procedure described in Example 3 for the conversion of Cpd 3e to Cpd 3f to give the product.

Step D. [2-Benzyloxy-1-(4-phenyl-1H-imidazol-2-yl-ethyl]-isopropyl-amine

By the procedure described in Example 3 for the conversion of Cpd 3c to Cpd 3d, [2-benzyloxy-1-(4-phenyl-1H-imidazol-2-yl-ethylamine was converted to the product.

Step E. [1-{[2-Benzyloxy-1-(4-phenyl-1H-imidazol-2-yl)-ethyl]-isopropyl-carbamoyl}-2-(4-carbamoyl-2,6-dimethyl-phenyl)-ethyl]-carbamic acid tert-butyl ester Using the procedure of Example 3 for the conversion of Cpd 3d to Cpd 3e, substituting [2-benzyloxy-1-(4-phenyl-1H-imidazol-2-yl-ethyl]-isopropyl-amine for Cpd 3d and substituting 2-tert-Butoxycarbonylamino-3-(4-carbamoyl-2,6-dimethyl-phenyl)-propionic acid for 2-tert-butoxycarbonylamino-3-(4-hydroxy-2,6-dimethyl-phenyl)-propionic acid, the product was prepared.

Step F. 4-(2-Amino-2-{[2-hydroxy-1-(4-phenyl-1H-imidazol-2-yl)-ethyl]-isopropyl-carbamoyl}-ethyl)-3,5-dimethyl-benzamide (TFA salt).

A solution of [1-{[2-benzyloxy-1-(4-phenyl-1H-imidazol-2-yl)-ethyl]-isopropyl-carbamoyl}-2-(4-carbamoyl-2,6-dimethyl-phenyl)-ethyl]-carbamic acid tert-butyl ester, (0.287 g, 0.439 mmol), in chloroform (10 mL) was cooled in an ice bath and treated with 0.62 mL (4.4 mmol) of iodotrimethylsilane. The reaction, which immediately clouded, was warmed slowly to room temperature while stirring. After 16 h, the reaction was cooled in an ice bath to 5-10° C. and treated with 100 mL of MeOH. The quenched mixture was stirred at 5-10° C. for 30 min, removed from the ice bath and stirred for an additional 30 min, and concentrated in vacuo to yield an orange residue that was subjected to reverse phase HPLC (water/acetonitrile/0.1% TFA). The fractions of interest were combined and the sample was lyophilized to yield 4-(2-amino-2-{[2-hydroxy-1-(4-phenyl-1H-imidazol-2-yl)-ethyl]-isopropyl-carbamoyl}-ethyl)-3,5-dimethyl-benzamide (TFA salt) as a white powder (HPLC: 99% @ 254 nm and 100% @ 214 nm)

MS (ES$^+$) (relative intensity): 464.1 (100) (M+1).

EXAMPLE 9

(S)-2-tert-Butoxycarbonylamino-3-(2,6-dimethyl-4-trifluoromethanesulfonylphenyl)-propionic acid methyl ester

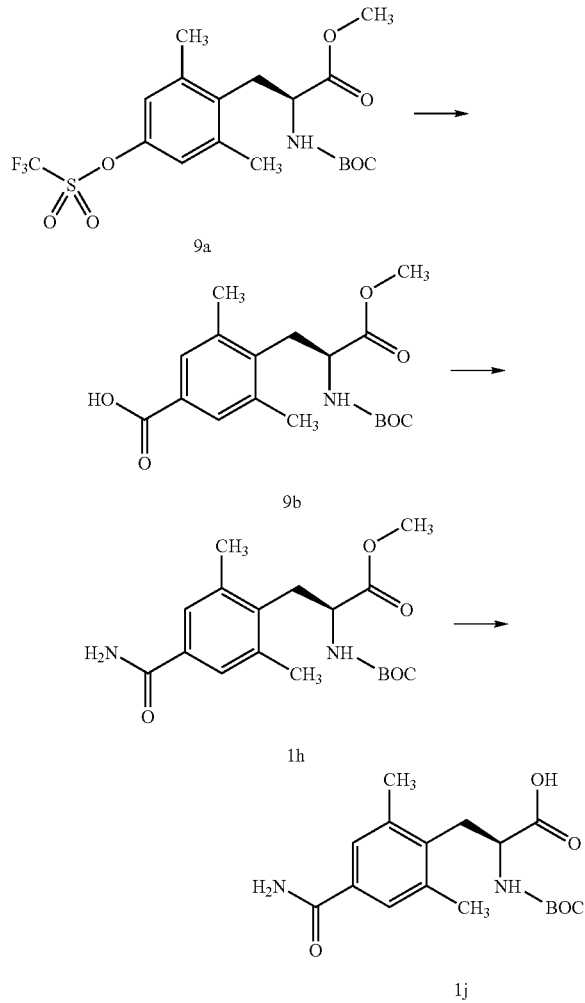

Step A. (S)-2-tert-Butoxycarbonylamino-3-(2,6-dimethyl-4-trifluoromethanesulfonylphenyl)-propionic acid methyl ester Into a cool solution of Boc-L-(2,6-diMe)Tyr-OMe (7.0 g, 21.6 mmol; Sources: Chiramer or RSP AminoAcidAnalogues) and N--phenyltrifluoromethanesulfonimide (7.9 g, 22.0 mmol) in dichloromethane (60 mL) was added triethylamine (3.25 mL, 23.3 mmol). The resulting solution was stirred at 0° C. for 1 h and slowly warmed to room temperature. Upon completion, the reaction was quenched by addition of water. The separated organic phase was washed with 1 N NaOH aqueous solution, water and dried over $Na_2SO_4$ overnight. After filtration and evaporation, the residue was purified by flash column chromatography (eluent: EtOAc-hexane: 3:7) to yield the desired product as a clear oil.

$^1$H NMR (300 MHz, $CDCl_3$): δ 1.36 (9H, s), 2.39 (6H, s), 3.06 (2H, d, J=7.7 Hz), 3.64 (3H, s), 4.51-4.59 (1H, m), 5.12 (1H, d, J=8.5 Hz), 6.92 (2H, s)

MS (ES+) (relative intensity): 355.8 (100) (M-Boc)$^+$.

Step B. (S)-4-(2-tert-Butoxycarbonylamino-2-methoxycarbonylethyl)-3,5-dimethylbenzoic acid To a suspension of (S)-2-tert-butoxycarbonylamino-3-(2,6-dimethyl-4-trifluoromethanesulfonylphenyl)-propionic acid methyl ester (9.68 g, 21.3 mmol), $K_2CO_3$ (14.1 g, 0.102 mol), Pd(OAc)$_2$ (0.48 g, 2.13 mmol) and 1,1'-bis(diphenylphosphino)ferrocene (2.56 g, 4.47 mmol) in DMF (48 mL) was bubbled in gaseous CO for 15 min. The mixture was heated to 60° C. for 8 h with a CO balloon. The cool mixture was partitioned between $NaHCO_3$ and EtOAc, and filtered. The aqueous layer was separated, acidified with 10% citric acid aqueous solution, extracted with EtOAc, and finally dried over $Na_2SO_4$. Filtration and concentration of the filtrate resulted in a residue. The residue was recrystallized from EtOAc-hexanes to yield the desired product.

$^1$H NMR (300 MHz, $CDCl_3$): δ 1.36 (9H, s), 2.42 (6H, s), 3.14 (2H, J=7.4 Hz), 3.65 (3H, s), 4.57-4.59 (1H, m), 5.14 (1H, d, J=8.6 Hz), 7.75 (2H, s)

MS(ES+) (relative intensity): 251.9 (100) (M-Boc)+.

Step C. (S)-2-tert-Butoxycarbonylamino-3-(4-carbamoyl-2,6-dimethylphenyl)propionic acid methyl ester Into a stirring solution of (S)-4-(2-tert-butoxycarbonylamino-2-methoxycarbonylethyl)-3,5-dimethylbenzoic acid (3.00 g, 8.54 mmol), PyBOP (6.68 g, 12.8 mmol) and HOBt (1.74 g, 12.8 mmol) in DMF (36 mL) was added DIPEA (5.96 mL, 34.2 mmol) and $NH_4Cl$ (0.92 g, 17.1 mmol). The resulting mixture was stirred at rt for 40 min before being partitioned between aqueous $NH_4Cl$ solution and EtOAc. The separated organic phase was washed sequentially with 2N citric acid aqueous solution, saturated aqueous $NaHCO_3$ solution, and brine, then dried over $Na_2SO_4$ overnight. After filtration and concentration, the residue was purified by flash column chromatography (eluent: EtOAc) to yield the product.

$^1$H NMR (300 MHz, $CDCl_3$): δ 1.36.(9H, s), 2.39 (6H, s),-3.11 (2H, J=7.2 Hz), 3.65 (3H, s), 4.53-4.56 (1H, m), 5.12 (1H, d, J=8.7 Hz), 5.65 (1H, br s), 6.09 (1H, br s), 7.46 (2H, s)

MS(ES+) (relative intensity): 250.9 (100) (M-Boc)$^+$.

Step D. (S)-2-tert-Butoxycarbonylamino-3-(4-carbamoyl-2,6-dimethylphenyl)propionic acid Into an ice-cooled solution of methyl ester from Step C (2.99 g, 8.54 mmol) in THF (50 mL) was added an aqueous LiOH solution (1 N, 50 mL) and stirred at 0° C. Upon consumption of the starting materials, the organic solvents were removed and the aqueous phase was neutralized with cooled 1N HCl at 0° C., and extracted with EtOAc, and dried over $Na_2SO_4$ overnight. Filtration and evaporation to dryness yielded the title acid (S)-2-tert-butoxycarbonylamino-3-(4-carbamoyl-2,6-dimethylphenyl)propionic acid.

$^1$H NMR (300 MHz, DMSO-d$_6$): δ 1.30 (9H, s), 2.32 (6H, s), 2.95(1H, dd, J=8.8, 13.9 Hz), 3.10 (1H, dd, J=6.2, 14.0 Hz), 4.02-4.12 (1H, m), 7.18-7.23 (2H, m), 7.48 (2H, s), 7.80 (1H, s)

MS(ES+) (relative intensity): 236.9 (6) (M-Boc)$^+$.

EXAMPLE 10

(Z)-2-Benzyloxycarbonylamino-3-(4-carbamoyl-2,6-dimethyl-phenyl)acrylic acid methyl ester

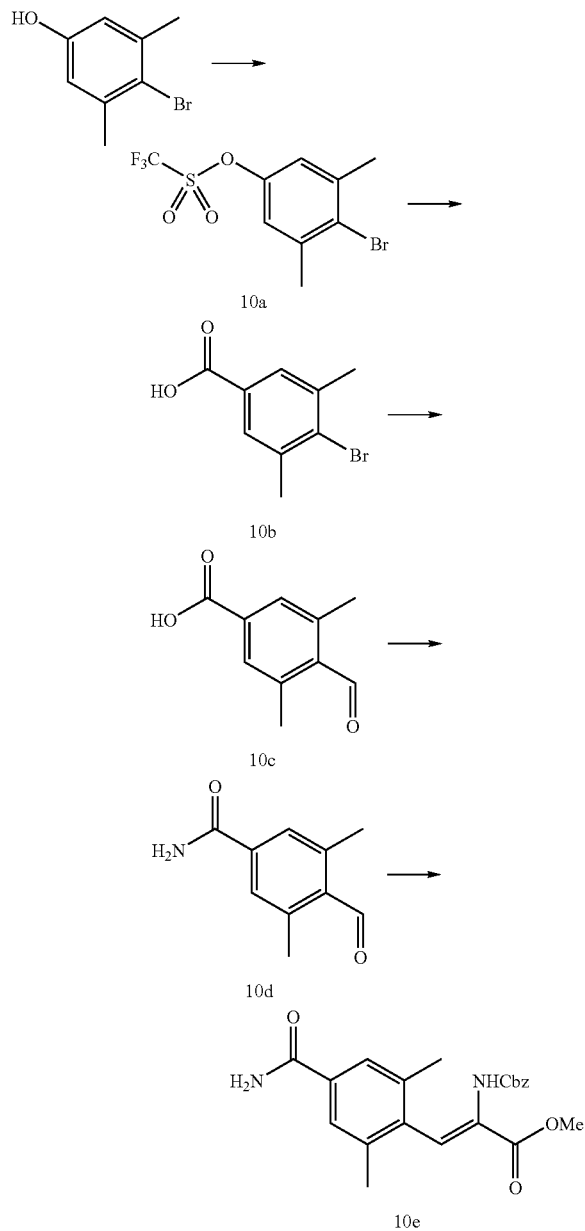

Step A. Trifluoromethanesulfonic acid 4-bromo-3,5-dimethyl-phenyl ester

To a cooled (0° C.) solution of 4-bromo-3,5-dimethylphenol (3.05 g, 15.2 mmol) in pyridine (8 mL) was added trifluoromethanesulfonic anhydride (5.0 g, 17.7 mmol) dropwise. After completion of addition, the resulting mixture was stirred at 0° C. for 15 min and at room temperature overnight. The reaction was then quenched by addition of water, then extracted with EtOAc. The EtOAc extracts were washed with water, 2N HCl (2×), brine and dried over MgSO$_4$. Filtration and evaporation to dryness yield the product (10a) as a colorless oil.

$^1$H NMR (300 MHz, CDCl$_3$): δ 2.45 (6H, s), 7.00 (2H, s).

Step B. 4-Bromo-3,5-dimethylbenzoic acid

Into a solution of trifluoro-methanesulfonic acid 4-bromo-3,5-dimethyl-phenyl ester (6.57 g, 19.7 mmol) in DMF (65 mL) were added K$_2$CO$_3$ (13.1 g, 94.7 mmol), Pd(OAc)$_2$ (0.44 g, 1.97 mmol) and 1,1'-bis(diphenylphosphino)ferrocene (2.29 g, 4.14 mmol). The resulting mixture was bubbled in gaseous CO for 10 min and was then heated to 60° C. for 7.5 h with a CO balloon. The cooled mixture was partitioned between aqueous NaHCO$_3$ and EtOAc, and filtered. The aqueous phase layer was separated, acidified with aqueous 6N HCl, extracted with EtOAc, and then dried over Na$_2$SO$_4$. Filtration and concentration of the filtrate resulted in the crude product (10b) as a brown residue, which was used in the next step without further purification.

Step C. 4-Formyl-3,5-dimethyl-benzoic acid

A solution of 4-bromo-3,5-dimethylbenzoic acid (0.92 g, 4 mmol) in THF (10 mL) was cooled down to −100° C. with N$_2$(I)-Et$_2$O bath and added n-butyllithium (1.6 M in hexanes, 5 mL, 8 mmol) slowly. After completion of addition, the reaction mixture was warmed to −78° C. and DMF (0.74 mL, 8 mmol) was added dropwise. The resulting mixture was stirred at −78° C. for 1.5 h and allowed to warm to −20° C., followed by the addition of 2N aqueous HCl (30 mL). The organic phase was separated and the aqueous phase was extracted with EtOAc, the combined organic phases were dried over MgSO$_4$. The solvent was removed and the resulting residue was purified by flash column chromatography (eluent: EtOAc-hexanes-1:1) to yield 4-formyl-3,5-dimethyl-benzoic acid (10c).

$^1$H NMR (300 MHz, CDCl$_3$): δ 2.65 (6H, s), 7.82 (2H, s), 10.67(1H, s).

Step D. 4-Formyl-3,5-dimethyl-benzamide

To a solution of 4-formyl-3,5-dimethyl-benzoic acid (0.15 g, 0.85 mmol) in DMF (6 mL) were added PyBOP (1.0 g, 1.92 mmol), HOBt (0.26 g, 1.92 mmol), DIPEA (0.89 mL, 5.12 mmol) and NH$_4$Cl (0.14 g, 2.56 mmol). The resulting mixture was stirred at room temperature for 1 h, and quenched by addition of brine, then extracted with EtOAc. The organic phase was washed with 2N aqueous HCl, saturated NaHCO$_3$, brine and then dried over MgSO$_4$. The solvent was removed to yield the crude product (10d), which was used in the next step without further prurification.

Step E. (Z)-2-Benzyloxycarbonylamino-3-(4-carbamoyl-2,6-dimethyl-phenyl)acrylic acid methyl ester Into a solution of N-(benzyloxycarbonyl)-a-phosphinoglycine trimethyl ester (0.46 g, 1.4 mmol) in DCM (5 mL) was added DBU (0.21 mL, 1.4 mmol). After stirring for 10 min, a solution of the above made 4-formyl-3,5-dimethyl-benzamide in DCM (5 mL) was added dropwise; The resulting mixture was stirred at room temperature for 5.5 h and the solvent was removed by rotary evaporation. The residue was dissolved in EtOAc and washed with 1N aqueous HCl, brine and then dried over MgSO$_4$. The solvent was removed and residue purified by flash column chromatography (eluent: EtOAc-hexanes~1:1) to yield (Z)-2-tert-butoxycarbonylamino-3-(4-carbamoyl-2,6-dimethyl-phenyl)acrylic acid methyl ester (10e) as a white solid.

MS(ES$^+$) (relative intensity): 383.4 (10%)(M+1).

EXAMPLE 11

(Z)-2-Benzyloxycarbonylamino-3-(4-carbamoyl-2,6-dimethyl-phenyl)acrylic acid methyl ester

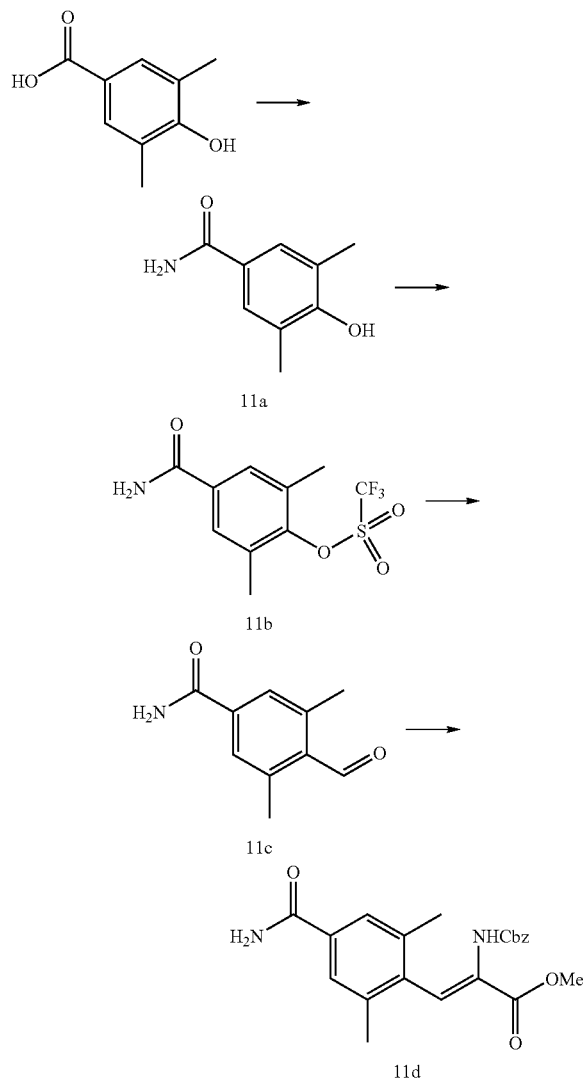

Step A. 4-Hydroxy-3,5-dimethyl-benzamide

Using the procedure described in Example 10, Step D, 4-hydroxy-3,5-dimethyl-benzamide (11a) was prepared as a yellowish solid.

$^1$H NMR (300 MHz, CDCl$_3$): δ 2.82 (6H, s), 5.51 (1H, br s), 5.90 (1H, br s), 7.48 (2H, s);

MS(ES$^+$) (relative intensity): 166.2 (8%)(M+1).

Step B. Trifluoromethanesulfonic acid 4-carbamoyl-2,6-dimethyl-phenyl ester

Into a solution of 4-hydroxy-3,5-dimethyl-benzamide (3.72 g, 22.5 mmol) and N-phenyltrifluoromethanesulfoniunimide (9.4 g, 25 mmol) in DCM (80 mL) was added TEA (3.48 mL, 25 mmol) at room temperature, then the resulting mixture was stirred at room temperature overnight. After the reaction was quenched by addition of water, the separated organic phase was washed with 1N NaOH, water and then dried over MgSO$_4$. The solvent was removed and the residue purified by flash column chromatography (eluent: EtOAc-hexanes~1:1) to yield trifluoromethanesulfonic acid 4-carbamoyl-2,6-dimethyl-phenyl ester (11b) as a white solid.

$^1$H NMR (300 MHz, CDCl$_3$): δ 2.42 (6H, s), 6.28 (2H, br s), 7.57 (2H, s)

MS(ES$^+$) (relative intensity): 298.1 (63%)(M+1).

Step C. 4-Formyl-3,5-dimethyl-benzamide

Into a solution of trifluoro-methanesulfonic acid 4-carbamoyl-2,6-dimethyl-phenyl ester (1.49 g, 5 mmol), Pd(OAc)2 (0.037 g, 0.15 mmol), DPPP (0.062 g, 0.15 mmol) and TEA (1.74 mL, 12.5 mmol) in DMF (25 mL) was bubbled CO (gas) for 10 min, then triethylsilane (1.6 mL, 10 mmol) was added. The resulting mixture was stirred at 75° C. under a CO gas balloon for 6.5 hr. After cooling to room teperature, the reaction was quenched by addition of water, then extracted with EtOAc. The EtOAc extracts were washed with water, brine and then dried over MgSO$_4$. After filtration and evaporation, the residue was purified by column chromatograpghy (eluent, EtOAc-hexanes~1:1) to yield 4-formyl-3,5-dimethyl-benzamide (11c) as a yellowish solid.

$^1$H NMR (300 MHz, CDCl$_3$): δ 2.65 (6H, s), 5.75 (1H, brs), 6.13 (1H, br s), 7.52 (2H, s), 10.64 (1H, s).

Step D. (Z)-2-Benzyloxycarbonylamino-3-(4-carbamoyl-2,6-dimethyl-phenyl)acrylic acid methyl ester The title compound was prepared as described in Example 10, Step E.

EXAMPLE 12

Optical Rotation Measurements

The optical rotation of a representative sample of the compound of formula (Ia), prepared as in Example 1, was measured as [α] D=−12 (c 1.5, MeOH).

The optical rotation of a representative sample of the compound of formula (1a), prepared as in Example 9, from commercially purchased (S)-N-BOC-Tyr-OMe was measured as [α] D=−10.8 (c 1.7, MeOH).

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A process for the preparation of a compound of formula (I)

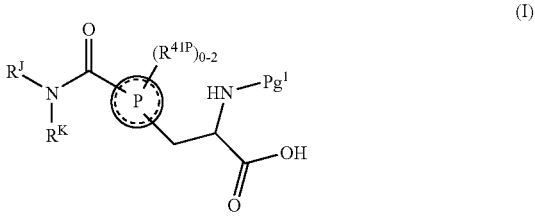

wherein

is phenyl;
each $R^{41P}$ is independently selected from $C_{1-6}$alkyl, $C_{1-6}$alkoxy or fluoro;
$R^J$ and $R^K$ are each independently selected from hydrogen or $C_{1-4}$alkyl; alternatively, $R^J$ and $R^K$ are taken together with the nitrogen atom to which they are bound to form a five to seven membered heterocyclyl;
$Pg^1$ is a nitrogen protecting group;
comprising

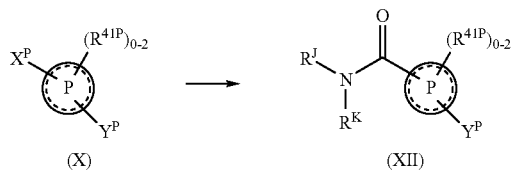

reacting a compound of formula (X), wherein $X^P$ is selected from OH, CN, —CO$_2$H, —C(O)—Cl or —C(O)—OC$_{1-4}$alkyl and wherein $y^P$ is selected from Br, Cl or I, to yield the corresponding compound of formula (XII);

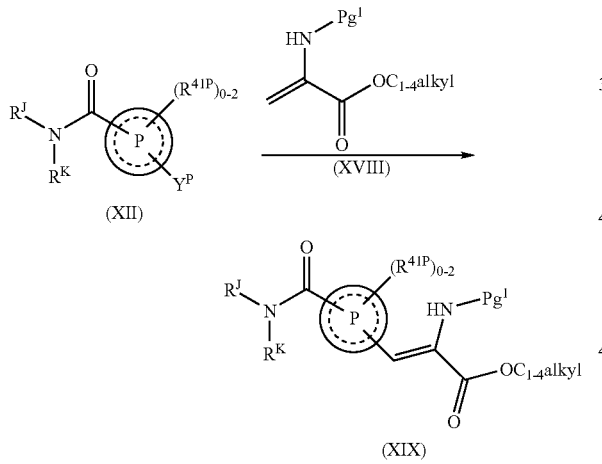

reacting the compound of formula (XII) with a compound of formula (XVIII); in the presence of palladium catalyst; in the presence of an organic or inorganic base; in an organic solvent; at a temperature greater than about room temperature; to yield the corresponding compound of formula (XIX);

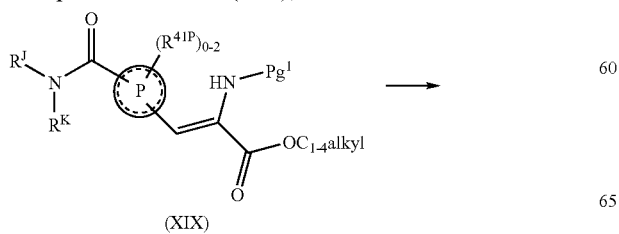

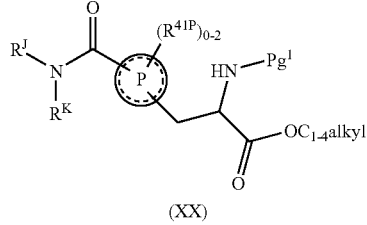

reacting the compound of formula (XIX) with hydrogen or a source of hydrogen; in the presence of a catalyst; in a solvent; at a temperature greater than about room temperature; to yield the corresponding compound of formula (XX);

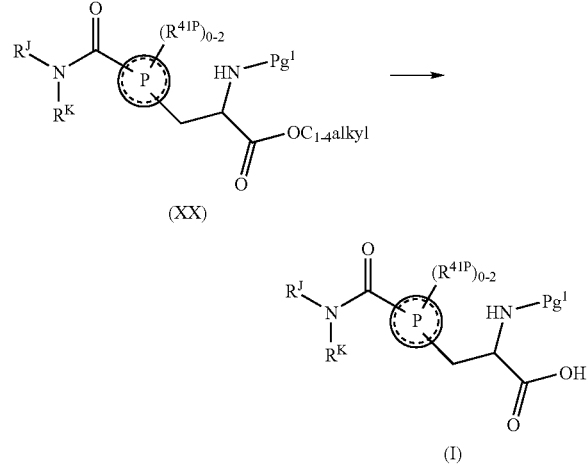

reacting the compound of formula (XX) with an aqueous base; in an organic solvent; to yield the corresponding compound of formula (I).

2. The process as in claim 1, wherein

is substituted with a $R^{41P}$ group at 2-position and a second $R^{41P}$ group at the 4- position;
each $R^{41P}$ is independently selected from $C_{1-2}$alkyl, $C_{1-2}$alkoxy or fluoro;
$R^J$ and $R^K$ are each independently selected from hydrogen or $C_{1-4}$alkyl; alternatively, $R^J$ and $R^K$ are taken together with the nitrogen atom to which they are bound to form a five to seven membered heterocyclyl; and
$Pg^1$ is a nitrogen protecting group.

3. The process as in claim 1, wherein

is substituted with a $R^{41P}$ group at the 2-position and a second $R^{41P}$ group at the 4-position; each $R^{41P}$ is methyl; $R^J$ and $R^K$ are each hydrogen; and $Pg^1$ is a t-butoxycarbonyl.

4. A process for the preparation of a compound of formula (I)

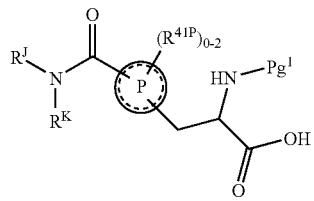

wherein

is phenyl;

each $R^{41P}$ is independently selected from $C^{1-6}$alkyl, $C^{1-6}$alkoxy or fluoro;

$R^J$ and $R^K$ are each independently selected from hydrogen or $C^{1-4}$alkyl; alternatively, $R^J$ and $R^K$ are taken together with the nitrogen atom to which they are bound to form a five to seven membered heterocyclyl;

$Pg^1$ is a nitrogen protecting group;

comprising

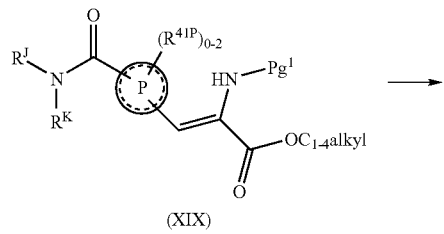

reacting the compound of formula (XIX) with hydrogen or a source of hydrogen; in the presence of a catalyst; in a solvent; at a temperature greater than about room temperature; to yield the corresponding compound of formula (XX);

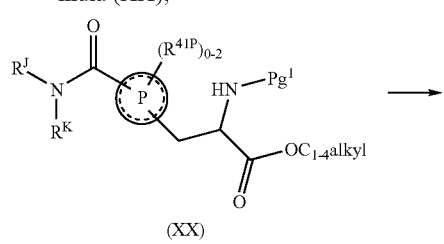

-continued

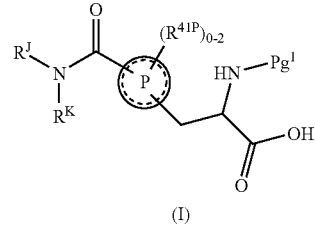

reacting the compound of formula (XX) with an aqueous base; in an organic solvent; to yield the corresponding compound of formula (I).

5. A process for the preparation of a compound of formula (Ia)

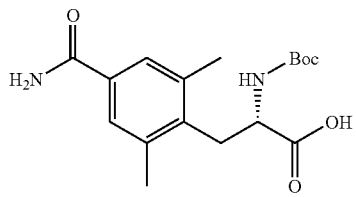

comprising

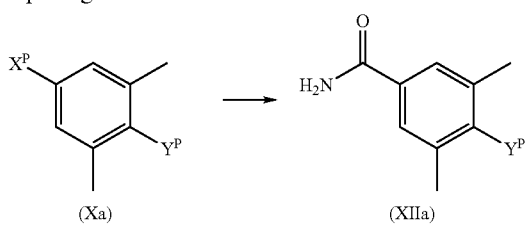

reacting a compound of formula (Xa), wherein $X^P$ is selected from OH, CN, —$CO_2H$, —C(O)—Cl or —C(O)—$OC_{1-4}$alkyl and wherein $Y^P$ is selected from Br, Cl or I, to yield the corresponding compound of formula (XIIa);

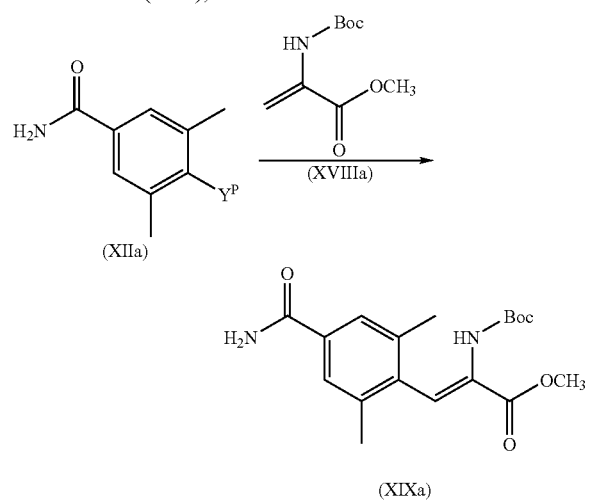

reacting the compound of formula (XIIa) with a compound of formula (XVIIIa); in the presence of palladium catalyst; in the presence of an organic or inorganic base; in an organic solvent; at a temperature greater than about room temperature; to yield the corresponding compound of formula (XIXa);

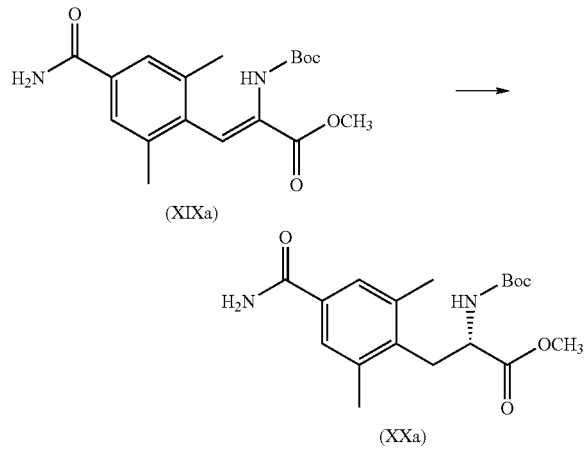

reacting compound of formula (XIXa) with hydrogen gas, at a pressure greater than about 500 psi; in the presence of a chiral catalyst; at a temperature greater than about room temperature; in an organic solvent; to yield the corresponding compound of formula (XXa);

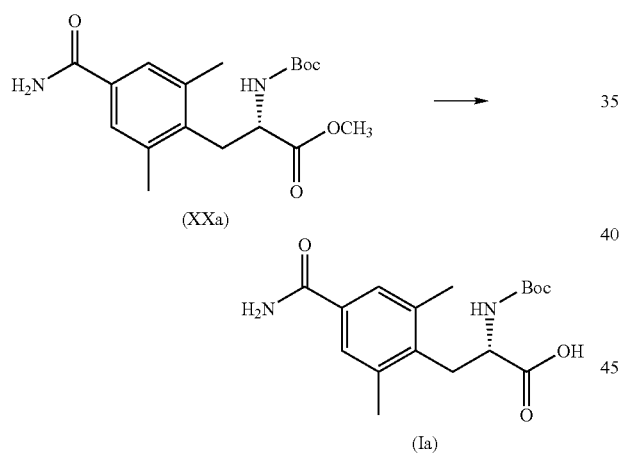

reacting the compound of formula (XXa) with an aqueous base; in an organic solvent; to yield the corresponding compound of formula (Ia).

6. The process as in claim 5, wherein $X^P$ is —OH and wherein $Y^P$ is Br.

7. The process as in claim 6, further comprising

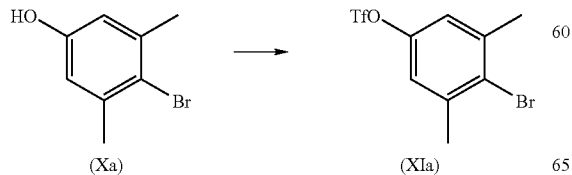

reacting the compound of formula (Xa), with a triflating reagent; in the presence of an organic or inorganic base; to yield the corresponding compound of formula (XIa);

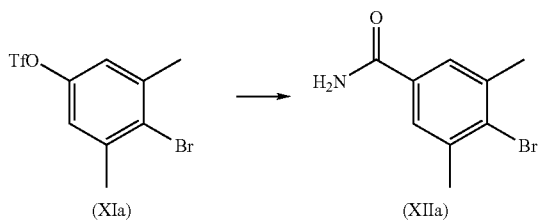

reacting the compound of formula (XIa) with carbon monoxide and a source of ammonia; in the presence of a palladium catalyst in combination with a ligand; or in the presence of a palladium:ligand complex; at a temperature in the range of from about 50° C. to about 160° C.; in an organic solvent; to yield the corresponding compound of formula (XII).

8. The process as in claim 5, wherein the compound of formula (XIIa) is reacted with the compound of formula (XVIIIa) in the presence of $Pd_2(dba)_3$ and P(o-toluene)$_3$.

9. The process as in claim 5, wherein the chiral catalyst is $[Rh(cod)(R,R-DIPAMP)]^+BF_4^-$.

10. A process for the preparation of the compound of formula (Ia)

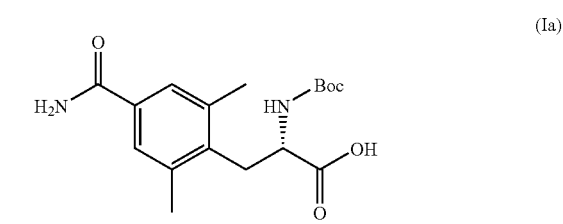

comprising

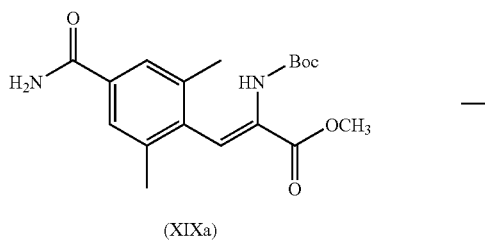

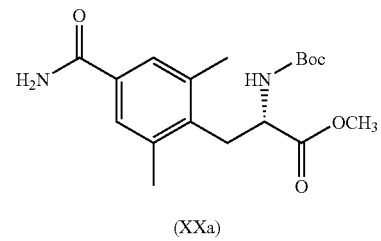

reacting compound of formula (XIXa) with hydrogen gas, at a pressure greater than about 500 psi; in the presence of a chiral catalyst; at a temperature greater than about room temperature; in an organic solvent; to yield the corresponding compound of formula (XXa);

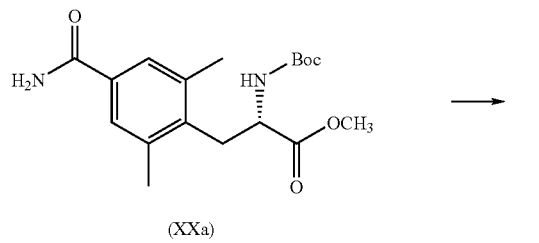

(XXa)

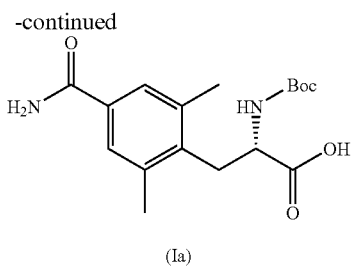

(Ia)

reacting the compound of formula (XXa) with an aqueous base; in an organic solvent; to yield the corresponding compound of formula (Ia).

* * * * *

UNITED STATES PATENT AND TRADEMARK OFFICE
CERTIFICATE OF CORRECTION

PATENT NO. : 7,629,488 B2 Page 1 of 1
APPLICATION NO. : 11/368564
DATED : December 8, 2009
INVENTOR(S) : Cai et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 730 days.

Signed and Sealed this

Second Day of November, 2010

David J. Kappos
*Director of the United States Patent and Trademark Office*